US008420620B2

(12) United States Patent
Tosato et al.

(10) Patent No.: US 8,420,620 B2
(45) Date of Patent: Apr. 16, 2013

(54) INDUCED INTERNALIZATION OF SURFACE RECEPTORS

(75) Inventors: Giovanna Tosato, Bethesda, MD (US); Masashi Narazaki, Minoo (JP)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 144 days.

(21) Appl. No.: 12/864,492

(22) PCT Filed: Jan. 23, 2009

(86) PCT No.: PCT/US2009/031865
§ 371 (c)(1),
(2), (4) Date: Jul. 23, 2010

(87) PCT Pub. No.: WO2009/094561
PCT Pub. Date: Jul. 30, 2009

(65) Prior Publication Data
US 2010/0297124 A1    Nov. 25, 2010

Related U.S. Application Data

(60) Provisional application No. 61/023,397, filed on Jan. 24, 2008.

(51) Int. Cl.
*A01N 43/04*    (2006.01)
*A61K 31/715*   (2006.01)
*C07H 21/02*    (2006.01)
*C07H 1/00*     (2006.01)

(52) U.S. Cl.
USPC ............ 514/54; 514/59; 536/23.1; 536/123.1

(58) Field of Classification Search .................. None
See application file for complete search history.

(56) References Cited

U.S. PATENT DOCUMENTS 5,877,305 A * 3/1999 Huston et al. ............... 536/23.53
2005/0113297 A1* 5/2005 Francois et al. ................ 514/12
2007/0141070 A1  6/2007 Mrsny
2007/0166788 A1  7/2007 Jin et al.

FOREIGN PATENT DOCUMENTS
WO    WO 2007/072504 A1    6/2007

OTHER PUBLICATIONS

Srividya et al., Biochem. Biophys. Res. Commun., 2000, 268, 772-777.*
Narazaki et al., Blood, 2010, 116(16): 3099-3107.*
International Search Report and Written Opinion dated Jun. 17, 2009, issued in corresponding PCT Application No. PCT/US2009/031865, filed Jan. 23, 2009.
Adachi and Tsujimoto, "Endothelial scavenger receptors," *Progress in Lipid Research* 45:379-404, 2006.

Brasseur et al., "Receptor-Mediated Targeting of Phthalocyanines to Macrophages Via Covalent Coupling to Native or Maleylated Bovine Serum Albumin," *Photochem Photobiol.* 69(3):345-52, 1999.
Chabut et al., "Low molecular weight fucoidan and haparin enhancethe basic fibroblast growth factor-induced tube formation of endothelial cells through heparan sulfate-dependent 6 overexpression, " *Molecular Pharmacology.* 64(3):696-702, 2003.
Dias et al., "Antiangiogenic and antitumoral properties of a polysaccharide isolated from the seaweed *Sargassum stenophyllum*," *Cancer Chemother Pharmacol.* 56(4):436-46, 2005.
Gruarin et al., "CD36 folding revealed by conformational epitope expression is essential for cytoadherence of *Plasmodium falciparum*-infected red blood cells, " *Parasite Immunology*, 22:349-360, 2000.
Hahnenberger and Jakobson, "Antiangiogenic effect of sulphated and nonsulphated glycosaminoglycans and polysaccharides in the chick embryo chorioallantoic membrane," *Glycoconjugate Journal* 8(4):1573-4986, 1991.
Koyanagi, et al., "Oversulfation of fucoidan enhances its antiangiogenic and antitumor activities," *Biochem Pharmacol.* 65(2):173-9, 2003.
Lake et al., "Low molecular weight fucoidan increases VEGF165-induced endothelial cell migration by enhancing VEGF165 binding to VEGFR-2 and NRP1," *J Biol Chem.* 281(49):37844-52, 2006.
Majumdar et al., "Killing of intracellular Mycobacterium tuberculosis by receptor-mediated drug delivery," *Antimicrob Agents Chemother.* 35(1): 135-140, 1991.
Mukhopadhyay et al., "Scavenger-receptor-mediated delivery of daunomycin elicits selective toxicity towards neoplastic cells of macrophage lineage," *Biochem J.* 284(Pt 1): 237-241, 1992.
Parish et al., "Identification of sulfated oligosaccharide-based inhibitors of tumor growth and metastasis using novel in vitro assays for angiogenesis and heparanase activity," *Cancer Res.* 59(14):3433-41, 1999.
Shinyo et al., "Heparanase expression is an independent prognostic factor in patients with invasive cervical cancer," *Annals of Oncology* 14:1505-1510, 2003.
Wu et al., "Effects of Sulfated Polysaccharides on Tumor Biology," *West Indian Med. J.* 55(4):270-272, 2006.

* cited by examiner

*Primary Examiner* — Hong Sang
(74) *Attorney, Agent, or Firm* — Klarquist Sparkman, LLP

(57) ABSTRACT

Disclosed is a hetero-bifunctional ligand for use in inducing internalization of a target receptor. The hetero-bifunctional ligand includes a target receptor-binding agent that specifically binds the target receptor linked to an internalizing receptor-binding agent that specifically binds to an internalizing receptor, where the two binding agents are non-identical. Also disclosed is a method of inducing the internalization of a target receptor on a cell. The method includes contacting a cell with a hetero-bifunctional ligand, where binding of the hetero-bifunctional ligand induces internalization of a target receptor of the cell. Also disclosed a method of treating a disease or condition associated with a target receptor using the disclosed hetero-bifunctional ligand and pharmaceutical compositions including a hetero-bifunctional ligand.

14 Claims, 28 Drawing Sheets

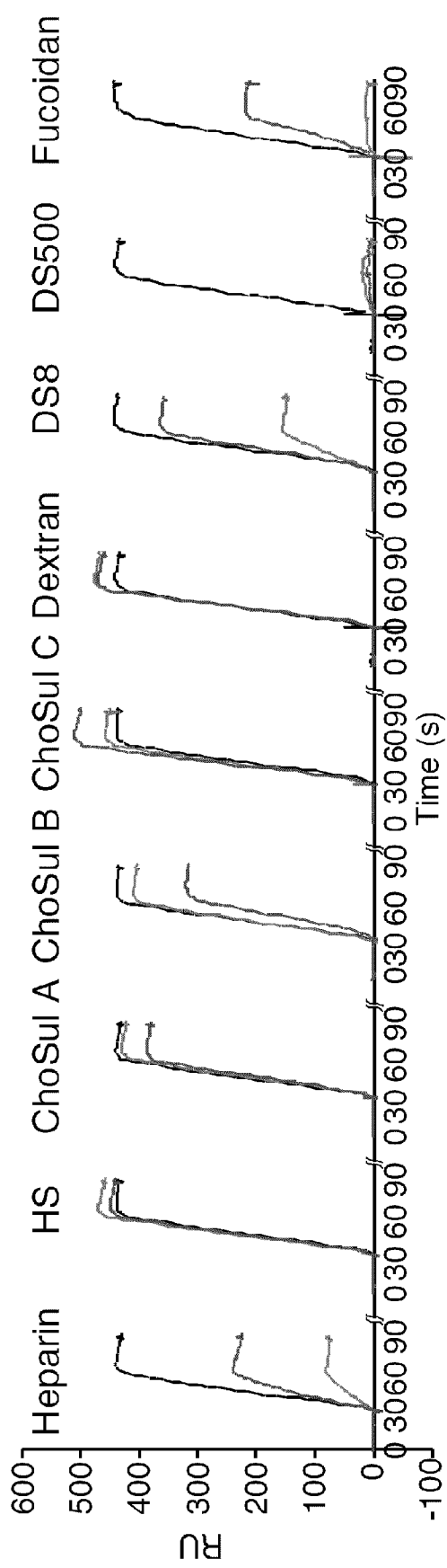
FIG. 1A
FIG. 1B
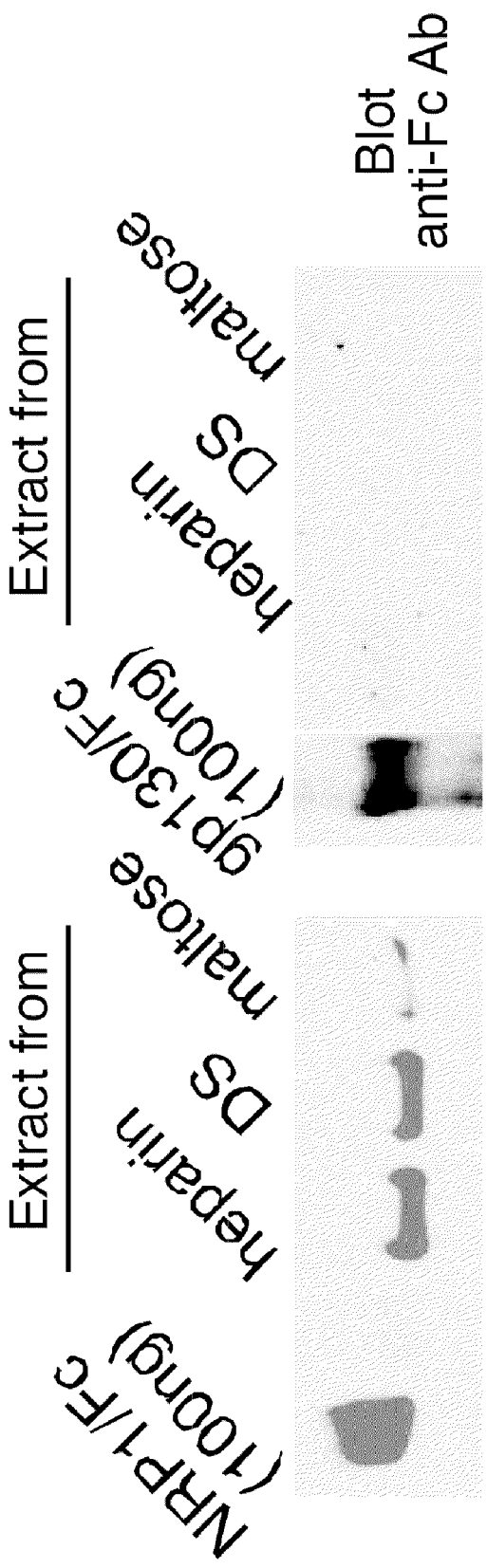

FIG. 1F
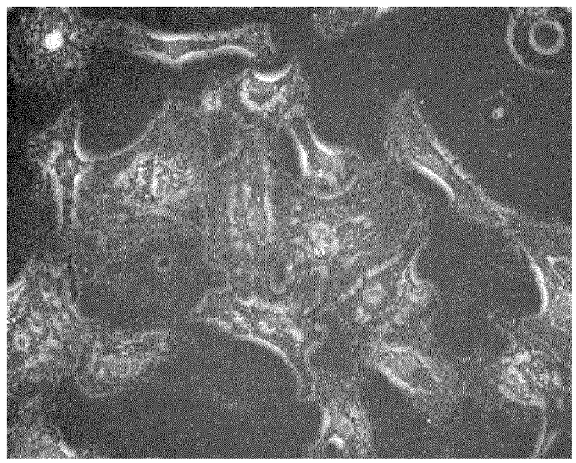 (-)
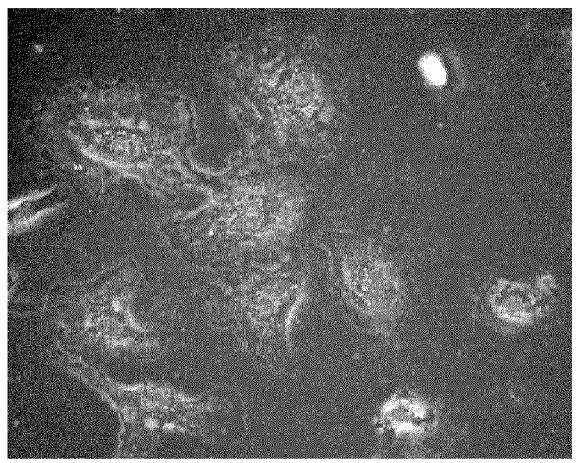 DS500 (+)
FIG. 1G
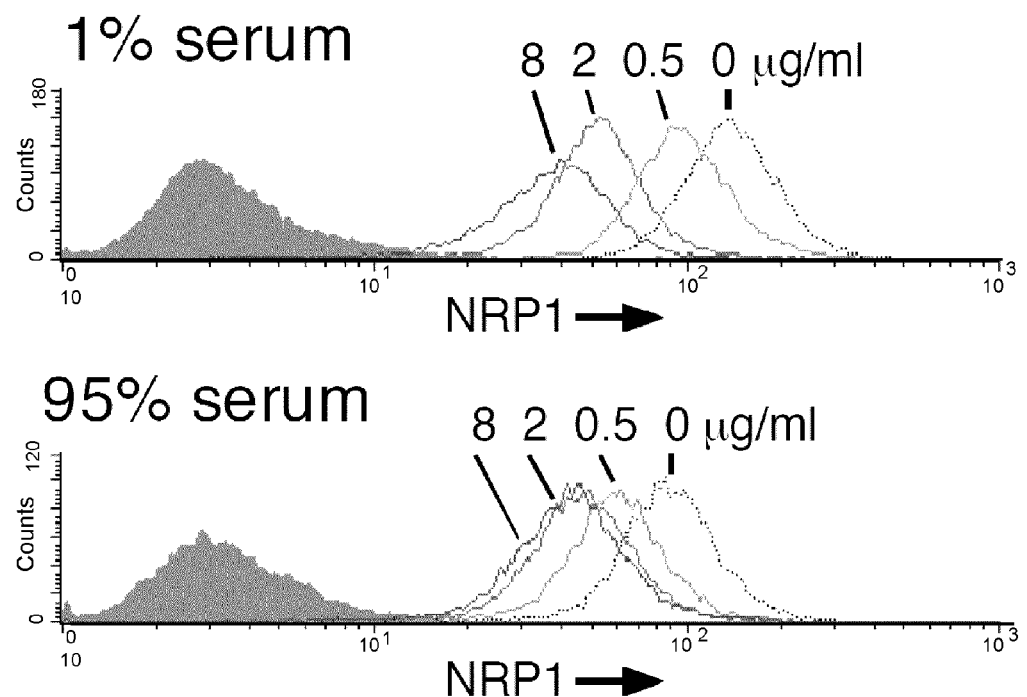

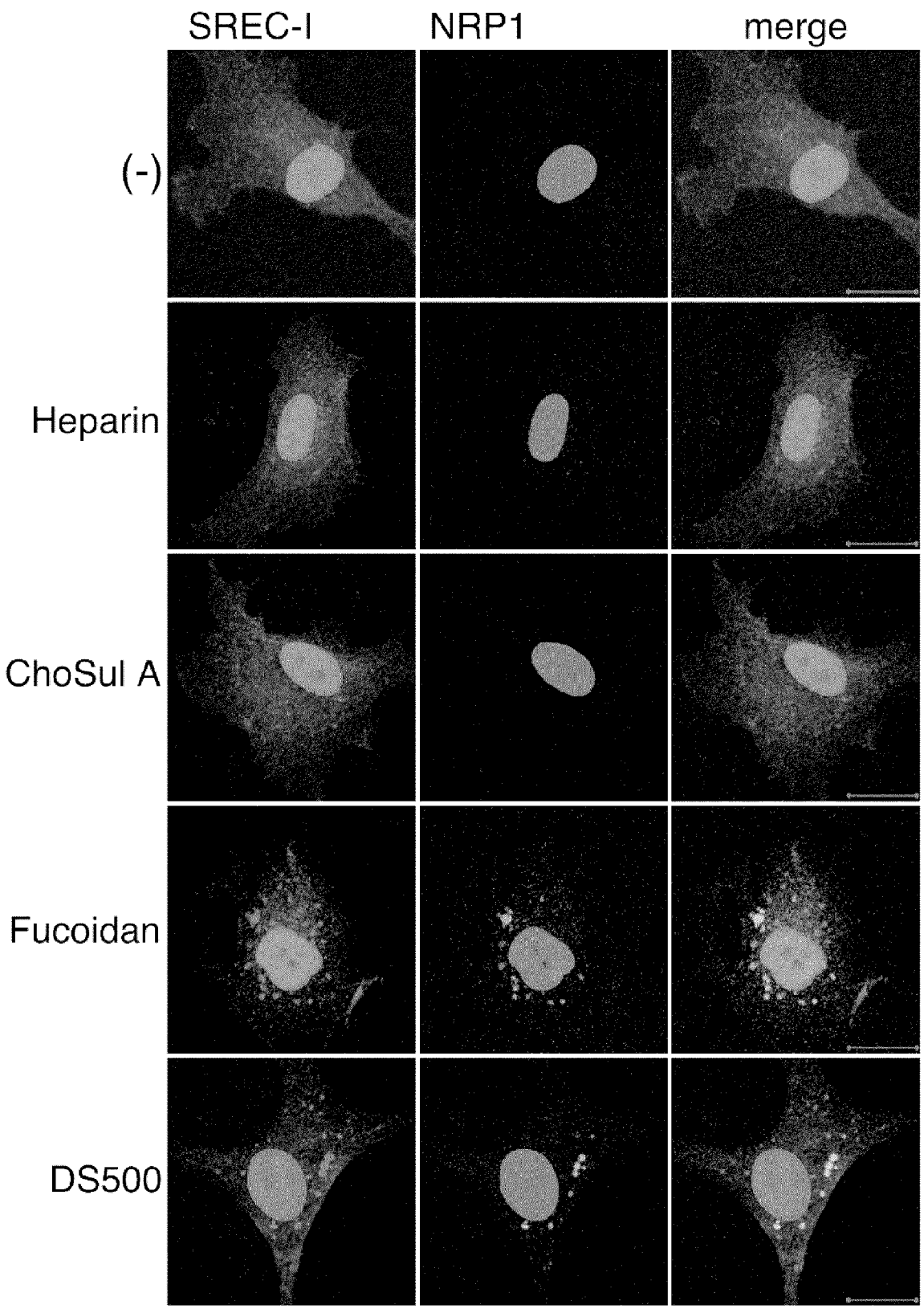

FIG. 5B
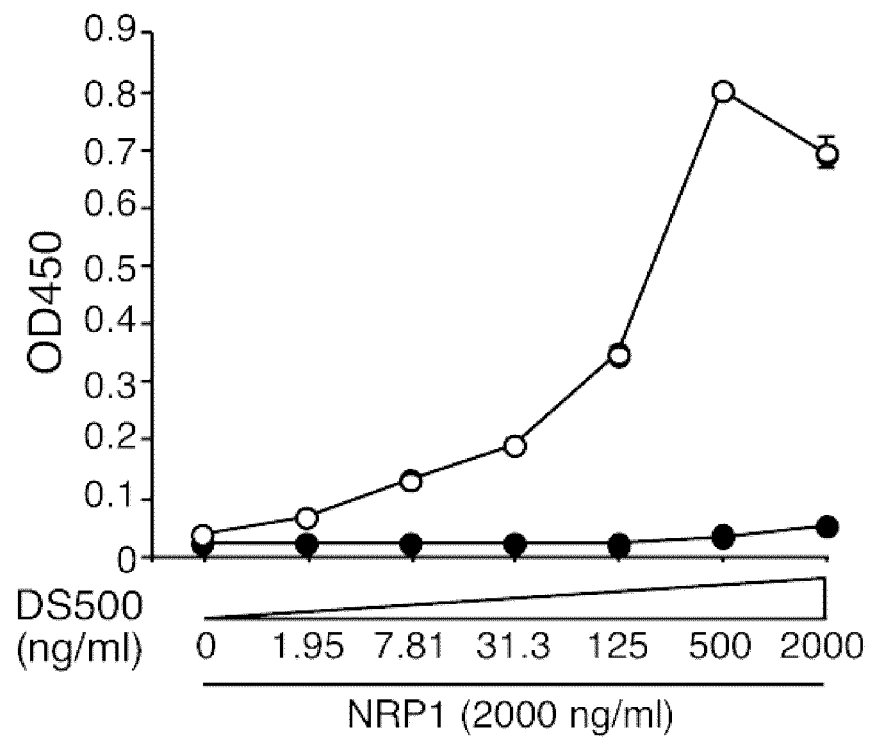
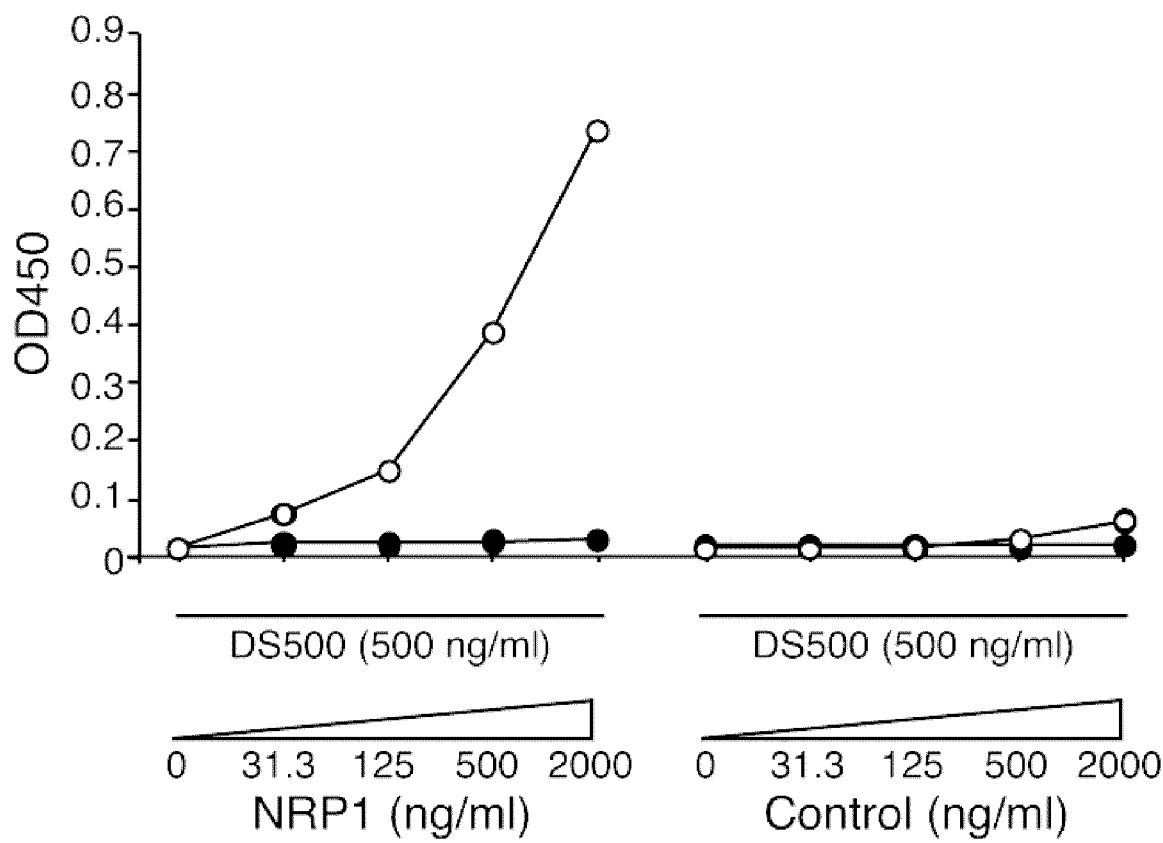

FIG. 7E
Dextran
Fucoidan
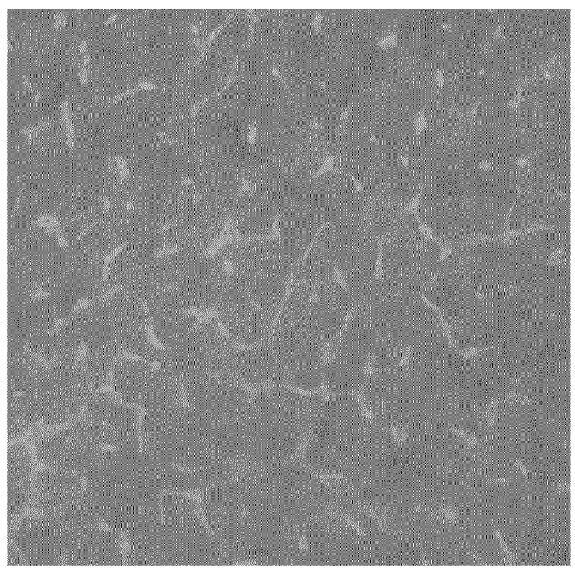
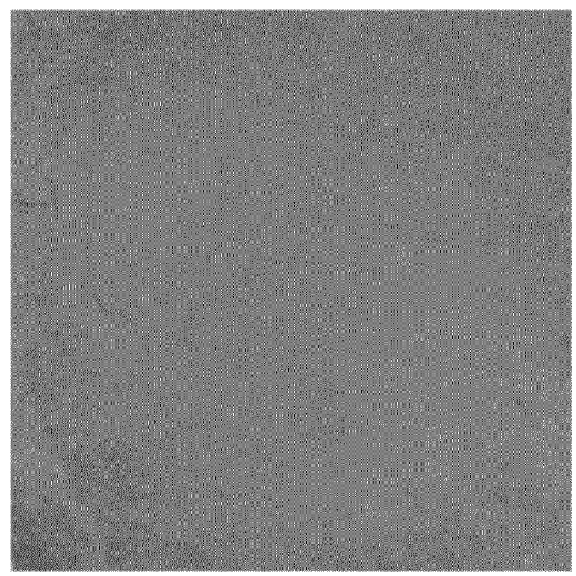
CD31/DAPI
FIG. 7F
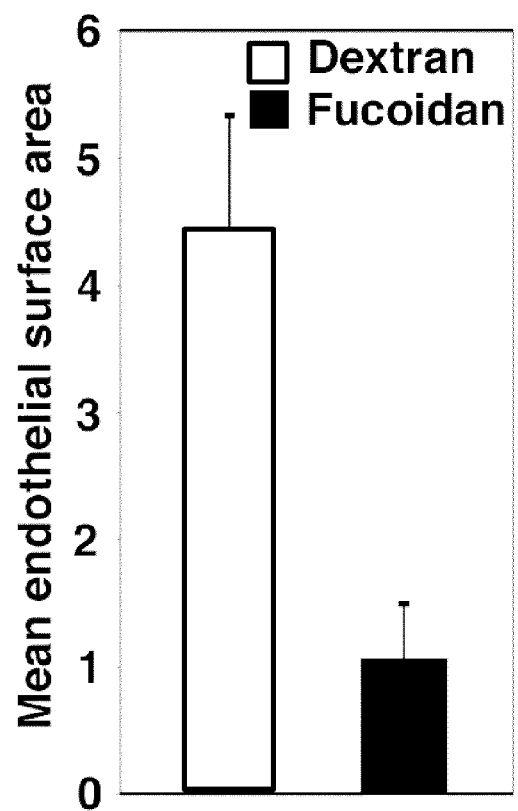

INDUCED INTERNALIZATION OF SURFACE RECEPTORS

CROSS REFERENCE TO RELATED APPLICATION

This is the U.S. National Stage of International Application No. PCT/US2009/031865, filed Jan. 23, 2009, which was published in English under PCT Article 21(2), which in turn claims the benefit of U.S. Provisional Application No. 61/023,397, filed Jan. 24, 2008, which is incorporated herein in its entirety.

FIELD OF THE DISCLOSURE

The present disclosure relates to hetero-bifunctional ligands that bind to and induce the internalization of specific target receptors, and methods for treating and/or inhibiting diseases associated with the target receptors using these hetero-bifunctional ligands.

BACKGROUND

Cell-surface proteins known as receptors are present on the surface of most if not all of the cells that make up an organism. Cell surface receptors enable chemical communication between the different cells that make up the organism. Typically, cell-cell signaling occurs through the binding of ligands, such as small molecules and proteins, to the various receptors present on the surface of a cell. The binding of ligand to a cell surface receptor can initiate cellular responses (in some examples ligand dissociation initiates a cellular response), which can lead to physiological changes in the cell, for example changes in gene expression patterns and/or chemotactic behavior.

A number of diseases, including cancer, metabolic disorders and viral infections are known to be involved with the expression of cell-surface receptors in their development and/or progression. In the case of viral infection, cell-surface receptors can serve as sites of attachment and entry for viruses, such as human immunodeficiency virus (HIV). In cancer, particularly metastatic progression of cancer, angiogenesis is believed to be mediated by the secretion of growth factors and their binding by cognate receptors on capillary-forming cells. The recognition that cellular surface receptors and their signaling can play a role in human disease has prompted significant research efforts toward the development of pharmaceutical agents that block the signals from cell-surface receptors. For example, agents have been sought that bind the extracellular portion of cell surface receptors and inhibit the binding of the receptor's cognate ligand or agents that bind the intracellular portion of the receptor and prevent signal propagation inside the cell.

The epidermal growth factor receptor (EGFR) has been the target for development of agents that bind the extracellular or intracellular portion of the cell surface receptor. EGFR is frequently overexpressed in a wide range of human tumors. Such overexpression often correlates with poor prognosis and worse clinical outcome. Two classes of anti-EGFR agents have entered clinical practice: monoclonal antibodies and small molecules targeting the receptor tyrosine kinase domain of EGFR. The monoclonal antibodies to EGFR inhibit the binding of EGF to the extracellular domain of EGFR, effectively stopping the signal at the surface of the cell. Small molecules that target the receptor tyrosine kinase domain pass into the interior of the cell where they bind to the EGFR kinase domain and inhibit the catalytic activity of the kinase.

A strategy similar to the EGFR blocking antibodies is being used in the fight against HIV infection. The chemokine receptors CCR5 and CXCR4 were identified as HIV-1 co-receptors in 1996. Since then, a range of agents that bind these receptors and potently block HIV-1 infection have been described, including monoclonal antibodies, peptides and modified chemokines. These anti-HIV agents bind to the chemokine receptors and inhibit the ability of HIV to bind to the chemokine receptors and use them as an entry point into cells.

While the therapeutic approaches described above show great promise for specific applications, the need still exists for new therapeutic strategies that work at the level of cell surface receptors, such as to down-regulate the receptor on the surface of a cell of interest.

SUMMARY OF THE DISCLOSURE

Disclosed herein is a hetero-bifunctional ligand for use in inducing internalization of a target receptor. The disclosed hetero-bifunctional ligand includes a target receptor-binding agent that specifically binds a target receptor, wherein the target receptor binding agent is linked to an internalizing receptor-binding agent that specifically binds to an internalizing receptor. The target receptor-binding agent and the internalizing receptor-binding agent are not identical. Binding of such a hetero-bifunctional ligand to an internalizing receptor and the target receptor on the surface of a cell induces the internalization of both the internalizing receptor and the target receptor. In some disclosed examples, the hetero-bifunctional ligand includes, as target receptor-binding agent, an antibody (for example a monoclonal and/or humanized antibody), a small molecule or a ligand that specifically binds the target receptor. In some embodiments, the target receptor-binding agent is a target receptor ligand, for example a cytokine, a chemokine, a growth factor, a hormone, a neuropeptide or a portion thereof that specifically binds the target receptor. In a specific example, the target receptor-binding agent of the hetero-bifunctional ligand is a ligand or antibody for a CCR5 receptor. In another specific example, the target receptor-binding agent of the hetero-bifunctional ligand is vascular endothelial growth factor-A (VEGF-A).

Examples of internalizing receptors include scavenger receptors, low-density lipoprotein (LDL) receptors, heat shock protein receptors and transferrin receptors. Thus, in some embodiments the internalizing receptor-binding agent of a disclosed hetero-bifunctional ligand includes a scavenger receptor ligand, an LDL receptor ligand, a transferrin receptors ligand or a heat-shock protein receptor ligand. In a specific non-limiting example, the target receptor-binding agent of the hetero-bifunctional ligand is VEGF-A and the internalizing receptor-binding agent is Acetylated-LDL. In some examples, a target receptor-binding agent is an oligonucleotide. In some examples, an internalizing receptor-binding agent is an oligonucleotide.

Pharmaceutical compositions are disclosed that include a therapeutically effective amount of the hetero-bifunctional ligand.

Methods of inducing internalization of a target receptor on a cell are disclosed. Examples of these methods include contacting the cell with an effective amount of a hetero-bifunctional ligand. Disclosed methods can be used to treat a disease or condition associated with a target receptor, such as cancer or a viral infection. Such methods include administering a therapeutically effective amount of a hetero-bifunctional ligand to a subject, thereby treating the disease or condition. In specific examples, the method is a method of treating or inhibiting an HIV infection by administering to a subject a therapeutically effective amount of a hetero-bifunctional ligand that includes a ligand or antibody for a cytokine receptor such as a CCR5 receptor ligand linked to an internalizing receptor ligand that specifically binds to and induces internalization of both the internalizing receptor and cytokine receptor. The CCR5 receptor ligand and the internalizing receptor ligand are not identical and they target different receptors.

The foregoing and other objects, features and advantages of the invention will become more apparent from the following detailed description, which proceeds with reference to the accompanying figures.

BRIEF DESCRIPTION OF THE DRAWINGS

FIGS. 1A-1G are graphs and digital images and histograms demonstrating the effect of polysaccharides on neuropilin 1 (NRP1) FIG. 1A is a set of graphs showing the effects of polysaccharides on NRP1 binding to heparin. NRP1 (20 nM) was passed over a heparin-coated sensor chip without, with 0.1 µg/ml or 1 µg/ml polysaccharide. FIG. 1B is a set of digital images of immunoblots showing the binding of NRP1 to dextran sulfate. NRP1/Fc (1 µg/ml) or gp130/Fc (1 µg/ml) was incubated with heparin-gel, DS-gel, maltose-gel and the precipitates were detected by anti-Fc antibody. NRP1/Fc or gp130/Fc (100 ng) was loaded as a control. FIG. 1C is a graph showing the modulation of cell-surface NRP1 by polysaccharides. Human umbilical vein endothelial cells (HUVEC) were incubated with the polysaccharides (0-64 µg/ml, 37° C., 1 hour). After cell washing (1M NaCl), NRP1 was detected by flow cytometry. Results reflect the relative mean fluorescence intensities with and without polysaccharide. FIG. 1D is a set of histograms from a flow cytometry analysis of the effects of DS500 on levels of cell-surface molecules NRP1, neuropilin 2 (NRP2), vascular endothelial growth factor receptor 2 (VEGFR-2), vascular endothelial growth factor receptor 1 (VEGFR-1), CD31, VE-Cadherin, gp130 and CXCR4. HUVEC were incubated (37° C., 1 hour) with or without DS500 (8 µg/ml). Shaded graphs reflect control staining. FIG. 1E is a graph of the temperature, concentration and time-dependent reduction of cell surface NRP1 and NRP2 by DS500. HUVEC were incubated with DS500. NRP1 and NRP2 were detected by flow cytometry. FIG. 1F is a digital image of HUVEC treated (37° C., 1 hour) with or without DS500 (8 µg/ml), stained for NRP1 and DAPI, fixed and observed through an Olympus IX51 phase-contrast microscope equipped with a 10×/0.25 PhC objective lens and a 10× eyepiece (Olympus Optical, Melville, N.Y.) and photographed with a RETIGA™ 1300 digital camera (QIMAGING®, Burnaby, BC, Canada). Original magnification, ×100. Images reflect the merging of fluorescent slice of NRP1 and DAPI images. Scale bar, 20 µm. FIG. 1G is a set of histograms from a flow cytometry analysis of NRP1 detected on HUVEC incubated with DS500 (0-8 µg/ml, 37° C., 1 hour) in the presence of 1% or 95% human serum.

FIG. 2A is a set of digital images showing that DS500 induces NRP1 internalization. HUVEC grown on fibronectin-coated glass slides were incubated with DS500 (8 µg/ml, 37° C., 0-60 minutes). After fixation and permeabilization, cells were stained with anti-NRP1 monoclonal antibody (mAb) and examined through an LSM510 confocal microscope equipped with a PLAN-NEOFLUAR® 40×1/1.3 objective lens (Carl Zeiss). Images reflect the merging of fluorescent slice images of NRP1, 4',6-diamidino-2-phenylindole (DAPI) and differential interference contrast image. Images were imported into ADOBE® PHOTOSHOP® 6.0 (ADOBE® Systems, San Jose Calif.) for processing. Scale bar=20 µm. FIG. 2B is a set of digital images showing that NRP1 co-localizes with Lamp1. HUVEC were incubated with DS500 (8 µg/ml, 37° C., 1 hour). After fixation and permeabilization, cells were stained for NRP1, Lamp1 and DAPI and examined by confocal microscopy. FIG. 2C is a set of immunoblots and a bar graph showing that DS500 reduces protein levels of NRP1. Cell lysates of HUVEC treated with DS500 (2 µg/ml, 37° C., 0-90 minutes) were blotted with anti-NRP1 Ab (upper panel) and reblotted with anti-Actin antibody (Ab) (lower panel). Relative ratios of NRP1/Actin band intensities are shown in the lower bar graph.

FIG. 3A is a set of histograms from a flow cytometry analysis of cell-surface NRP1 in HUVEC, RS4, HS-5 and COS7-NRP1 cells. FIG. 3B is a graph showing that the reduction of cell surface NRP1 is detected on HUVEC, but not RS4, HS-5 and COS7-NRP1 cells after stimulation with DS500 (0, 0.5, 2, 8 µg/ml, 37° C., 1 hour). Results reflect the relative mean fluorescence intensities with and without stimulation. FIG. 3C is a graph showing uptake of acLDL (DiO-Ac-LDL) (0, 0.25, 1, 4 µg/ml, 37° C., 1 hour) by HUVEC, but not RS4, HS-5 and COS7-NRP1 cells detected by flow cytometry. Open circles indicate cell uptake of DiO-Ac-LDL (4 µg/ml) in the presence of competitor Ac-LDL (100 µg/ml). Results reflect mean fluorescence intensities after background subtraction.

FIG. 4A is a set of digital images showing that the scavenger receptor expressed by endothelial cells −1 (SREC-I) internalized by Ac-LDL localizes with Ac-LDL. SREC-I and DAPI were examined by confocal microscopy in HUVEC incubated with Alexa594-conjugated Ac-LDL (4 µg/ml, 37° C., 1 hour), fixed and permeabilized. Scale bar=20 µm. Images were acquired and processed as described for FIG. 3A. FIG. 4B is a graph showing that DS500 and Fucoidan reduce cell-surface levels of SREC-I. HUVEC were incubated with polysaccharides (0-64 µg/ml, 37° C., 1 hour) and washed (1M NaCl). SREC-I was detected by flow cytometry. Results reflect relative mean fluorescence intensities with or without stimulation. FIG. 4C is a graph showing the temperature, concentration and time-dependent reduction of cell-surface SREC-I by DS500. HUVEC were incubated with DS500. SREC-I was detected by flow cytometry. FIG. 4D is a set of digital images showing that DS500 induces SREC-I internalization. SREC-I and DAPI were examined by confocal microscopy in HUVEC incubated with DS500 (8 µg/ml, 37° C., 1 hour), fixed and permeabilized. Scale bar=20 µm. FIG. 4E is a set of digital images showing that SREC-I co-localizes with Lamp1. SREC-I, Lamp1 and DAPI were examined by confocal microscopy in HUVEC incubated with DS500 (8 µg/ml, 37° C., 1 hour), fixed and permeabilized.

FIGS. 5A-5D is a set of digital images, graphs and histograms. FIG. 5A is a set of digital images showing co-localization of SREC-I and NRP1 in the cytoplasm after Fucoidan or DS500 stimulation. HUVEC were incubated (37° C., 1 hour) with medium alone, heparin, ChoSulA, Fucoidan or DS500 (8 µg/ml). After fixation and permeabilization, cells were stained for SREC-I, NRP1 and DAPI and examined by confocal microscopy. Scale bar=20 μm. Images were acquired and processed as described for FIG. 2A. FIG. 5B is a set of graphs showing that DS500 specifically and dose-dependently promotes binding of NRP1 to SREC-I. NRP1/Fc or control Fc protein (B7-1/Fc) was added to control IgG1-coated wells (filled circles) or SREC-I/Fc-coated wells (open circle) with or without DS500. Bound NRP1 or control/Fc was measured by enzyme-linked immunosorbent assay (ELISA). The results reflect the means±SD of 3 trials. FIG. 5C is a bar graph showing the effect of polysaccharides on the binding of NRP1 to SREC-I. NRP1/Fc (2 μg/ml) was added to SREC-1/Fc coated wells in the presence of the indicated polysaccharide (500 ng/ml). Bound NRP1/Fc was measured by ELISA. The results reflect the means±SD of 3 trials. FIG. 5D is a set of histograms from a flow cytometry analysis showing that transduction of 293 cells with SREC-I confers DiO-Ac-LDL uptake capability and reduces cell-surface levels of NRP1, but not levels of gp130 or CXCR4. 293 cells were transfected with cDNA for SREC-I or control. Uptake of DiO-Ac-LDL and cell surface levels of endogenous gp130, CXCR4 or NRP1 were detected by flow cytometry. Shaded graphs reflect control staining.

FIG. 6A is a graph showing that DS500 and Fucoidan block Sema3A binding to HUVEC. Cells were incubated with DS500 (closed circle) (0-8 μg/ml), heparin (triangle), ChoSulA (square), dextran (diamond) or Fucoidan (open circle) (8 μg/ml), washed (1M NaCl) and incubated with Sema3A/Fc. Bound Sema3A/Fc was detected by flow cytometry. FIG. 6B is a set of digital images showing that DS500 and Fucoidan inhibit Sema3A-induced lamellipodia retraction in HUVEC. After pre-incubation with or without DS500 or Fucoidan, HUVEC were allowed to attach onto fibronectin-coated slides and then incubated with or without Sema3A/Fc. Magnification, 100×. FIG. 6C is a bar graph showing that DS500 and Fucoidan inhibit Sema3A-induced lamellipodia retraction in HUVEC. After pre-incubation with or without DS500 or Fucoidan, HUVEC were allowed to attach onto fibronectin-coated slides and then incubated with or without Sema3A/Fc. Average retraction scores (±SD of 4 fields). $p<0.01$. FIG. 6D is a graph showing that DS500 and Fucoidan block $VEGF_{165}$ binding to HUVEC. Bound $VEGF_{165}$ was detected by flow cytometry. Experimental conditions as described in FIG. 6A. FIG. 6E is a bar graph showing that DS500 and Fucoidan inhibit $VEGF_{165}$-induced proliferation of HUVEC. Cells were cultured (3 days) with ChoSulA, DS500 or Fucoidan in the presence of $VEGF_{165}$ (25 ng/ml); proliferation was measured by $^3$H-thymidine uptake. Results are expressed as mean cpm/culture (±SD of triplicate cultures).

FIGS. 7A-7F are bar graphs and digital images. FIGS. 7A and 7B are two bar graphs showing that Fucoidan inhibits angiogenesis in vivo. FIG. 7A and FIG. 7B show the effects of Fucoidan on VEGF-induced angiogenesis in MATRIGEL™ plugs. Mice bearing MATRIGEL™ plugs containing VEGF (0 or 150 ng/ml) plus heparin (0 or 500 ng/ml) were injected daily intraperitoneally (i.p.) for 6 days with Fucoidan or control non-sulfated dextran (1 mg/mouse/day). After the plugs were fixed and immunostained for CD31/PECAM, endothelial cell density was evaluated microscopically (Nikon Eclipse E600 equipped with a DIC M 20×/0.75 Nikon lens). Images were imported into IPLab software and the area occupied by $CD31^+$ cells quantified. The results are expressed as mean (±SD) surface areas (μm$^2$) occupied by $CD31^+$ cells within a unit area ($10^6$ μm$^2$). In FIG. 7A the 2 groups consisted of 5 C57BL/6J 7-week old female mice. In FIG. 7B the 4 groups consisted of 6 BALB/cAnCr 6-weeks old female mice. FIGS. 7C and 7D are two bar graphs showing the effects of Fucoidan on tumor growth in mice. Mean (±SEM). FIG. 7C shows tumor size (expressed in mm$^2$) and FIG. 7D shows tumor weight (expressed in grams) in the 2 groups of 15 female BALB/cAnCr 6-weeks old mice inoculated subcutaneously (s.c.) with $10^7$ MOPC315 tumor cells and subsequently treated daily for 7 days with Fucoidan or control non-sulfated dextran. FIG. 7E is a set of digital images showing CD31/platelet endothelial cell adhesion molecule-1 (PECAM) immunostaining of tumor tissues from mice treated with Fucoidan or control non-sulfated dextran. Original magnification 20×. FIG. 7F is a bar graph showing quantification of vascular infiltration in tumor tissues using IPLab Software. The results are expressed as the mean (±SD) surface areas occupied by $CD31^+$ cells within a unit area (μm$^2$/$10^6$ μm$^2$).

DETAILED DESCRIPTION

I. Terms

Figure 1C:
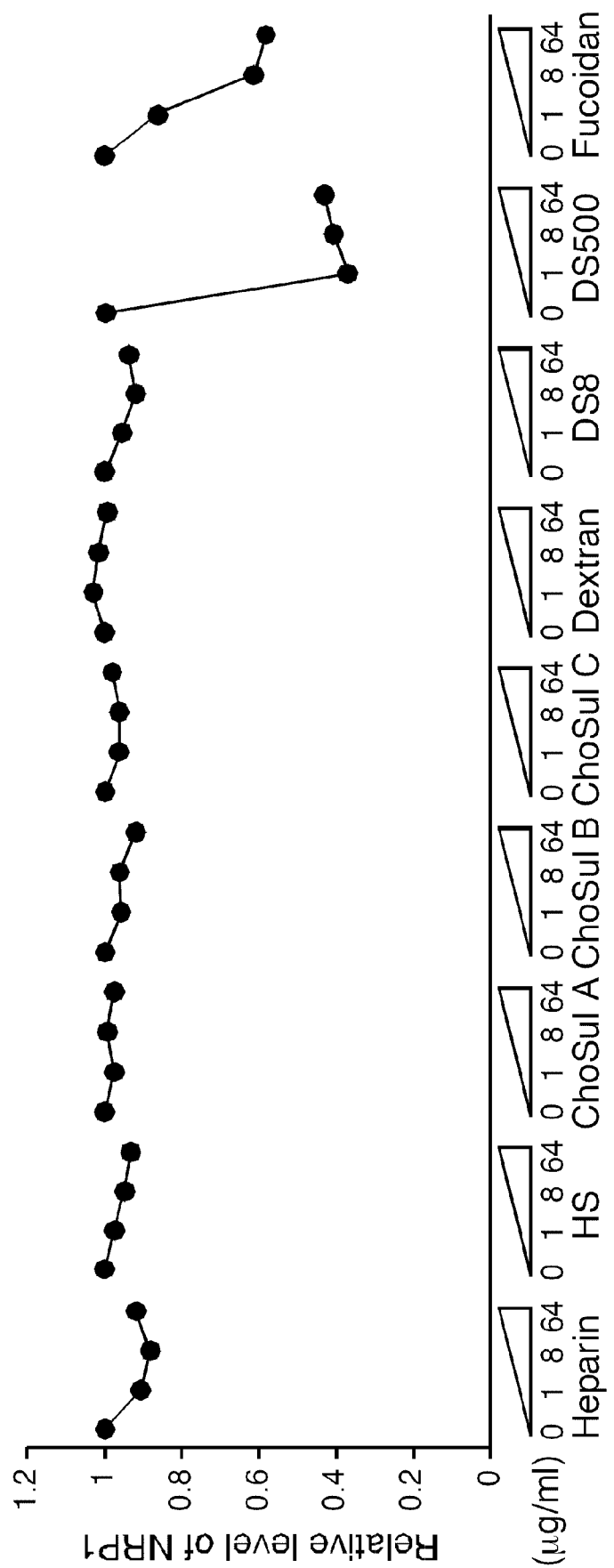

Unless otherwise noted, technical terms are used according to conventional usage. Definitions of common terms in molecular biology may be found in Benjamin Lewin, *Genes*

VII, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B or A and B. Although many methods and materials similar or equivalent to those described herein can be used, particular suitable methods and materials are described below. In case of conflict, the present specification, including explanations of terms, will control. In addition, the materials, methods and examples are illustrative only and not intended to be limiting.

To facilitate review of the various embodiments of this disclosure, the following explanations of specific terms are provided:

Angiogenesis: A biological process leading to the generation of new blood vessels through sprouting or growth from pre-existing blood vessels or from circulating endothelial precursors. The process involves the migration and proliferation of endothelial cells from preexisting vessels. Angiogenesis occurs during pre-natal development, post-natal development and in the adult. In the adult, angiogenesis occurs during the normal cycle of the female reproductive system, wound healing and during pathological processes such as cancer (for a review see Battegay, *J. Molec. Med.* 73(7): 333-346, 1995).

Aptamer: Small nucleic acid and peptide molecules that bind a specific target molecule, such as a target biomolecule, for example a target receptor or internalizing receptor.

Animal: A living multicellular vertebrate organism, a category which includes, for example, mammals and birds. A "mammal" includes both human and non-human mammals. Similarly, the term "subject" includes both human and veterinary subjects.

Adjuvant: A vehicle used to enhance antigenicity; such as a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules and for example, immunostimulatory DNA or RNA molecules, such as CpG oligonucleotides.

Antibody: A polypeptide ligand comprising at least a light chain or heavy chain immunoglobulin variable region, which specifically recognizes and binds an epitope of an antigen, such as target receptor or a fragment thereof. This includes intact immunoglobulins and the variants and portions of them well known in the art, such as Fab' fragments, F(ab)'$_2$ fragments, single chain Fv proteins ("scFv") and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (such as humanized murine antibodies), heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., (1991) *Sequences of Proteins of Immunological Interest*, 5$^{th}$ Edition, U.S. Department of Health and Human Services, Public Health Service, National Institutes of Health, Bethesda, Md. (NIH Publication No. 91-3242) which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space, for example to hold the CDRs in an appropriate orientation for antigen binding.

The CDRs are primarily responsible for binding to an epitope of an antigen. The CDRs of each chain are typically referred to as CDR1, CDR2 and CDR3, numbered sequentially starting from the N-terminus and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

A "monoclonal antibody" is an antibody produced by a single clone of B-lymphocytes or by a cell into which the light and heavy chain genes of a single antibody have been transfected or transduced. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

A "humanized" immunoglobulin, is an immunoglobulin including a human framework region and one or more CDRs from a non-human (such as a mouse, rat or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, for example at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example see U.S. Pat. No. 5,585,089).

In some embodiments, an antibody is a ligand for a receptor, such as a ligand for a target receptor, for example a target receptor antibody. In some embodiments, a target receptor antibody is linked to a specific binding agent for an internalizing receptor, for example to create a hetero-bifunctional ligand that can bind to both an internalizing receptor and a target receptor.

Binding affinity: Affinity of a specific binding agent for its target, such as an antibody for an antigen, for example an antibody for a target receptor. In one embodiment, affinity is calculated by a modification of the Scatchard method described by Frankel et al., *Mol. Immunol.,* 16:101-106, 1979. In another embodiment, binding affinity is measured by a specific binding agent receptor dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$ or at least about $5.0 \times 10^{-8}$ M.

Cancer: A disease characterized by the abnormal growth and differentiation of cells. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma and other sarcomas, synovioma, mesothelioma, Ewing's tumor, leiomyosarcoma, rhabdomyosarcoma, colon cancer (such as colon carcinoma), gastric cancer, (for example, gastric adenocarcinoma, such as intestinal type gastric adenocarcinoma and diffuse type gastric adenocarcinoma), lymphoid malignancy, pancreatic cancer, breast cancer (such as adenocarcinoma), lung cancers, gynecological cancers (such as, cancers of the uterus (for example endometrial carcinoma), cervix (for example cervical carcinoma, pre-tumor cervical dysplasia), ovaries (for example ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (for example squamous cell carcinoma, intraepithelial carcinoma, adenocarcinoma, fibrosarcoma, melanoma), vagina (for example clear cell carcinoma, squamous cell carcinoma, botryoid sarcoma), embryonal rhabdomyosarcoma and fallopian tubules (for example carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma) and skin cancer (such as melanoma and non-melanoma).

Contacting: Placement in direct physical association including both in solid or liquid form. Contacting can occur in vivo, for example by administering an agent to a subject, in vitro. "Administration" is the introduction of a composition, such as a composition containing a hetero-bifunctional ligand, into a subject by a chosen route. For example, if the chosen route is intravenous, the composition is administered by introducing the composition into a vein of the subject.

"Administrating" to a subject includes topical, parenteral, oral, intravenous, intra-muscular, sub-cutaneous, inhalational, nasal or intra-articular administration, among others.

Chemokines: Proteins classified according to shared structural characteristics such as small size (approximately 8-10 kilodaltons (kD) in size) and the presence of four cysteine residues in conserved locations that are key to forming their 3-dimensional shape. These proteins exert their biological effects by interacting with G protein-linked transmembrane receptors called chemokine receptors that are selectively found on the surfaces of their target cells. Chemokines bind to chemokine receptors and thus are chemokine receptor ligands.

Examples of chemokines include the CCL chemokines such as CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27 and CCL28; CXCL chemokines such as CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16 and CXCL17; XCL chemokines such as XCL1 and XCL2; and CX3CL chemokines such as CX3CL1. In some examples, a chemokine or portion thereof sufficient to bind to a chemokine receptor is part of a hetero-bifunctional ligand.

Chemotherapeutic agents: Any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating a tumor. In one embodiment, a chemotherapeutic agent is a hetero-bifunctional ligand. One of skill in the art can readily identify a chemotherapeutic agent of use (for example, see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy,* 2nd ed. St.

Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer, for example the administration of a hetero-bi-functional ligand and alkylating agent.

Covalent bond: An interatomic bond between two atoms, characterized by the sharing of one or more pairs of electrons by the atoms. The terms "covalently bound" or "covalently linked" refer to making two separate molecules into one contiguous molecule, for example a binding agent specific for a target receptor can be covalently linked (such as directly or indirectly through a linker) to an internalizing receptor-binding agent.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Cytokines include both naturally occurring peptides and variants that retain full or partial biological activity. Cytokines bind to cytokine receptors and thus are cytokine receptor ligands.

Examples of cytokines include interleukins, such as IL-1α, IL-1β, IL-2, IL-3, IL-4, IL-5, IL-6, IL-7, IL-8, IL-10 and IL-12; interferons, such as IFN-α, IFN-β and IFN-γ; tumor necrosis factors, such as TNF-α and TNF-β macrophage; inflammatory proteins, such as MIP-1α and MIP-1β; and transforming growth factors, such as TGF-β. In some examples, a cytokine or portion thereof sufficient to bind to a cytokine receptor is part of a hetero-bifunctional ligand.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: Translation of a nucleic acid into a protein. Proteins may be expressed and remain intracellular, become a component of the cell surface membrane or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA and stop codons. The term "control sequences" is intended to include, at a minimum, components whose presence can influence expression and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Growth factor: Proteins capable of stimulating cellular proliferation and cellular differentiation. Examples of growth factors include transforming growth factor beta (TGF-β), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF-9), basic fibroblast growth factor (bFGF or FGF2), epidermal growth factor (EGF), hepatocyte growth factor (HGF) and the like. In some examples, a growth factor or portion thereof sufficient to bind to a growth factor receptor is part of a hetero-bifunctional ligand.

Heterologous: With reference to a molecule, such as a receptor-binding agent (for example an internalizing or target receptor-binding agent) or a linker, "heterologous" refers to molecules that are not normally associated with each other, for example as a single molecule. Thus, a "heterologous" linker is a linker attached to another molecule that the linker is usually not found in association with in nature, such as in a wild-type molecule. For example, if a receptor binding agent (such as an internalizing or target receptor-binding agent) is a polysaccharide (such as a sulfated polysaccharide, for example sulfated dextran or Fucoidan) a heterologous linker would not be the same polysaccharide (such as the same sulfated polysaccharide). In another example, an internalizing receptor-binding agent is attached to a heterologous linker and a heterologous target receptor-binding agent to which it is not naturally attached. In another example, a target receptor-binding agent is attached to a heterologous linker and a heterologous internalizing receptor-binding agent to which it is not naturally attached.

Hetero-bifunctional ligand: A molecule that contains at least a first and second non-identical moieties (for example heterologous molecules), wherein each of the moieties is capable of specifically binding a different receptor, for example an internalizing receptor and a target receptor. Hence, each moiety has specificity for a different receptor so that the first moiety specifically binds a first receptor but not the second receptor and the second moiety binds the second receptor but not the first receptor. In some examples, a hetero-bifunctional ligand includes a linker heterologous to the internalizing receptor-binding agent and the target receptor-binding agent. In some examples, a hetero-bifunctional ligand includes a target receptor-binding agent heterologous to the internalizing receptor-binding agent and the linker. In some examples, a hetero-bifunctional ligand includes an internalizing receptor-binding agent heterologous to the target receptor-binding agent and the linker.

Hormone: A classification of small molecules that carries a signal from one cell (or group of cells) to another. Examples of hormones include amine-tryptophans, such as melatonin (n-acetyl-5-methoxytryptamine) and serotonin; amine-tyrosines, such as thyroxine (thyroid hormone), triiodothyronine (thyroid hormone), epinephrine (adrenaline), norepinephrine (noradrenaline) and dopamine; peptide hormones, such as antimullerian hormone (mullerian inhibiting factor), adiponectin, adrenocorticotropic hormone (orticotropin), angiotensinogen and angiotensin, antidiuretic hormone (vasopressin, arginine vasopressin), atrial-natriuretic peptide atriopeptin), calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, inhibin, insulin, insulin-like growth factor (somatomedin), leptin, luteinizing hormone, melanocyte stimulating hormone, oxytocin, parathyroid hormone, prolactin, relaxin, secretin, somatostatin, thrombopoietin, thyroid-stimulating hormone and thyrotropin-releasing hormone; steroids, such as cortisol, aldosterone, testosterone, dehydroepiandrosterone, androstenedione, dihydrotestosterone, estradiol, estrone, estriol, progesterone and calcitriol (vitamin d3); and eicosanoids, such as prostaglandins, leukotrienes, prostacyclin and thromboxane, among others. In some examples, a hetero-bifunctional ligand includes a hormone or portion thereof sufficient to bind a hormone receptor.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Inhibiting or treating a disease: Inhibiting the full development of a disease or condition, for example, in a subject who is at risk for a disease such as cancer or a viral infection (for example, an HIV infection). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject or by other parameters well known in the art that are specific to the particular disease. A "prophylactic" treatment is a treatment administered to a subject who does not exhibit signs of a disease or exhibits only early signs for the purpose of decreasing the risk of developing pathology.

Internalizing receptor: A cell surface receptor that is internalized into a cell upon binding of a specific ligand to the receptor. Examples of internalizing receptors include without limitation scavenger receptors, LDL receptors, heat shock protein receptors and transferrin receptors among others.

Internalizing receptor ligand: A ligand capable of specifically binding to and inducing the internalization of a specific internalizing receptor. Examples of internalizing receptor ligands include ligands for scavenger receptors such as acetylated-LDL, oxidized-LDL, sulfated polysaccharides, maleylated proteins, polyguanylic acid, high density lipoprotein (HDL) oligonucleotides; among others, ligands for LDL receptors, such as LDL, ligands for heat shock protein receptors, such as heat shock proteins; and ligands for transferrin receptors, such as transferrin and the like. In some embodiments, an internalizing receptor ligand is an antibody.

Internalization (of a receptor): The act of a receptor moving from the outer cell surface of a cell to the interior of the cell, such as into the cytoplasm, the nucleus or a cytoplasmic organelle or vesicle. In some examples, internalization of the receptor is induced by the binding of a hetero-bifunctional ligand.

Low Density Lipoprotein (LDL) Receptor: A receptor that mediates the endocytosis (internalization) of cholesterol-rich LDL. It is a cell-surface receptor that recognizes the apoprotein B100 which is embedded in the phospholipid outer layer of LDL particles. An exemplary human (LDL) receptor nucleic acid sequence can be found on GENBANK® at accession number NM_000527 incorporated herein by reference as available Jan. 24, 2008. Exemplary human LDL receptor amino acid sequences can be found on GENBANK® at accession numbers AAA56833, AAP72971, AAF24515, AAM56036, AAB22609, AH004493, AAB30338 and AAB30152 incorporated herein by reference as available Jan. 24, 2008.

Ligand: Any molecule which specifically binds a receptor, such as an internalizing receptor or a target receptor and includes, inter alia, antibodies that specifically bind an internalizing receptor or a target receptor. In alternative embodiments, the ligand is a protein or a small molecule (for example a molecule with a molecular weight less than 10 kiloDaltons, (kD) that specifically binds the receptor of interest).

Linker: A compound or moiety that acts as a molecular bridge to operably link two different molecules, wherein one portion of the linker is operably linked to a first molecule and wherein another portion of the linker is operably linked to a second molecule. In some examples a linker is a polypeptide. The two different molecules can be linked to the linker in a step-wise manner. There are no particular size or content limitations for the linker so long as it can fulfill its purpose as a molecular bridge. Linkers are known to those skilled in the art to include, but are not limited to, chemical chains, chemical compounds, carbohydrate chains, peptides, haptens and the like. The linkers can include, but are not limited to, homobifunctional linkers and hetero-bifunctional linkers. Hetero-bifunctional linkers, well known to those skilled in the art, contain one end having a first reactive functionality to specifically link a first molecule and an opposite end having a second reactive functionality to specifically link to a second molecule. Depending on such factors as the molecules to be linked and the conditions in which the method of detection is performed, the linker can vary in length and composition for optimizing such properties as flexibility, stability and resistance to certain chemical and/or temperature parameters. In particular examples, a linker is the combination of streptavidin or avidin and biotin.

Nucleic acid: A polymer composed of nucleotide units (ribonucleotides, deoxyribonucleotides, related naturally occurring structural variants and synthetic non-naturally occurring analogs thereof or combinations thereof) linked via phosphodiester bonds, related naturally occurring structural variants and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs) and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, for example a "recombinant polypeptide." A recombinant nucleic acid may serve a non-coding function (for example a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA and TFASTA in the Wisconsin Genetics Software Package, Genetics Computer Group, 575 Science Dr., Madison, Wis.) or by manual alignment and visual inspection (see, for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10) and weighted end gaps. PILEUP can be obtained from the GCG sequence analysis software package, for example, version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information. The BLASTN program (for nucleotide sequences) uses as defaults a word length (W) of 11, alignments (B) of 50, expectation (E) of 10, M=5, N=−4 and a comparison of both strands. The BLASTP program uses as defaults a word length (W) of 3 and expectation (E) of 10 and the BLOSUM62 scoring matrix (see Henikoff & Henikoff, *Proc. Natl. Acad. Sci. USA* 89:10915, 1989).

Nucleotide: The fundamental unit of nucleic acid molecules. A nucleotide includes a nitrogen-containing base attached to a pentose monosaccharide with one, two or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil and 2,6-diaminopurine 2'-deoxyguanosine amongst others.

Examples of modified sugar moieties, which may be used to modify nucleotides at any position on its structure, include, but are not limited to arabinose, 2-fluoroarabinose, xylose and hexose or a modified component of the phosphate backbone, such as phosphorothioate, a phosphorodithioate, a phosphoramidothioate, a phosphoramidate, a phosphordiamidate, a methylphosphonate or an alkyl phosphotriester or analog thereof.

Neuropeptide: Peptides released by neurons in the mammalian brain that specifically bind a neuropeptide receptor. Examples of neuropeptides include α-melanocyte-stimulating hormone (α-MSH), galanin-like peptide, a cocaine-and-amphetamine-regulated transcript (CART), neuropeptide Y, agouti-related peptide (AGRP), β-endorphin, dynorphin, enkephalin, galanin, ghrelin, growth-hormone releasing hormone, neurotensin, neuromedin U, somatostatin, galanin, enkephalin cholecystokinin, vasoactive intestinal polypeptide (VIP) and substance P among others. In some examples, a neuropeptide or portion thereof sufficient to bind to a neuropeptide receptor is part of a hetero-bifunctional ligand.

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In other examples, a molecule is "operably linked" to another molecule when the two molecules are connected by a linker, for example a linker connecting to specific binding agent to form a hetero-bifunctional ligand, such as those disclosed herein.

Pharmaceutical agent: A chemical compound or composition capable of inducing a desired therapeutic or prophylactic effect when properly administered to a subject or a cell. In some embodiments, a pharmaceutical agent is a hetero-bifunctional ligand that includes an internalizing receptor-binding agent linked to a target receptor-binding agent, wherein the internalizing receptor binding agent and target receptor binding agent are different agents.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives and pH buffering agents and the like, for example sodium acetate or sorbitan monolaurate.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

A receptor peptide such as a target receptor peptide or a scavenger receptor peptide is a series of contiguous amino acid residues from a receptor peptide protein, such as a fragment of receptor peptide from about 10 to about 25 amino acids in length, such as about 11 to about 20 amino acid in length, such as about 12 consecutive amino acids of an receptor peptide protein. In some examples, an immunogenic composition for use in producing an antibody that specifically binds a receptor, such as a target receptor or an internalizing receptor, includes a receptor peptide.

Polypeptide: Any chain of amino acids, regardless of length or post-translational modification (for example glycosylation or phosphorylation). In one embodiment, the polypeptide is receptor polypeptide. A "residue" refers to an amino acid or amino acid mimetic incorporated in a polypeptide by an amide bond or amide bond mimetic. A polypeptide has an amino terminal (N-terminal) end and a carboxy terminal end.

Scavenger receptors: A group of receptors that recognize and internalize into a cell a large array of macromolecules having a negative charge as well as modified lipoproteins such as acylated low density lipoprotein (Ac-LDL). These scavenger receptors are expressed on various cell types, such as macrophages and endothelial cells and include CD36 (also known as scavenger receptor class B type I or SR-BI), lectin oxidized LDL receptor-1 (LOX-1), collectin placenta 1 (CL-P1), FEEL-1/Stabilin-1/CLEVER-1 and scavenger receptor expressed by endothelial cells I (SREC-I) and II (SREC-II). Scavenger receptors can bind a vast array of structurally diverse ligands including LDL, high density lipoprotein (HDL), apoptotic cells, bacteria, components of the extracellular matrix, some oligonucleotides and some sulfated polysaccharides (for a review of scavenger receptors see Adachi and Tsujimoto, *Progress in Lipid Research* 45:379-404, 2006).

Binding of some ligands to the extracellular domain of scavenger receptors induces the endocytosis (internalization) of the receptor and the ligand bound to the receptor. Scavenger receptors can be used to internalize biologically active agents such as chemotherapeutics and antibiotics by constructing ligands that include a scavenger receptor-binding moiety linked to a drug or other biologically active agent (see, for example, Mukhopadhyay et al., *Biochem J.* 284: 237-241, 1992; Majumdar and Basu *Antimicrob Agents Chemother.* 35(1): 135-140, 1991; and Brasseur et al., *Photochem Photobiol.* 69(3):345-52, 1999).

Scavenger receptor-binding agent: An agent that specifically binds to a scavenger receptor. In one example, a scavenger receptor-binding agent is an antibody, such as a monoclonal antibody, that specifically binds to a scavenger receptor. In other embodiments, a scavenger receptor-binding agent is a ligand, such as a small molecule ligand, for the scavenger receptor. In some embodiments, a scavenger receptor-binding agent is a component of a hetero-bifunctional ligand, such as a hetero-bifunctional ligand disclosed herein.

Specific binding agent: An agent that binds substantially only to a defined target. Thus, a receptor specific binding agent is an agent that binds substantially a specific receptor or fragment thereof. In some examples, the specific binding agent is a monoclonal or polyclonal antibody that specifically binds a specific receptor or antigenic fragment thereof. In other examples, the specific binding agent is a small molecule that specifically binds the specific receptor and for example does not bind any other receptor.

In some embodiments, a specific binding agent is a target receptor specific binding agent the specifically binds a target receptor. In some embodiments, a specific binding agent is an internalizing receptor specific binding agent the specifically binds an internalizing receptor.

The term "specifically binds or specific binding" refers, with respect to a specific target receptor, to the preferential association of an antibody or other ligand, in whole or part, with a cell or tissue bearing that specific receptor and not to cells or tissues lacking a detectable amount of that specific receptor. It is recognized that a certain degree of non-specific interaction may occur between a molecule and a non-target cell or tissue. Specific binding may be distinguished as mediated through specific recognition of the specific receptor. Specific binding typically results in greater than 2-fold, such as greater than 5-fold, greater than 10-fold or greater than 100-fold increase in amount of bound antibody or other ligand (per unit time) to a cell or tissue bearing the specific target receptor as compared to a cell or tissue lacking the specific target receptor respectively.

Target receptor: A pre-selected cell surface receptor that is specifically bound by a target ligand. Internalization of target receptors can be accomplished using a hetero-bifunctional ligand, such as a hetero-bifunctional ligand disclosed herein. Examples of target receptors include neuropilin-1, neuropilin-2, a vascular endothelial growth factor (VEGF) receptor, such as vascular endothelial growth factor receptor (VEGFR)-1, VEGFR-2, VEGFR-3, an interleukin (IL) receptor, such as IL-3 receptor, IL-8 receptor, IL-6 receptor, gp130, an interferon (IFN) receptor. Other examples of a target receptors are a receptor tyrosine kinase (RTK) receptors, such as a RTK class I receptor, for example an epidermal growth factor (EGF) receptor family receptor, for example as HER2/neu, Her 3 or Her 4; a RTK class II receptor, such as an insulin receptor family receptor, for example Insulin-like growth factor (IGF)-1 receptor; a RTK class III receptor, such as a platelet-derived growth factor (PDGF) receptor family receptor, for example such as a platelet-derived growth factor receptor (PDGFR); a RTK class IV receptor, such as a fibroblast growth factor (FGF) receptor family member, for example fibroblast growth factor receptor (FGFR)1, FGFR2 or FGFR3; a RTK class VI receptor, such as a hepatocyte growth factor (HGF) receptor family member; a RTK class VII receptor, such as a TRK receptor family member, for example TrkA, TrkB or TrkC; a RTK class VIII receptor, such as an EPH receptor family member, for example Eph; a RTK class IX receptor, such as an AXL receptor family member; a RTK class X receptor, such as a LTK receptor family member; a RTK class XI receptor, such as a TIE receptor family member, for example Tie-1 or Tie-2; a RTK class XII receptor, such as a RAR-related orphan receptor (ROR) receptor family member; a RTK class XIII receptor, such as a discoidin domain receptor (DDR) receptor family member; a RTK class XIV receptor, such as rearranged during transfection (RET) receptor family member, for example RET; a RTK class XV receptor, such as a KLG receptor family member; a RTK class XVI receptor, such as a RYK receptor family member; and a RTK class XVII receptor, such as a muscle specific kinase (MuSK) receptor family member. Further examples of target receptors include chemokine receptors, such as a CXC chemokine receptor family member, for example CXCR1, CXCR2, CXCR3, CXCR4, CXCR5, CXCR6 or CXCR7; a CC chemokine receptor family member, for example CCR1, CCR2, CCR3, CCR4, CCR5, CCR6, CCR7, CCR8, CCR9, CCR10 or CCR11; a XC chemokine receptor, for example XCR1; or a CX3C chemokine receptor, for example CX3CR1 or the like. Cell-cell interaction receptors can also be target receptors and for example include VE-cadherin, N-cadherin, intercellular adhesion molecule 1 (ICAM-1), connexin, occludin, CD148 or the like; an integrin family receptor, such as integrin alpha5beta1, alpha1beta1, alpha2beta1, alphavbeta3 or alphavbeta5, CD61 (fibrinogen receptor). Other examples include neuropeptide receptors, such as an endothelin receptor, a G-protein coupled receptor, an adrenergic receptor, an olfactory receptor, a low affinity nerve growth factor receptor, a N-methyl-D-aspartic acid (NMDA) receptor as well as toll-like receptors (TLR), such as TLR 1, TLR 2, TLR 3, TLR 4, TLR 5, TLR 6, TLR 7, TLR 8, TLR 9, TLR 10, TLR 11, TLR 12 or TLR 13 or T cell receptor among others.

Target receptor-binding agent: An agent that is selected to specifically binds to a target receptor. In one example, a target receptor-binding agent is an antibody, such as a monoclonal antibody, that specifically binds to a target receptor. In other embodiments, a target receptor-binding agent is a ligand, such as a small molecule ligand, for the target receptor. In some embodiments, a target receptor-binding agent is a component of a hetero-bifunctional ligand, such as a hetero-bifunctional ligand disclosed herein.

Targeting moiety: A portion of a chimeric molecule intended to provide the molecule with the ability to bind specifically to a pre-selected target receptor. A "ligand" is an example of a targeting molecule specific for a target receptor that serves as a "targeting moiety."

Therapeutically effective amount: A quantity of a specific substance sufficient to achieve a desired effect in a subject being treated. For instance, this can be the amount necessary to inhibit or suppress growth of a tumor or the amount necessary to inhibit a viral infection, such as an HIV infection. In one embodiment, a therapeutically effective amount is the amount necessary to eliminate a tumor. When administered to a subject, a dosage will generally be used that will achieve target tissue concentrations shown to achieve a desired in vitro effect.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors and introduction of DNA by electroporation, lipofection and particle gun acceleration.

Vascular endothelial growth factor A (VEGFA): A growth factor involved in angiogenesis. Exemplary human VEGFA nucleic acid sequences can be found on GENBANK® at accession numbers NM_001025370, NM_001025367, NM_005429, BC011177, NM_001033756 and NM_001025368 incorporated herein by reference as available Jan. 24, 2008. Exemplary human VEGFA amino acid sequences can be found on GENBANK® at accession numbers AAH11177 and AAH65522 incorporated herein by reference as available Jan. 24, 2008.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: Microscopic infectious organism that reproduces inside living cells. A virus consists essentially of a core of a single nucleic acid surrounded by a protein coat and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine or responding to a cytokine, when the uninfected cell does not normally do so. Viral infection refers to the infection of a subject, a cell or even a cell within a subject with a virus.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-I and HIV-II), simian immunodeficiency virus (SIV) and feline immunodeficiency virus (FIV).

HIV-I is a retrovirus that causes immunosuppression in humans (HIV disease) and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

II. Description of Several Embodiments

Internalization of receptors can attenuate ligand-induced signaling. In some examples, after a ligand binds to its receptor on the cell membrane, the receptor is internalized. This sequestration of the receptor away from the cell surface often results in ligand desensitization and protection from prolonged or excessive signaling. In the case of shared-type receptors, for example when the same cell surface molecule is a receptor for distinct ligands, internalization of the receptor induced by one ligand can serve to block receptor-binding by the second ligand.

As disclosed herein, selectively induced internalization of a surface receptor can be used to dampen the biological effects that are dependent upon the cell surface residence of a particular target receptor, for example using a hetero-bifunctional ligand disclosed herein. Typically, inhibitors of receptor signaling, such as blocking antibodies, inhibitory receptor ligands or inhibitory small molecules, are only effective in inhibiting a receptor if they can displace the natural ligand for a receptor, for example by having higher affinity for the receptor than the natural ligand. In contrast, the hetero-bifunctional ligands disclosed herein are effective because they are able to promote target receptor internalization and remove a target receptor from possible interaction with its natural ligand. Thus, one advantageous aspect of this new class of inhibitors (hetero-bifunctional ligands) is that is not necessary that they compete with the binding affinity of the natural ligand. Furthermore, because the disclosed hetero-bifunctional ligand binds to two distinct receptors on the surface of a cell (a target receptor and an internalizing receptor) their cell targeting specificity is enhanced. For example, a specific cell type can be targeted by a specific target and internalizing receptor pair. For example, if the desired target receptor is NRP1 on the surface of endothelial cells, for example to inhibit angiogenesis, a hetero-bifunctional ligand is constructed that contains a target receptor-binding agent specific for the target receptor NRP1 and an internalizing receptor-binding agent, such as a ligand specific for the endothelial cell specific scavenger receptor, SREC-I. Such a hetero-bifunctional ligand can be used to selectively target NRP1 on endothelial cells, to the exclusion of other NRP1-expressing cell types that do not express SREC-I, for example to inhibit endothelial cell mediated angiogenesis. Using an appropriately paired target receptor-binding agent and internalizing receptor-binding agent, a hetero-bifunctional ligand can be constructed to specifically target any target receptor on virtually any cell-type.

Hetero-Bifunctional Ligands

Disclosed herein are hetero-bifunctional ligands for use in inducing internalization of a target receptor. The disclosed hetero-bifunctional ligands include a target receptor-binding agent that specifically binds the target receptor, linked to an internalizing receptor-binding agent that specifically binds to an internalizing receptor. The target receptor-binding agent and internalizing receptor-binding agent are not identical and in some cases do not bind the same receptor. A linker can be used to link the target receptor-binding agent to the internalizing receptor-binding agent so long as the linker is of sufficient length to allow the internalizing receptor-binding agent and target receptor-binding agent to bind to the target receptor and the internalizing receptor, respectively, on the surface of a cell. The binding of the hetero-bifunctional ligand to the internalizing receptor induces internalization of the internalizing receptor and through the linker the internalization of the target receptor bound by the hetero-bifunctional ligand. In the case of a multi-subunit receptor, the target receptor can be a portion of the multi-subunit receptor sufficient to produce internalization and result in a loss of signal propagation through the remaining portion of the receptor on the surface of the cell. Thus, the disclosed hetero-bifunctional ligands are capable of effectively hiding the target receptor from external stimulation, which inhibits signaling through the target receptor. The disclosed hetero-bifunctional ligands can be used to target any cell-surface target receptor, such as a target receptor of interest, using an appropriate hetero-bifunctional ligand that includes a target receptor-binding agent that is specific for the target receptor of interest.

In some embodiments, a target receptor-binding agent is a ligand for a receptor tyrosine kinase (RTK) receptor, such as a RTK class I receptor. For example the target receptor-binding agent can be agent that specifically binds an epidermal growth factor (EGF) receptor family receptor, such as HER2/neu, Her 3 or Her 4; a RTK class II receptor, such as an insulin receptor family receptor, for example Insulin-like growth factor (IGF)-1 receptor; a RTK class III receptor, such as a platelet-derived growth factor (PDGF) receptor family receptor, for example a platelet-derived growth factor receptor (PDGFR); a RTK class IV receptor, such as a fibroblast growth factor (FGF) receptor family member, for example fibroblast growth factor receptor (FGFR)1, FGFR2 or FGFR3; a RTK class VI receptor, such as a hepatocyte growth factor (HGF) receptor family member; a RTK class VII receptor, such as a TRK receptor family member, for example TrkA, TrkB or TrkC; a RTK class VIII receptor, such as an EPH receptor family member, for example Eph; a RTK class IX receptor, such as an AXL receptor family member; a RTK class X receptor, such as a LTK receptor family member; a RTK class XI receptor, such as a TIE receptor family member, for example Tie-1 or Tie-2; a RTK class XII receptor, such as a RAR-related orphan receptor (ROR) receptor family member; a RTK class XIII receptor, such as a discoidin domain receptor (DDR) receptor family member; a RTK class XIV receptor, such as rearranged during transfection (RET) receptor family member, for example RET; a RTK class XV receptor, such as a KLG receptor family member; a RTK class XVI receptor, such as a RYK receptor family member; a RTK class XVII receptor, such as a muscle specific kinase (MuSK) receptor family member or the like.

The target receptor can be chemokine receptor, such as a CXC chemokine receptor family member, for example CXCR1, CXCR2, CXCR3, CXCR4, CXCR5, CXCR6 or CXCR7; a CC chemokine receptor family member, for example CCR1, CCR2, CCR3, CCR4, CCR5, CCR6, CCR7, CCR8, CCR9, CCR10 or CCR11; a XC chemokine receptor, for example XCR1; or a CX3C chemokine receptor, for example CX3CR1. In some embodiments, a chemokine specific for that receptor can be used to construct a hetero-bifunctional ligand. Thus, in some embodiments, the target receptor-binding agent is a chemokine or a portion thereof that specifically binds the chemokine receptor. Examples of chemokines of use include chemokines that bind to CCR family receptors, such as the CCL chemokines, for example CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27 and CCL28; chemokines that bind to CXCR family receptors, such as CXCL chemokines, for example CXCL1, CXCL2, CXCL3, CXCL4, CXCL5, CXCL6, CXCL7, CXCL8, CXCL9, CXCL10, CXCL11, CXCL12, CXCL13, CXCL14, CXCL15 and CXCL16; chemokines that bind to XCR family receptors, such as the XCL chemokines, for example XCL1 and XCL2; and chemokines that bind to CX3CR family receptors, such as the CX3CL chemokines, for example CX3CL1.

The target receptor can be an interleukin receptor, such as IL-1R1 (see, for example, GENBANK® accession No. M27492), IL-1R2 (see, for example, GENBANK® accession No. X59770), IL-1R1 (see, for example, GENBANK® accession No. M27492), IL-1R2 (see, for example, GENBANK® accession No. X59770), IL-2RA see, for example, GENBANK® accession No. (see, for example, GENBANK® accession No. X01057), IL-2RB (see, for example, GENBANK® accession No. M26062), IL-3RA (see, for example, GENBANK® accession No. M74782), IL-4R (see, for example, GENBANK® accession No. X52425), IL-5RA (see, for example, GENBANK® accession No. M96652), IL-6R (see, for example, GENBANK® accession No. X12830), IL-7R (see, for example, GENBANK® accession No. M29696), IL-8RA (see, for example, GENBANK® accession No. U11870), IL-8RB (see, for example, GENBANK® accession No. U11869), IL-9R (see, for example, GENBANK® accession No. M84747), IL-10RA (see, for example, GENBANK® accession No. U00672), IL-10RB (see, for example, GENBANK® accession No. U08988), IL-11RA (see, for example, GENBANK® accession No. Z38102), IL-11RB, IL-12RB1 (see, for example, GENBANK® accession No. U03187), IL-12RB2, (see, for example, GENBANK® accession No. U64198), IL-13RA1 (see, for example, GENBANK® accession No. U62858), IL-13RA2 (see, for example, GENBANK® accession No. X95302), IL-15RA (see, for example, GENBANK® accession No. U31628), IL-15RB, IL-17RA (see, for example, GENBANK® accession No. U58917), IL-17RB (see, for example, GENBANK® accession No. AF212365), IL-17RC (see, for example, GENBANK® accession No. BC006411), IL-17RD (see, for example, GENBANK® accession No. AF494208) IL-17RE (see, for example, GENBANK® accession No. AF458069), IL-18BP (see, for example, GENBANK® accession No. AF110798), IL-18R1 (see, for example, GENBANK® accession No. U43672), IL-20RA (see, for example, GENBANK® accession No. AF184971), IL-20RB (see, for example, GENBANK® accession No. BC033292), IL-21R (see, for example, GENBANK® accession No. AF254067), IL-22RA1 (see, for example, GENBANK® accession No. AF286095), IL-22RA2 (see, for example, GENBANK® accession No. AY044429), IL-27RA (see, for example, GENBANK® accession No. AF053004), IL-28RA (see, for example, GENBANK® accession No. AY129153), IL-31RA (see, for example, GENBANK® accession No. AY499339), all of which are incorporated herein by reference as available Jan. 24, 2008.

An interleukin that specifically binds that receptor can be used to construct a hetero-bifunctional ligand. Thus, in some embodiments, the target receptor-binding agent is an interleukin or a portion thereof that specifically binds the interleukin receptor. Examples of interleukins include IL-1α (see, for example, GENBANK® accession No. M28983), IL-1α (see, for example, GENBANK® accession No. M15330), IL-2 (see, for example, GENBANK® accession No. U25676), IL-3 (see, for example, GENBANK® accession No. M14743), IL-4 (see, for example, GENBANK® accession No. M23442), IL-5 (see, for example, GENBANK® accession No. X04688), IL-6 (see, for example, GENBANK® accession No. M18403), IL-7 (see, for example, GENBANK® accession No. J04156), IL-8 (see, for example, GENBANK® accession No. Y00787), IL-9 (see, for example, GENBANK® accession No. S63356), IL-10 (see, for example, GENBANK® accession No. M57627), IL-11 (see, for example, GENBANK® accession No. X583770), IL-12 (see, for example, GENBANK® accession No. X58377 or M65290), IL-13 (see, for example, GENBANK® accession No. U31120), IL-14, IL-15 (see, for example, GENBANK® accession No. U144070), IL-16 (see, for example, GENBANK® accession No. U82972), IL-17 (see, for example, GENBANK® accession No. U32659, AF184969, AF152099, AY078238 or AF384857), IL-18 (see, for example, GENBANK® accession No. U90434), IL-19 (see, for example, GENBANK® accession No. AF192498), IL-20 (see, for example, GENBANK® accession No. AF224266), IL-21 (see, for example, GENBANK® accession No. AF254069), IL-22 (see, for example, GENBANK® accession No. AF279437), IL-23, IL-24 (see, for example, GENBANK® accession No. U16261), IL-25 (see, for example, GENBANK® accession No. AF305200), IL-26 (see, for example, GENBANK® accession No. AJ251549), IL-27 (see, for example, GENBANK® accession No. AY099296), IL-28 (see, for example, GENBANK® accession Nos. AY129148 or AY129149), IL-29 (see, for example, GENBANK® accession No. AY129150), IL-30, IL-31 (see, for example, GENBANK® accession No. AY499343) or IL-32 (see, for example, GENBANK® accession No. M59807) all of which are incorporated herein by reference as available Jan. 24, 2008.

If the target receptor is an interferon receptor, an interferon that specifically binds that receptor can be used to construct a hetero-bifunctional ligand. Thus, in some embodiments, the target receptor-binding agent is an interferon or a portion thereof that specifically binds the interferon receptor. Examples of interferons useful in producing a disclosed hetero-bifunctional ligand include IFN-α, IFN-β and IFN-γ.

If the target receptor is a growth factor receptor, a growth factor that specifically binds that receptor can be used to construct a hetero-bifunctional ligand. Thus, in some embodiments, the target receptor-binding agent is a growth factor or a portion thereof that specifically binds the growth factor receptor. Examples of growth factors of use include transforming growth factor beta (TGF-β, see, for example, GENBANK® Accession No. AAA36735), granulocyte-colony stimulating factor (G-CSF, see, for example, GENBANK® Accession Nos. CAA27291, CAA27290 or CAA01319), granulocyte-macrophage colony stimulating factor (GM-CSF, see, for example, GENBANK® Accession No. AAA52578), nerve growth factor (NGF, see, for example, GENBANK® Accession Nos. AAI26151, AAI26149, AAH32517 or CAA37703), neurotrophins, platelet-derived growth factor (PDGF), erythropoietin (EPO, see, for example, GENBANK® Accession Nos. AAF23134, AAF23132, AAF17572 or AAF23133), thrombopoietin (TPO, see, for example, GENBANK® Accession No. AAB33390), myostatin (GDF-8, see, for example, GENBANK® Accession No. AAB86694), growth differentiation factor-9 (GDF9, see, for example, GENBANK® Accession Nos. AAH96229, AAH96228, AAH96231 or AAH96230), basic fibroblast growth factor (bFGF, see, for example, GENBANK® Accession Nos. AAB21432 or FGF2, (see, for example, GENBANK® Accession No. NP_001997), epidermal growth factor (EGF, see, for example, GENBANK® Accession No. AAS83395), hepatocyte growth factor (HGF, see, for example, GENBANK® Accession Nos. AAA64297, AAA64239 or AAA52649), vascular endothelial growth factor (VEGF, see, for example, GENBANK® Accession Nos. AAA35789, CAM28207, CAC19515, CAC19513, AAP86646, ABB58912, AAK95847, CAA44447, CAC19516 or CAC19512), such as VEGF-A and the like incorporated herein by reference as available Jan. 24, 2008.

If the target receptor is a hormone receptor, a hormone that specifically binds that receptor can be used to construct a hetero-bifunctional ligand. Thus, in some embodiments, the target receptor-binding agent is a hormone or portion thereof that specifically binds the hormone receptor. Examples of hormones of use include amine-tryptophans, such as melatonin (n-acetyl-5-methoxytryptamine) and serotonin; amine-tyrosines, such as thyroxine (thyroid hormone), triiodothyronine (thyroid hormone), epinephrine (adrenaline), norepinephrine (noradrenaline) and dopamine; peptide hormones, such as antimullerian hormone (mullerian inhibiting factor), adiponectin, adrenocorticotropic hormone (orticotropin), angiotensinogen, angiotensin antidiuretic hormone (vasopressin, arginine vasopressin), atrial-natriuretic peptide atriopeptin), calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, inhibin, insulin, insulin-like growth factor (somatomedin), leptin, luteinizing hormone, melanocyte stimulating hormone, oxytocin, parathyroid hormone, prolactin, relaxin, secretin, somatostatin, thrombopoietin, thyroid-stimulating hormone and thyrotropin-releasing hormone; steroids, such as cortisol, aldosterone, testosterone, dehydroepiandrosterone, androstenedione, dihydrotestosterone, estradiol, estrone, estriol, progesterone and calcitriol (vitamin D3); and eicosanoids, such as prostaglandins, leukotrienes, prostacyclin and thromboxane, among others.

If the target receptor is a neuropeptide receptor, a neuropeptide or portion thereof that specifically binds that receptor can be used to construct a hetero-bifunctional ligand. Thus, in some embodiments, the target receptor-binding agent is a neuropeptide or portion thereof that specifically binds the neuropeptide receptor. Examples of neuropeptides of use include α-melanocyte-stimulating hormone (α-MSH), galanin-like peptide, a cocaine-and-amphetamine-regulated transcript (CART), neuropeptide Y, agouti-related peptide (AGRP), β-endorphin, dynorphin, enkephalin, galanin, ghrelin, growth-hormone releasing hormone, neurotensin, neuromedin U, somatostatin, galanin, enkephalin cholecystokinin, VIP and substance P among others.

In some embodiments, a disclosed hetero-bifunctional ligand has a target receptor-binding agent that specifically binds a cell-cell interaction receptor, such as VE-cadherin, N-cadherin, intercellular adhesion molecule 1 (ICAM-1), connexin, occludin, CD148 or the like, an integrin family receptor, such as integrin alpha5beta1, integrin alpha1beta1, integrin alpha2beta1, integrin alphavbeta3 or integrin alphavbeta5, CD61 (fibrinogen receptor), a neuropeptide receptor, an endothelin receptor, a G-protein coupled receptor, an adrenergic receptor, an olfactory receptor, a low affinity nerve growth factor receptor, a N-methyl-D-aspartic acid (NMDA) receptor, a toll-like receptor (TLR), such as TLR 1, TLR 2, TLR 3, TLR 4, TLR 5, TLR 6, TLR 7, TLR 8, TLR 9, TLR 10, TLR 11, TLR 12 or TLR 13 or T cell receptor among others.

Other examples of receptor ligands that can be used to prepare a hetero-bifunctional ligand include tumor necrosis factors, such as TNF-α and TNF-β macrophage inflammatory proteins, such as MIP-1α and MIP-1β and transforming growth factors, such as TGF-β.

In some embodiments, the target receptor-binding agent comprises an antibody that specifically binds the target receptor, for example a monoclonal or polyclonal antibody. In some embodiments, the antibody is a humanized antibody. Exemplary procedures for producing antibodies, such as a polyclonal, monoclonal, and/or humanized antibodies are set forth below and are known in the art. In some embodiments, the target receptor-binding agent includes a small molecule that specifically binds the target receptor, for example a small molecule ligand that binds the target receptor. In some embodiments, the hetero-bifunctional ligand includes a target receptor ligand, such as a cytokine, a chemokine, a growth factor, a hormone, a neuropeptide or a portion thereof that specifically binds the target receptor. In some embodiments, a hetero-bifunctional ligand includes a target receptor-binding agent heterologous to the internalizing receptor-binding agent and the linker.

In some examples, the target receptor-binding agent is an oligonucleotide, such as polyguanosine, phosphorothioate oligodeoxyguanosine, oligodeoxyguanosine oligo 2'-deoxyguanosine 5'-monophosphate among others. In some embodiments, the oligonucleotide is between about 6 nucleotides and about 100 nucleotide in length, such as about 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length, for example between about 6 to about 15, about 10 to about 20, about 15 to about 25, about 20 to about 30, about 25 to about 35, about 30 to about 40, about 35 to about 45, about 40 to about 50, about 45 to about 55, about 50 to about 60, about 55 to about 65, about 60 to about 70, about 65 to about 75, about 70 to about 80, about 75 to about 85, about 80 to about 90, about 85 to about 95 or about 90 to 100 nucleotides in length.

The disclosed hetero-bifunctional ligands also include an internalizing receptor-binding agent that specifically binds to an internalizing receptor. Internalizing receptors are cell surface receptors that are induced to internalize upon binding of specific ligands. Examples of internalizing receptors include without limitation scavenger receptors, LDL receptors, heat shock protein receptors and transferrin receptors, among others. Thus, the disclosed hetero-bifunctional ligands include an internalizing receptor ligand or portion thereof specific for the internalizing receptor and capable of inducing the internalization of the internalizing receptor, such as ligands for scavenger receptors, for example acetylated-LDL, oxidized-LDL, sulfated polysaccharides, maleylated proteins, polyguanylic acids, HDL oligonucleotides, such as polyguanosine (poly(G)), or derivatives thereof; ligands for LDL receptors, for example LDL; ligands for a heat shock protein receptors for example heat shock proteins or portions thereof specific for a heat shock protein receptors; ligands for transferrin receptors, such as transferrin or portions thereof specific for a transferrin receptors and the like. In some embodiments, a hetero-bifunctional ligand includes an internalizing receptor-binding agent heterologous to the target receptor-binding agent and the linker. In some examples, the internalizing receptor-binding agent is an oligonucleotide, such as polyguanosine, phosphorothioate oligodeoxyguanosine, oligodeoxyguanosine oligo 2'-deoxyguanosine 5'-monophosphate among others. In some embodiments, the oligonucleotide is between about 6 nucleotides and about 100 nucleotide in length, such as about 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length, for example between about 6 to about 15, about 10 to about 20, about 15 to about 25, about 20 to about 30, about 25 to about 35, about 30 to about 40, about 35 to about 45, about 40 to about 50, about 45 to about 55, about 50 to about 60, about 55 to about 65, about 60 to about 70, about 65 to about 75, about 70 to about 80, about 75 to about 85, about 80 to about 90, about 85 to about 95 or about 90 to 100 nucleotides in length.

The disclosed hetero-bifunctional ligands may be synthesized by techniques known in the art. The hetero-bifunctional ligands are formed from target receptor and internalization receptor-binding agents, which both can be modified or activated, for example chemically activated, so that it can be covalently bound to a linker, such that the target receptor-binding agent and the internalizing receptor-binding agent are joined by the linker.

Molecules, such as ligands for different receptors (for example a ligand for a target receptor and an internalizing receptor) can be linked together using any number of means known to those of skill in the art. In one example, a ligand specific for a target receptor is covalently bound to a ligand specific for an internalizing receptor. The linker can be any molecule used to join a molecule to another molecule. Depending on such factors as the molecules to be linked and the conditions in which the method of detection is performed, the linker can vary in length and composition for optimizing such properties as flexibility, stability and resistance to certain chemical and/or temperature parameters. A linker that is part of a hetero-bifunctional ligand should be of sufficient length that the hetero-bifunctional ligand is capable of binding to both a target receptor and an internalizing receptor. In some embodiments, a linker is a heterologous linker, such that the linker heterologous to the target receptor binding and the internalizing receptor-binding agent.

Suitable linkers are well known to those of skill in the art and include, but are not limited to, straight or branched-chain carbon linkers, heterocyclic carbon linkers or peptide linkers. Peptide linkers are short sequences of amino acids, such as 1, 2, 3, 4, 5, 6, 7, 8, 9, 10, 11, 12, 13, 14, 15 or ever greater than 15 amino acids in length. In some examples, a linker is peptide such as poly-lysine, poly-glutamine or even combinations thereof. One skilled in the art will recognize, for a hetero-bifunctional ligand formed from two or more constituents, each of the constituents will contain the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. In some cases, the linking group can be designed to be either hydrophilic or hydrophobic in order to enhance the desired binding characteristics of the ligand and the receptor. The covalent linkages should be stable relative to the solution conditions under which the ligand and linking group are subjected.

Where the receptor-binding agents are polypeptides, the linkers may be joined to the constituent amino acids through their side groups (such as through a disulfide linkage to cysteine) or to the alpha carbon amino and carboxyl groups of the terminal amino acids. Alternatively, where the receptor-binding agents are polypeptides, the linker and both receptor-binding agents can be encoded as a single fusion polypeptide such that the target receptor-binding agent and the internalizing receptor-binding agent are joined by peptide bonds.

The procedure for attaching a molecule to a polypeptide varies according to the chemical structure of the molecule. Polypeptides typically contain a variety of functional groups; for example, carboxylic acid (COOH), free amine (—$NH_2$) or sulfhydryl (—SH) groups, which are available for reaction with a suitable functional group on a polypeptide. Alternatively, the polypeptide is derivatized to expose or attach additional reactive functional groups. The derivatization may involve attachment of any of a number of linker molecules such as those available from Pierce Chemical Company, Rockford, Ill. In particular examples, a linker is the combination of streptavidin or avidin and biotin.

Aspects of this disclosure relate to a method for inducing the internalization of a target receptor. Such methods include contacting a cell that expresses the target receptor on its surface with an effective amount of a hetero-bifunctional ligand that includes a specific binding agent capable of binding to the target receptor. By appropriate selection of a target receptor specific binding agent and internalizing receptor-binding agent for inclusion in a hetero-bifunctional ligand, it is possible to induce the internalization of any target receptor.

In some embodiments, a target receptor-binding agent is a ligand for a growth factor receptor, such as a neuropilin-1, neuropilin-2 or a vascular endothelial growth factor (VEGF) receptor, such as vascular endothelial growth factor receptor (VEGFR)-1, VEGFR-2, VEGFR-3. In specific embodiments, a hetero-bifunctional ligand is constructed to induce the internalization of VEGFR-2 and/or NPR-1. Such a hetero-bifunctional ligand includes a target receptor-binding agent that is VEGF-A (the ligand for the receptor VEGFR-2 and co-receptor Neuropilin-1) and Acetylated-LDL (a scavenger ligand that induces the internalization of scavenger receptors), which are chemically linked, for example with crosslinkers available commercially from Pierce (Bioconjugate Toolkit Reagents) to tag VEGF-A and Acetylated-LDL with two different hetero-bifunctional linkers (A and B). After derivation of VEGF-A-(linker A) and Acetylated-LDL-(linker B), these two linker molecules are linked together. As a result, the final product is a hetero-bifunctional ligand composed of (VEGF-A)-(linker A)-(linker B)-(Acetylated-LDL). Such a hetero-bifunctional ligand is of use in inhibiting angiogenesis and/or in the treatment of cancer. In some embodiments, a hetero-bifunctional ligand includes a linker heterologous to one or both of the internalizing receptor-binding agent and the target receptor-binding agent. In some examples, the internalizing receptor-binding agent is a polysaccharide, such as sulfated dextran or Fucoidan and the target receptor-binding agent is not a polysaccharide. In some examples, the target receptor-binding agent is a polysaccharide, such as sulfated dextran or Fucoidan and the target internalizing receptor binding agent is not a polysaccharide.

Receptor Antibodies

A receptor polypeptide (for example a target receptor or internalizing receptor polypeptide) or a fragment or conservative variant thereof can be used to produce antibodies which are immunoreactive or bind to an epitope of the receptor polypeptide. Polyclonal or monoclonal antibodies (including humanized monoclonal antibodies) and fragments of monoclonal antibodies such as Fab, F(ab')2 and Fv fragments, as well as any other agent capable of specifically binding to an peptide derived from a target or internalizing receptor may be produced. Optimally, antibodies raised against a target or internalizing receptor polypeptide would specifically bind the target or internalizing receptor polypeptide of interest (or a cell expressing such a peptide in its surface). That is, such antibodies would recognize and bind the protein and would not substantially recognize or bind to other proteins found in human or other cells. The determination that an antibody specifically binds the target or internalizing receptor polypeptide of interest is made by any one of a number of standard immunoassay methods; for instance, the Western blotting technique (Sambrook et al., 1989, Molecular Cloning: A Laboratory Manual, Cold Spring Harbor Laboratory, Cold Spring Harbor, N.Y.).

A substantially pure target or internalizing receptor polypeptide suitable for use as an immunogen is isolated by purification or recombinant expression. Concentration of protein in the final preparation is adjusted, for example, by concentration on an Amicon filter device, to the level of a few micrograms per milliliter. Monoclonal or polyclonal antibody to the protein can then be prepared as described by Harlow and Lane (Antibodies, A Laboratory Manual, Cold Spring Harbor Press. 1988).

Alternatively, antibodies may be raised against a synthetic target or internalizing receptor polypeptide synthesized on a commercially available peptide synthesizer based upon the predicted amino acid or known sequence of the target or internalizing receptor polypeptide (Harlow and Lane, Antibodies, A Laboratory Manual, Cold Spring Harbor Press. 1988).

The preparation of polyclonal antibodies is well-known to those skilled in the art. See, for example, Green et al., "Production of Polyclonal Antisera," in Immunochemical Protocols pages 1-5, Manson, ed., Humana Press 1992; Coligan et al., "Production of Polyclonal Antisera in Rabbits, Rats, Mice and Hamsters," in: Current Protocols in Immunology, section 2.4.1, 1992.

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than larger molecules and may require the use of carriers and adjuvants. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (*J. Clin. Endocrinol. Metab.* 33:988-91, 1971).

Booster injections can be given at regular intervals and antiserum harvested when antibody titer thereof, as determined semi-quantitatively, for example, by double immunodiffusion in agar against known concentrations of the antigen, begins to fall. See, for example, Ouchterlony et al. (In: Handbook of Experimental Immunology, Wier, D. (ed.). Chapter 19. Blackwell. 1973). Plateau concentration of antibody is usually in the range of 0.1 to 0.2 mg/ml of serum (about 12 µM). Affinity of the antisera for the antigen is measured by analysis of competitive binding curves, as described, for example, by Fisher (Manual of Clinical Immunology, Chapter 42. 1980).

The preparation of monoclonal antibodies likewise is conventional. See, for example, Kohler & Milstein, *Nature* 256: 495, 1975; Coligan et al., sections 2.5.1-2.6.7; and Harlow et al., in: *Antibodies: a Laboratory Manual*, page 726, Cold Spring Harbor Pub., 1988. Monoclonal antibody to epitopes of the target or internalizing receptor polypeptide identified and isolated as described can be prepared from murine hybridomas according to the classical method of Kohler and Milstein (*Nature* 256:495, 1975) or derivative methods thereof. Briefly, a mouse is repetitively inoculated with a few micrograms of the selected protein over a period of a few weeks. The mouse is then sacrificed and the antibody-producing cells of the spleen isolated. The spleen cells are fused by means of polyethylene glycol or other means with selected mouse myeloma cells and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980) and derivative methods thereof. Selected positive clones can be expanded and their monoclonal antibody product harvested for use.

Monoclonal antibodies can be isolated and purified from hybridoma cultures by a variety of well-established techniques. Such isolation techniques include affinity chromatography with Protein-A Sepharose, size-exclusion chromatography and ion-exchange chromatography. See, for example, Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor or in immobilized or entrapped cell culture. Multiplication in vivo may be carried out by injecting cell clones into mammals histocompatible with the parent cells, for example, syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Specific antibodies can also be derived from subhuman primate antibody. General techniques for raising therapeutically useful antibodies in baboons can be found, for example, in WO 91/11465, 1991 and Losman et al., *Int. J. Cancer* 46:310, 1990.

Alternatively, an antibody that specifically binds a target receptor or an internalizing receptor can be derived from a humanized monoclonal antibody. Humanized monoclonal antibodies are produced by transferring mouse complementarity determining regions from heavy and light variable chains of the mouse immunoglobulin into a human variable domain and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE® Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, $F(ab')_2$ and Fv which are capable of binding the epitopic determinant. Methods of making these fragments are known in the art. (See for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647 and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments or other enzymatic, chemical or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. U.S.A.* 69:2659, 1972). Alternatively, the variable chains can be linked by an intermolecular disulfide bond or cross-linked by chemicals such as glutaraldehyde. See, for example, Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA or chemical synthesis, which can be conjugated to a carrier protein, if desired. Such commonly used carriers which are chemically coupled to the peptide include keyhole limpet hemocyanin (KLH), thyroglobulin, bovine serum albumin (BSA) and tetanus toxoid. The coupled peptide is then used to immunize the animal (for example, a mouse, a rat or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies, which mimic an epitope. For example, an anti-idiotypic monoclonal antibody made to a first monoclonal antibody will have a binding domain in the hypervariable region that is the "image" of the epitope bound by the first monoclonal antibody.

To determine that a given antibody preparation (such as one produced in a mouse) specifically binds the target or internalizing receptor polypeptide of interest by Western blotting, total cellular protein containing the target or internalizing receptor polypeptide is extracted from murine myeloma cells and electrophoresed on a SDS-polyacrylamide gel. The proteins are then transferred to a membrane (for example, nitrocellulose) and the test antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically bind a target or internalizing receptor polypeptide of interest will, by this technique, be shown to bind to the target or internalizing receptor polypeptide band (which will be localized at a given position on the gel determined by its molecular weight). Non-specific binding of the antibody to other proteins (such as serum albumin) may occur and may be detectable as a weak signal on the Western blot. The non-specific nature of this binding will be recognized by one skilled in the art by the weak signal and/or unrelated portion obtained on the Western blot relative to the strong primary signal arising from the specific antibody-target or internalizing receptor polypeptide binding.

Methods for Recombinant Production of Hetero-Bifunctional Ligands

The hetero-bifunctional ligands disclosed herein, can be prepared by cloning techniques, for example when one or both of the target receptor-binding agent and the internalizing receptor-binding agent are peptides. In some examples, the target receptor-binding agent, the linker and the internalizing receptor-binding agent are produced as single fusion protein. Examples of appropriate cloning and sequencing techniques and instructions sufficient to direct persons of skill through many cloning exercises are found in Sambrook et al., *Molecular Cloning: A Laboratory Manual* (2nd Ed.), Vols. 1-3, Cold Spring Harbor Laboratory (1989), Berger and Kimmel (eds.), *Guide to Molecular Cloning Techniques*, Academic Press, Inc., San Diego Calif. (1987) or Ausubel et al. (eds.), *Current Protocols in Molecular Biology*, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.) and Applied Biosystems (Foster City, Calif.), as well as many other commercial sources known to one of skill.

In some embodiments, the disclosed hetero-bifunctional ligands are produced recombinantly, for example from cells transformed or transfected with polynucleotides encoding the hetero-bifunctional ligand or portion thereof. In some examples, the hetero-bifunctional ligand is produced as a single amino acid chain that includes the target receptor-binding agent, a polypeptide linker and the internalizing receptor-binding agent. In some examples the hetero-bifunctional ligand is produced from more than one polypeptide chain (for example a polypeptide that is a target receptor-binding agent and a different polypeptide that is the internalizing receptor-binding agent), which are linked together which a linker. In some examples, only one of the receptor-binding agents is a polypeptide. In some examples, the receptor-binding agent is a polypeptide, which includes a polypeptide linker, for example a polypeptide linker at the N or C terminus of the receptor-binding agent.

Methods for the manipulation and insertion of the nucleic acids encoding the disclosed hetero-bifunctional ligands or portions thereof into vectors for the expression of polypeptides are well known in the art (see for example, Sambrook et al., *Molecular Cloning, a Laboratory Manual,* 2d edition, Cold Spring Harbor Press, Cold Spring Harbor, N.Y., 1989 and Ausubel et al., *Current Protocols in Molecular Biology*, Greene Publishing Associates and John Wiley & Sons, New York, N.Y., 1994).

The nucleic acid constructs encoding the hetero-bifunctional ligands or portions thereof of this disclosure can be inserted into plasmids. However, other vectors (for example, viral vectors, phage, cosmids, etc.) can be utilized to replicate the nucleic acids. In the context of this disclosure, the nucleic acid constructs typically are expression vectors that contain a promoter sequence which facilitates the efficient transcription of the inserted genetic sequence of the host. The expression vector typically contains an origin of replication, a promoter, as well as specific nucleic acid sequences that allow phenotypic selection of the transformed cells.

More generally, polynucleotide sequences encoding hetero-bifunctional ligands or portions thereof of this disclosure can be operably linked to any promoter and/or enhancer that is capable of driving expression of the nucleic acid following introduction into a host cell. A promoter is an array of nucleic acid control sequences that directs transcription of a nucleic acid. Both constitutive and inducible promoters are included (see, for example, Bitter et al., *Methods in Enzymology* 153: 516-544, 1987).

DNA sequences encoding a hetero-bifunctional ligand or portion thereof can be expressed in vitro by DNA transfer into a suitable host cell. The cell may be prokaryotic or eukaryotic. Hosts can include microbial, yeast, insect and mammalian organisms. The term also includes any progeny of the subject host cell. Methods of stable transfer, meaning that the foreign DNA is continuously maintained in the host, are known in the art.

Transformation of a host cell with recombinant DNA can be carried out by conventional techniques that are well known to those of ordinary skill in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired or by electroporation.

When the host is a eukaryote, such methods of transfection of DNA as calcium phosphate coprecipitates, conventional mechanical procedures such as microinjection, electroporation, insertion of a plasmid encased in liposomes or virus vectors can be used. Eukaryotic cells can also be co-transformed with polynucleotide sequences encoding hetero-bifunctional ligand or portions thereof and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). Peptides can then be purified for host cells using methods known in the art.

Peptide Synthesis and Purification

Peptides derived from target or internalizing receptors may be produced, for example by chemically synthesis by any of a number of manual or automated methods of synthesis known in the art. In addition, peptides that form all or part of a hetero-bifunctional ligand can be produced synthetically. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT) and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. Solid Phase Peptide Synthesis, IRL Press: Oxford, 1989.

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole and ethanedithiol, in ratios of 100:5:5:2.5, for 0.5-3 hours at room temperature.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

Peptides produced by such methods also can be used to produce antibodies that bind the peptide and hence the protein from which the peptide was derived, for example a target or internalizing receptor.

Pharmaceutical Compositions

The hetero-bifunctional ligands disclosed herein may be included in pharmaceutical compositions (including therapeutic and prophylactic formulations), which are typically combined together with one or more pharmaceutically acceptable vehicles or carriers and, optionally, other therapeutic ingredients. The hetero-bifunctional ligands disclosed herein may be advantageously combined and/or used in combination with other therapeutic agents, different from the subject hetero-bifunctional ligands depending on the specific condition or disease associated with the target receptor-binding agent included as a component if the hetero-bifunctional ligand. For example, in situation where the target receptor-binding agent targets a receptor associated with cancer, it may be advantageous to use the hetero-bifunctional ligand with a chemotherapeutic agent. In many instances, co-administration of another agent in conjunction with the disclosed hetero-bifunctional ligands will enhance the efficacy of such agents.

Pharmaceutical compositions including a disclosed hetero-bifunctional ligand can be administered to subjects by a variety of routes, including by intramuscular, subcutaneous, intravenous, intra-arterial, intra-articular, intraperitoneal, intrathecal, intracerebroventricular, parenteral routes, mucosal administration modes, including by oral, rectal, intranasal, intrapulmonary or transdermal delivery or by topical delivery to other surfaces. In other alternative embodiments, the hetero-bifunctional ligand can be used ex vivo by direct exposure to cells, tissues or organs originating from a subject and which are then administered to a subject, which can be in conjunction with administration of a hetero-bifunctional ligand to the subject.

To formulate the pharmaceutical compositions, the hetero-bifunctional ligand can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin) and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0 or about 0.8 to about 1.7.

The hetero-bifunctional ligand can be dispersed in a base or vehicle, which can include a hydrophilic compound having a capacity to disperse the compound and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like and natural polymers, such as chitosan, collagen, sodium alginate, gelatin, hyaluronic acid and nontoxic metal salts thereof. Often, a biodegradable polymer is selected as a base or vehicle, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination and enhanced structural integrity can be imparted to the vehicle by partial crystallization, ionic bonding, crosslinking and the like. The vehicle can be provided in a variety of forms, including fluid or viscous solutions, gels, pastes, powders and microspheres.

The hetero-bifunctional ligand can be combined with the base or vehicle according to a variety of methods and release of the compound can be by diffusion, disintegration of the vehicle or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991) and dispersed in a biocompatible dispersing medium, which yields sustained delivery and biological activity over a protracted time.

The hetero-bifunctional ligands of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate and the like.

Pharmaceutical compositions for administering the hetero-bifunctional ligand can also be formulated as a solution, microemulsion or other ordered structure suitable for high concentration of active ingredients. The vehicle can be a solvent or dispersion medium containing, for example, water, ethanol, polyol (for example, glycerol, propylene glycol, liquid polyethylene glycol and the like) and suitable mixtures thereof. Proper fluidity for solutions can be maintained, for example, by the use of a coating such as lecithin, by the maintenance of a desired particle size in the case of dispersible formulations and by the use of surfactants. In many cases, it will be desirable to include isotonic agents, for example, sugars, polyalcohols, such as mannitol and sorbitol or sodium chloride in the composition. Prolonged absorption of the compound can be brought about by including in the composition an agent which delays absorption, for example, monostearate salts and gelatin.

In certain embodiments, the hetero-bifunctional ligand can be administered in a time-release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the hetero-bifunctional ligand and/or other biologically active agent. Numerous such materials are known in the art. Useful controlled-release binders are materials that are metabolized slowly under physiological conditions following their delivery (for example, at a mucosal surface or in the presence of bodily fluids). Appropriate binders include, but are not limited to, biocompatible polymers and copolymers well known in the art for use in sustained release formulations. Such biocompatible compounds are non-toxic and inert to surrounding tissues and do not trigger significant adverse side effects, such as nasal irritation, immune response, inflammation or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid) and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the hetero-bifunctional ligand and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, a disease associated with a particular target receptor, such that the induced internalization of the target receptor would provide a benefit to the subject) or to determine the status of an existing disease or condition in a subject. These screening methods include, for example, diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure.

The administration of the hetero-bifunctional ligand of the disclosure can be for either prophylactic or therapeutic purpose. When provided prophylactically, the hetero-bifunctional ligand is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the hetero-bifunctional ligand can be administered to the subject in a single bolus delivery, via continuous delivery (for example, continuous transdermal, mucosal or intravenous delivery) over an extended time period or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the hetero-bifunctional ligand (for example, amounts that are effective to alleviate one or more symptoms of a targeted disease or condition). In alternative embodiments, an effective amount or effective dose of the hetero-bifunctional ligand may simply inhibit or enhance one or more selected biological activities correlated with a disease or condition.

The actual dosage of a hetero-bifunctional ligand will vary according to factors such as the disease indication and particular status of the subject (for example, the subject's age, size, fitness, extent of symptoms, susceptibility factors and the like), time and route of administration, other drugs or treatments being administered concurrently, as well as the specific pharmacology of the hetero-bifunctional ligand for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a hetero-bifunctional ligand and/or other biologically active agent within the methods and formulations of the disclosure is about 0.01 mg/kg body weight to about 10 mg/kg body weight, such as about 0.05 mg/kg to about 5 mg/kg body weight or about 0.2 mg/kg to about 2 mg/kg body weight.

Dosage can be varied by the attending clinician to maintain a desired concentration at a target site. Higher or lower concentrations can be selected based on the mode of delivery, for example, trans-epidermal, rectal, oral, pulmonary, intranasal delivery, intravenous or subcutaneous delivery. To achieve the same serum concentration level, for example, slow-release particles with a release rate of 5 nanomolar (under standard conditions) would be administered at about twice the dosage of particles with a release rate of 10 nanomolar.

Also disclosed are kits, packages and multi-container units containing the herein described pharmaceutical compositions, such as pharmaceutical compositions containing one or more of the hetero-bifunctional ligands, active ingredients, and/or means for administering the same for use in the prevention and treatment of diseases and other conditions in subjects. In one embodiment, these kits include a container or formulation that contains one or more of the hetero-bifunctional ligands described herein. In one example, this component is formulated in a pharmaceutical preparation for delivery to a subject. The hetero-bifunctional ligand is optionally contained in a bulk dispensing container or unit or multi-unit dosage form. Packaging materials optionally include a label or instruction indicating for what treatment purposes and/or in what manner the pharmaceutical agent packaged therewith can be used.

Methods of Treatment

The disclosed hetero-bifunctional ligands can be used to internalize a receptor whose function contributes to a disease or condition. It can be determined if the internalization of a specific receptor (and subsequent loss of signaling capability) would be beneficial for a certain disease or condition. For example, cancer cells can express cell-surface receptors by which they receive proliferation signals, such as through autocrine or paracrine pathways. For cancer cells that express an internalization receptor, hetro-bifunctional ligands can be produced that target the internalizing receptor and a receptor that receives signals to induce proliferation of the cancer cell. Such a hetero-bifunctional ligand can be used to treat cancer by inhibiting the proliferation of the cancer cells. By inhibiting the proliferation of the cancer cells, hetero-bifunctional ligands can be used to treat or inhibit tumor growth and/or metastasis. In one example, VEGFRs are known to be involved in angiogenesis during tumor growth, thus a hetero-bifunctional ligand that is capable of inducing the internalization of VEGFR could be used to inhibit angiogenesis, for example to treat or inhibit tumor growth and/or metastasis. In another example, a target receptor that is a known site of viral binding and or entry can be internalized into the interior of the cell, so that the receptor is no longer available for the virus to use as either a viral binding site or entry site. In a specific example, a hetero-bifunctional ligand can be produced that includes a ligand for a cytokine receptor (such as CXCR4 and CCR5) used by HIV to assist in the entry of HIV into the cell, thus the disclosed hetero-bifunctional ligand can be used to internalize the cytokine receptor and inhibit the entry of HIV into the cell. In another example, a target receptor known to contribute to an autoimmune disorder can be internalized into the interior of the cell, so that the receptor is no longer available for ligand binding that contributes to the autoimmune disorder. Tissue Necrosis Factor (TNF) is known to be associated with autoimmune disorders, such as rheumatoid arthritis, juvenile rheumatoid arthritis, psoriatic arthritis, ankylosing spondylitis and plaque psoriasis. Thus, a hetero-bifunctional ligand that includes a ligand for a TNF receptor (such as TNF) can be used to internalize the TNF receptor and treat the autoimmune disorder. In another example, interleukin 6 (IL-6) is known to play a pathogenic role in rheumatoid arthritis, post transplant lymphoproliferative disease, Castleman's disease and atrial myxomas. Thus, a hetero-bifunctional ligand that includes a ligand for the IL-6 receptor (such as IL-6) can be used to internalize the IL-6 receptor and treat rheumatoid arthritis, post transplant lymphoproliferative disease, Castleman's disease or atrial myxoma. In another example, a hetero-bifunctional ligand can be produced that promotes angiogenesis when administered to a subject, for example by internalizing Notch 4, thereby rendering that receptor unavailable to bind Delta-like-4, a natural inhibitor of angiogenesis. Such a hetero-bifunctional ligand can be used for the promotion of angiogenesis for example for the treatment of angina, peripheral vascular insufficiency and coronary artery disease.

Aspects of this disclosure concern a method for treating a disease or condition associated with increased activation and/or functional abnormalities of a target receptor. Such methods include administering to a subject a therapeutic amount of a pharmaceutical composition that includes a hetero-bifunctional ligand, such as a hetero-bifunctional ligand disclosed herein. The hetero-bifunctional ligand present in the pharmaceutical composition binds to a target receptor whose function contributes to the disease or condition and induces the internalization of the target receptor, thereby treating the disease or condition.

In some embodiments, the disease or condition treatable with a disclosed hetero-bifunctional ligand is a viral infection in a subject. Examples of viruses that can be treated by selectively internalizing a receptor which the virus binds to gain entry into a cell include human adenovirus A, human adenovirus B, human adenovirus C, human adenovirus D, human adenovirus E, human adenovirus F, human astrovirus, human BK polyomavirus, human bocavirus, human coronavirus, human enterovirus, human foamy virus, human herpesvirus, Varicella zoster virus, Epstein-Barr virus, human herpesvirus, human immunodeficiency virus, human metapneumovirus, human papillomavirus, human parainfluenza virus, human parechovirus, human parvovirus, human respiratory syncytial virus, human rhinovirus, human spumaretrovirus, human T-lymphotropic virus, cytomegalovirus (CMV) and lentivirus, such as an HIV virus, such as HIV-1 or HIV-2. A method of inhibiting or treating a viral infection in a subject includes administering to the subject a pharmaceutical composition that includes a hetero-bifunctional ligand that has a target receptor-binding agent that specifically binds to a receptor used as a site of viral attachment and/or entry into the cell, in which the hetero-bifunctional ligand present in the pharmaceutical composition binds to the target receptor and induces the internalization of the receptor, thereby treating or inhibiting the viral infection.

Method for Inhibiting Angiogenesis

In some embodiments, the disease or condition treatable with a disclosed hetero-bifunctional ligand is dependant on the grown of new blood vessels, for example, macular degeneration, diabetic retinopathy and rheumatoid arthritis and cancer, such as a primary or metastatic cancer. Cancers rely on neovascularization to grow locally and produce metastasis. Thus a reduction in angiogenesis is beneficial to treat cancer. Examples of types of cancer that can be treated using the disclosed hetero-bifunctional ligands are leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia, solid tumors, such as sarcomas and carcinomas, include fibrosarcoma, myxosarcoma, liposarcoma, chondrosarcoma, osteogenic sarcoma and other sarcomas, synovioma, mesothelioma, Ewing's tumor, leiomyosarcoma, rhabdomyosarcoma, colon cancer (such as colon carcinoma), gastric cancer, (for example, gastric adenocarcinoma, such as intestinal type gastric adenocarcinoma and diffuse type gastric adenocarcinoma), lymphoid malignancy, pancreatic cancer, breast cancer (such as adenocarcinoma), lung cancers, gynecological cancers (such as cancers of the uterus (for example endometrial carcinoma), cervix (for example cervical carcinoma, pre-tumor cervical dysplasia), ovaries (for example, ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (for example squamous cell carcinoma, intraepithelial carcinoma, adenocarcinoma, fibrosarcoma, melanoma), vagina (for example clear cell carcinoma, squamous cell carcinoma, botryoid sarcoma), embryonal rhabdomyosarcoma and fallopian tubules (for example carcinoma), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma) and skin cancer (such as melanoma and non-melonoma).

In specific embodiments, the method is a method of inhibiting angiogenesis. Such a method includes administering to a subject a pharmaceutical composition that includes a disclosed hetero-bifunctional ligand, wherein the hetero-bifunctional ligand present in the pharmaceutical composition binds to the receptor for which VEGF-A is a ligand and induces the internalization of the receptor for which VEGF-A is a ligand, thereby inhibiting angiogenesis. In some embodiments, the method is a method of treating or inhibiting cancer. In specific embodiment VEGF-A (the ligand for the receptor VEGFR-2 and co-receptor Neuropilin-1) is linked to Acetylated-LDL (a scavenger ligand which induces the internalization of scavenger receptors). In another specific embodiment VEGF-A (the ligand for the receptor VEGFR-2 and co-receptor Neuropilin-1) is linked to an oligonucleotide (a scavenger ligand which induces the internalization of scavenger receptors), such as poly G or a derivative thereof.

Method of Inhibiting HIV Binding or Infection

Methods are provided herein for inhibiting HIV binding to a cell, HIV infection or a combination thereof via administering an agent including at least one hetero-bifunctional ligand that induces the internalization of a receptor used by HIV to bind a cell or gain entry into a cell, such as a hetero-bifunctional ligand that binds to and induces the internalization of CCR5 or CXCR4. In one example, HIV infection can be reduced or inhibited by contacting a cell with an effective amount of an agent including bifunctional ligands that induce the internalization of a receptor used by HIV to bind a cell or gain entry into a cell. The agent specifically induces the internalization of the receptor used by HIV to bind a cell or gain entry into a cell and thereby reduces or inhibits HIV infection. This inhibition translates to a reduction of HIV replication and spread in infected individuals. In specific embodiments, the method is a method of treating or inhibiting HIV infection in a subject. Such a method includes administering a pharmaceutical composition that includes a hetero-bifunctional ligand that has a target receptor-binding agent that specifically binds to a target receptor used as a site of HIV attachment and/or entry into the cell, for example a cytokine receptor, such as CCR5 or CXCR4, in which the hetero-bifunctional ligand present in the pharmaceutical composition binds to the target receptor used as a site of HIV attachment and/or entry into the cell and induces the internalization of the receptor, thereby treating or inhibiting the HIV infection.

HIV infection does not need to be completely eliminated for the composition to be effective. For example, a composition can decrease HIV infection by a desired amount, for example by at least 10%, at least 20%, at least 50%, at least 60%, at least 70%, at least 80%, at least 90%, at least 95%, at least 98% or even at least 100% (elimination of detectable HIV infected cells), as compared to HIV infection in the absence of the composition. In another example, the cell is also contacted with an effective amount of an additional agent, such as anti-viral agent. The cell can be in vivo or in vitro.

In additional examples, HIV replication can be reduced or inhibited by similar methods. For example, methods can include contacting a cell with an effective amount of an agent including receptor used by HIV to bind a cell or gain entry into a cell and thereby reduces or inhibits HIV replication.

The HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98% or even at least 100% (elimination of detectable HIV), as compared to HIV replication in the absence of the composition. In example, the cell is also contacted with an effective amount of an additional agent, such as anti-viral agent. The cell can be treated in vivo, in vitro or ex vivo.

EXAMPLES

Example 1

Materials and Methods

This example describes exemplary reagents and methods used in the examples that follow.

Reagents and Cytokines

Porcine heparin sodium salt, chondroitin sulfate A, B, shark cartilage chondroitin 6-sulfate (chondroitin sulfate C), dextran, dextran sulfate Mr 8,000, Mr 500,000, Fucoidan Mr 66,410 and bovine fibronectin were obtained from Sigma (St. Louis, Mo.). Bovine kidney heparin sulfate was obtained from CALBIOCHEM® (San Diego, Calif.). Recombinant human $VEGF_{165}$, chimeric rat NRP1/Fc, human Sema3A/Fc, SREC-I/Fc, gp130/Fc and B7-1/Fc were obtained from R&D SYSTEMS® (Minneapolis, Minn.). Ac-LDL and 1,1'-dioctadecyl-Ac-LDL (DiO-Ac-LDL) were obtained from Biomedical Technologies (Stoughton, Mass.). Alexa-fluor 488 Ac-LDL was obtained from INVITROGEN™ (Carlsbad, Calif.).

Cells and Culture Conditions

Primary human umbilical vein endothelial cells (HUVEC) were prepared and maintained as previously described (Salvucci et al., Blood 99:2703-2711, 2002). HUVEC were used between the second and the fifth passage. The cell line RS4;11 (RS4, ATCC, Manassas, Va.) was maintained in RPMI 1640 with 10% FBS; the cell line HS-5, COS7 and HEK-293 (ATCC) were maintained in Dulbecco's Modified Eagle's Medium (DMEM) with 10% FBS. The murine plasmacytoma MOPC-315 cell line was propagated in RPMI 1640 with 10% FBS and 55 µM 2-mercaptoethanol.

NRP1-Heparin Binding Assay

Heparin was biotinylated as described previously (De La Luz Siena et al. Blood 103:2452-2459, 2004). Biotinylated heparin (1.8 U/ml in PBS) was injected onto the flow cell of the Sensor Chip SA (Biacore, Piscataway, N.J.). 500 resonance units (RUs) of biotinylated heparin were immobilized. NRP1-heparin binding was analyzed by using the BIAcore 3000 system (Biacore). NRP1/Fc protein (20 nM) was diluted in HEPES (4-(2-hydroxyethyl)-1-piperazineethanesulfonic acid) buffer saline containing 0.005% Surfactant P20 (HBS-P, Biacore) injected over the heparin-coated or control flow cell surface at a flow rate 50 µl/min at 25° C. Association and dissociation phases were evaluated for 2 minutes. The sensor chip was regenerated with pulse of 2 M NaCl for 30 seconds. The data was analyzed using BIAevaluation software (Biacore) Immunocomplexes were visualized using a chemiluminescence detection system (GE Healthcare, Buckinghamshire, UK).

Affinity Purification with Immobilized Polysaccharide Gels

NRP1/Fc or gp130/Fc were incubated with heparin-gel, dextran sulfate-gel or maltose-gel (EY Laboratories, San Mateo, Calif.) at 25° C. for 1 hour. After washing with phosphate-buffered saline (PBS) (×3), gels were suspended in tricine SDS sample buffer (INVITROGEN™) and incubated at 100° C. for 5 minutes. Extracts were separated by sodium dodecyl sulfate polyacrylamide gel electrophoresis (SDS-PAGE), transferred onto nitrocellulose membrane (INVITROGEN™), blocked (5% skim milk in PBS 0.1% Tween20) and immunostained using biotin-conjugated anti-human IgG1 Ab (ZYMED®, South San Francisco, Calif.), followed by incubation with a horse radish peroxidase (HRP) conjugated streptavidin (ZYMED®).

Flow Cytometric Analysis

HUVEC were detached with 5 mM ethylene-diamine-tetra-acetic acid (EDTA) in PBS, washed with 1% fetal bovine serum (FBS) buffer (MEDIUM199, 1% FBS, 10 mM HEPES) and incubated with polysaccharides. After rinsing (×2) with 1M NaCl with 0.2% bovine serum albumin (BSA) followed by binding buffer (×2), cells were stained with PE-anti-BDCA-4 (NRP1) mAb (AD5-17F6; Miltenyi Biotec, Auburn, Calif.), PE-anti-VEGFR-1 mAb (49560; R&D Systems), PE-anti-VEGFR-2 mAb (89106; R&D SYSTEMS®), FITC-anti-CD31 mAb (WM59; BD Biosciences, San Jose, Calif.), PE-anti-VE-cadherin mAb (123413; R&D SYSTEMS®), PE-anti-CXCR4 mAb (2B11; BD Biosciences) or anti-NRP2 mAb (C-9; Santa Cruz Biotechnology, Santa Cruz, Calif.), anti-gp130 mAb (AM64; BD Biosciences) or anti-SREC-I Ab (AF2409; R&D Systems) followed by Alexa 488-conjugated anti-mouse Ab or Alexa 488-conjugated anti-goat Ab (INVITROGEN™). Data were collected using a FACScalibur® cytofluorometer (BD, Franklin Lakes, N.J.).

Laser Confocal Microscopy

Endothelial cells growing onto glass chamber slides (Nalge Nunc International, Rochester, N.Y.) coated with 5 µg/ml fibronectin were incubated in 1% FBS buffer with DS500 (8 µg/ml) and protease inhibitor cocktail III (CALBIOCHEM®) at 37° C. for the indicated times. The medium was replaced with 4% wt/vol paraformaldehyde for fixation, cells were washed with PBS and permeabilized with 0.1% Triton X100 in PBS. Cells were stained with mouse anti-human NRP1 mAb, rabbit anti-human Lamp1 Ab (PA1-654A; AFFINITY BIOREAGENTS™, Golden, Colo.) or goat anti-human SREC-I Ab in PBS with 3% BSA and 3% FBS at 4° C. for 16 hours. After washing, slides were incubated with Alexa 488-conjugated anti-mouse IgG Ab, Alexa 594-conjugated anti-rabbit IgG Ab or Alexa 488 or 594-conjugated anti-goat IgG Ab (INVITROGEN™), washed and mounted with VECTASHIELD® with DAPI (Vector Laboratories, Burlingame, Calif.). Images were obtained using the LSM 510 Zeiss confocal microscope (Carl Zeiss MicroImaging, Thornwood, N.Y.).

Western Blot Analysis

After incubation of endothelial cells in 1% FBS buffer with 2 µg/ml of DS500, cell pellets were suspended in lysis buffer (0.5% NP40, 150 mM NaCl, 10 mM TrisHCl pH 7.4) with protease inhibitor cocktail III. Cell lysates were separated by SDS-PAGE, transferred onto nitrocellulose membranes and immunostained using rabbit anti-NRP1 Ab (SANTA CRUZ BIOTECHNOLOGY®), followed by incubation with an HRP-conjugated anti-rabbit IgG Ab (GE Healthcare). Immunocomplexes were visualized using a chemiluminescence detection system (GE Healthcare, Buckinghamshire, UK). The membrane was re-blotted with goat anti-actin Ab (SANTA CRUZ BIOTECHNOLOGY®). Band intensities were measured.

Forced Expression of SREC-I and NRP1

Human NRP1 in pCMV6-XL4 was from OriGene Technologies (Rockville, Md.). Human SREC-I in pCMV-SPORT6 was from Open Biosystems (Hunstsville, Ala.). Plasmid vectors were transfected into HEK-293 or CHO-K1 cells with the use of LIPOFECTAMINE™ 2000 (INVITROGEN™). Cells were harvested 2 days after transfection for analysis.

ELISA-Based Binding Assays

Flat-bottom microtiter plates (96 well; IMMULON™ 4HBX, Thermo Labsystems, Franklin, Mass.) were coated with control human IgG1 (CALBIOCHEM®) or SREC-I/Fc chimeric protein (2 µg/ml). After blocking with PBS 0.1% Tween20 5% BSA, NRP1/Fc or control B7-1/Fc in PBS 0.1% Tween20 1% BSA were added with or without polysaccharide. Bound NRP1/Fc or B7-1/Fc was detected by anti-His mAb (INVITROGEN™), followed by HRP-conjugated anti-mouse IgG Ab (GE Healthcare). Reactions were visualized with tetramethoxybenzene peroxidase substrate (KPL, Gaithersburg, Md.) followed by addition of 1 M $H_2SO_4$ and read at 450 nm.

Cell Binding Assays

HUVEC were incubated in 1% FBS buffer with or without polysaccharides. Cells were washed with 1M NaCl twice, with 1% FBS buffer once, then incubated with Sema3A/Fc (2 µg/ml) or biotinylated $VEGF_{165}$ (100 ng/ml) (R&D SYSTEMS®) in 1% FBS buffer with 2 µg/ml heparin at 0° C. for 1 hour. Sema3A/Fc or biotinylated $VEGF_{165}$ bound to cells was detected with FITC-conjugated F(ab')$_2$ goat anti-human IgG Fc (Jackson ImmunoResearch Laboratories, West Grove, Pa.) or Avidin-FITC (R&D SYSTEMS®). Data were collected using a FACSCALIBUR® cytofluorometer.

Endothelial Cell Retraction Assay

HUVEC were incubated in 1% FBS buffer with or without DS500 (2 µg/ml) or Fucoidan (8 µg/ml) at 37° C. for 1 hour. After washing (×3) with assay medium (1% FBS buffer with 2 µg/ml heparin), HUVEC (16,000 cells/chamber) were added to the four-chamber glass slides pre-coated with 5 µg/ml fibronectin. After 1 hour stimulation with Sema3A (2 µg/ml, 1 hour), cell were fixed with 4% wt/vol paraformaldehyde; an average retraction score was obtained, as described (Narazaki and Tosato, *Blood* 107:3892-3901, 2006).

Endothelial Cell Proliferation Assay

HUVEC (2,000 cells/well) were cultured 3 days in 96-well tissue culture plates (Corning) in MEDIUM199 with 10% FBS and 25 µg/ml heparin, with or without 25 ng/ml of $VEGF_{165}$. Proliferation was measured by $^3H$ thymidine uptake (0.6 µCi/well, New England Nuclear) during the last 16 hours of culture.

In Vivo Matrigel™ and Tumor Angiogenesis Assays

All animal experiments were approved by the NCI-Bethesda Animal Care and Use Committee. The MATRIGEL™ assay was performed essentially as described. Mice (female C57BL/6J and BALB/cAnNCr 6-7 weeks old; The Jackson Laboratory, Bar Harbor, Me.) were injected subcutaneously (s.c.) with 0.5 ml MATRIGEL™ (BD Biosciences, Bedford, Mass.) containing $VEGF_{165}$ (0 or 150 ng/ml) plus heparin (0 or 500 ng/ml). The tumor angiogenesis assay was carried out in female BALB/cAnNCr mice (6-weeks old). Mice were injected s.c. with $10^7$ MOPC 315 mouse (BALB/c) plasma-cell tumor line (Eisen et al., *Biochemistry* 7:4126-4134, 1968). After injection of MATRIGEL™ or MOPC315 tumor cells, mice were injected intraperitoneally (i.p.) with polysaccharides (dextran, DS500 or Fucoidan 1 mg in 0.2 ml saline). Treatment was repeated daily for 6 (MATRIGEL™ assay) or 7 (tumor assay) days; plugs and tumors were removed 24 hours later. Tumor size (product of maximum perpendicular caliper measurements) and weight were measured. Tissues were fixed (cold 4% paraformaldehyde in PBS), soaked in 15 and 30% sucrose, embedded in OCT and processed for histology. Sections were stained with H&E and immunostained for CD31 with purified rat anti-mouse CD31/PECAM monoclonal antibody (BD Pharmingen) followed by Alexa-fluor 488-conjugated goat anti-rat IgG (MOLECULAR PROBES®) with DAPI. Angiogenesis was evaluated by digital measurement (IPLab software, BioVision Technologies, Inc. Exton, Pa.) of CD31-positive cells within MATRIGEL™ plugs and tumor tissues. The results are expressed as the mean surface area occupied by CD31-positive cells/unit area ($\mu m^2/10^6 \mu m^2$).

Statistical Analysis

Results are expressed as means±SD or SEM. Student's t-test was applied to evaluate group differences; a p-value of <0.05 was considered significant.

Example 2

Analysis of NRP1 Binding to Polysaccharides

Trials were carried out to determine whether other polysaccharides besides heparin can bind to NRP1. Using surface plasmon resonance (Biacore system), it was confirmed that recombinant NRP1 extracellular domain dose-dependently binds to a heparin-coated sensor chip. Based on the results of 3 trials, the Kd for the NRP1-heparin interaction was calculated at 0.69±0.13 nM (association rate constant (ka) 5.7±1.1×$10^6$ l/Ms and dissociation rate constant (kd) 3.9±0.19×$10^{-3}$ l/s). Using this system, the effects of various polysaccharides on the binding of NRP1 to immobilized heparin were examined (see FIG. 1A). Heparin itself at 1 μg/ml and to a lower extent at 0.1 μg/ml reduced the binding of NRP1 to heparin. Within a panel of 8 polysaccharides, dextran sulfate (DS) with Mr. 500 k Da (DS500), Fucoidan (1 and 0.1 μg/ml) and DS with Mr. 8 k Da (DS8) (1 μg/ml) prevented the binding of NRP1 to heparin. Heparan sulfate (HS), chondroitin sulfate A (ChoSul A), ChoSul B, ChoSul C and non-sulfated dextran (all at 1 μg/ml) minimally affected the binding of NRP1 to heparin. These results demonstrate that DS500 and Fucoidan inhibit NRP1 binding to heparin, suggesting that these polysaccharides can bind to NRP1. Binding of recombinant NRP1/Fc to immobilized DS (average Mr. 5 k Da) was also assessed. Heparin- and maltose-gel were used as controls for DS-gel and gp130/Fc was used as a control for NRP1/Fc. NRP1/Fc could be affinity purified abundantly from heparin-gel and DS-gel, but only a little from control maltose-gel. gp130/Fc was not able to be eluted from these gels (see FIG. 1B). These results demonstrate that DS directly binds to NRP1.

Example 3

Effects of DS500 and Fucoidan on Cell-Surface NRP1

This example describes exemplary methods for determining that DS500 and Fucoidan bind NRP1 on a cell surface.

DS500 and Fucoidan were tested for their ability to bind to cell-surface NRP1 and modulate its function. Primary human umbilical vein endothelial cells (HUVEC) were incubated with each of the polysaccharides tested in FIG. 1A at 37° C. for 1 hour and after washing with 1M NaCl (which effectively removes NRP1 from heparin as assessed by Biacore), levels of cell-surface NRP1 were measured by flow cytometry. As shown in FIG. 1C, DS500 and to a lower degree Fucoidan reduced NRP1 levels on HUVEC, but all other polysaccharides, including heparin, did not. By the same method, DS500 reduced cell-surface NRP2 and to a lower extent VEGFR-1 and VEGFR-2, but minimally reduced cell-surface CD31, VE-cadherin, gp130 or CXCR4 (FIG. 1D), indicating that DS500 does not indiscriminately alter detection of cell-surface molecules. Similar results were derived with Fucoidan. As shown in FIG. 1E, the conditions for reduction of cell-surface NRP1 and NRP2 by DS500 were examined. At 37° C., but not at 0° C., DS500 dose-dependently reduced cell-surface NRP1 and NRP2, with maximal inhibition at 2 μg/ml and $ED_{50}$ of 1.0±0.13 μg/ml (2.0±0.26 nM) (average of three trials). This reduction occurred progressively over 90 minutes. Thus, DS500 reduced cell-surface NRP1 on endothelial cells in a temperature, concentration and time-dependent manner. By using fluorescence microscopy, it was confirmed visually that cell-surface NRP1 and NRP2 is reduced on HUVEC after 1 hour incubation with DS500 (8 μg/ml) at 37° C. compared to control cells incubated in medium only (see, for example, FIG. 1F). The effect of human serum on the reduction of cell-surface NRP1 by DS500 was also examined. As shown in FIG. 1G, DS500 dose-dependently reduced cell-surface NRP1 on HUVEC in the presence of 95% human serum and the reduction was similar to that achieved in the presence of 1% human serum. Thus, DS500 reduces cell-surface NRP1 on endothelial cells in the presence of high serum concentrations.

Example 4

DS500 and Fucoidan Promote the Internalization of Cell-Surface NRP1

This example describes exemplary procedures for determining that DS500 and Fucoidan promote the internalization of cell-surface NRP1.

Figure 2A:
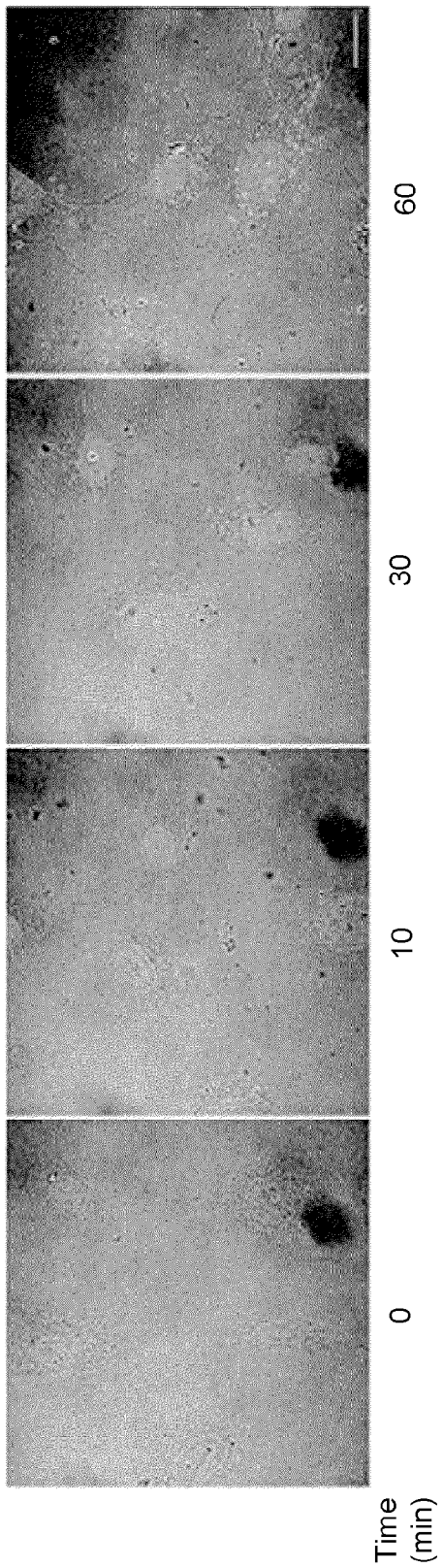
FIGS. 2A-2C are a set of digital images of immunostaining and immunoblots and a bar graph demonstrating that DS500 induces NRP1 internalization and that NRP1 co-localizes with Lamp1.
Figure 2B:
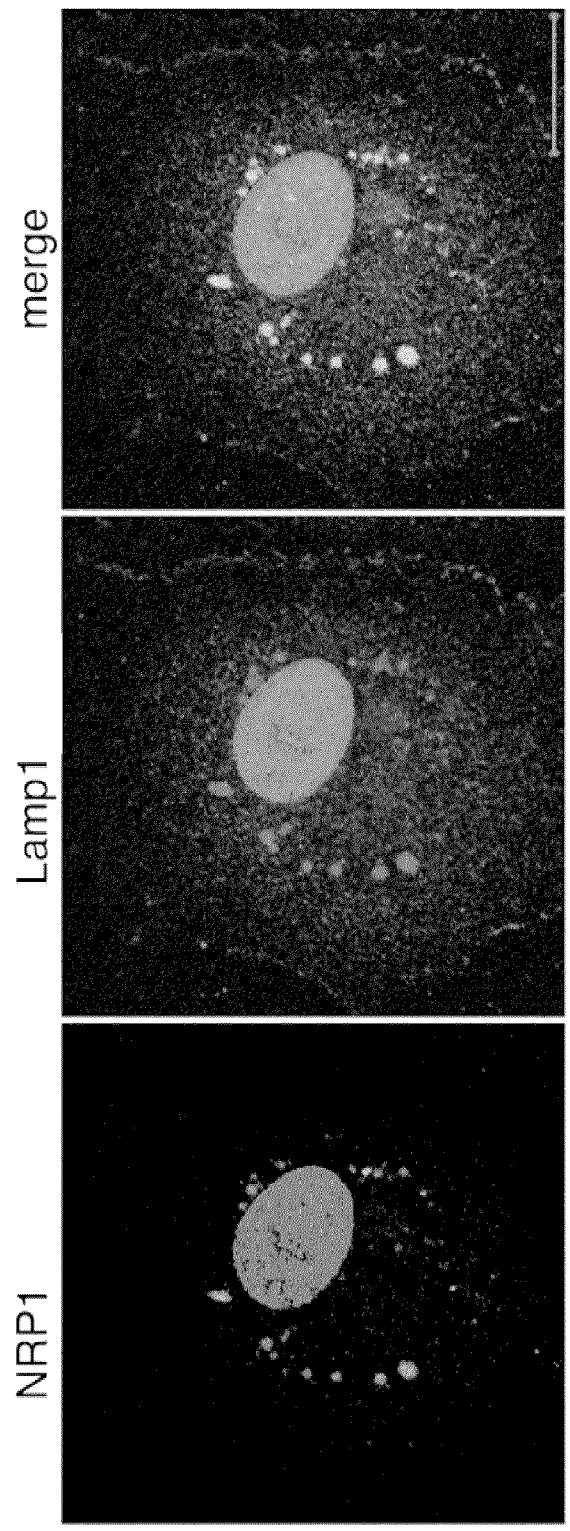
Figure 2C:
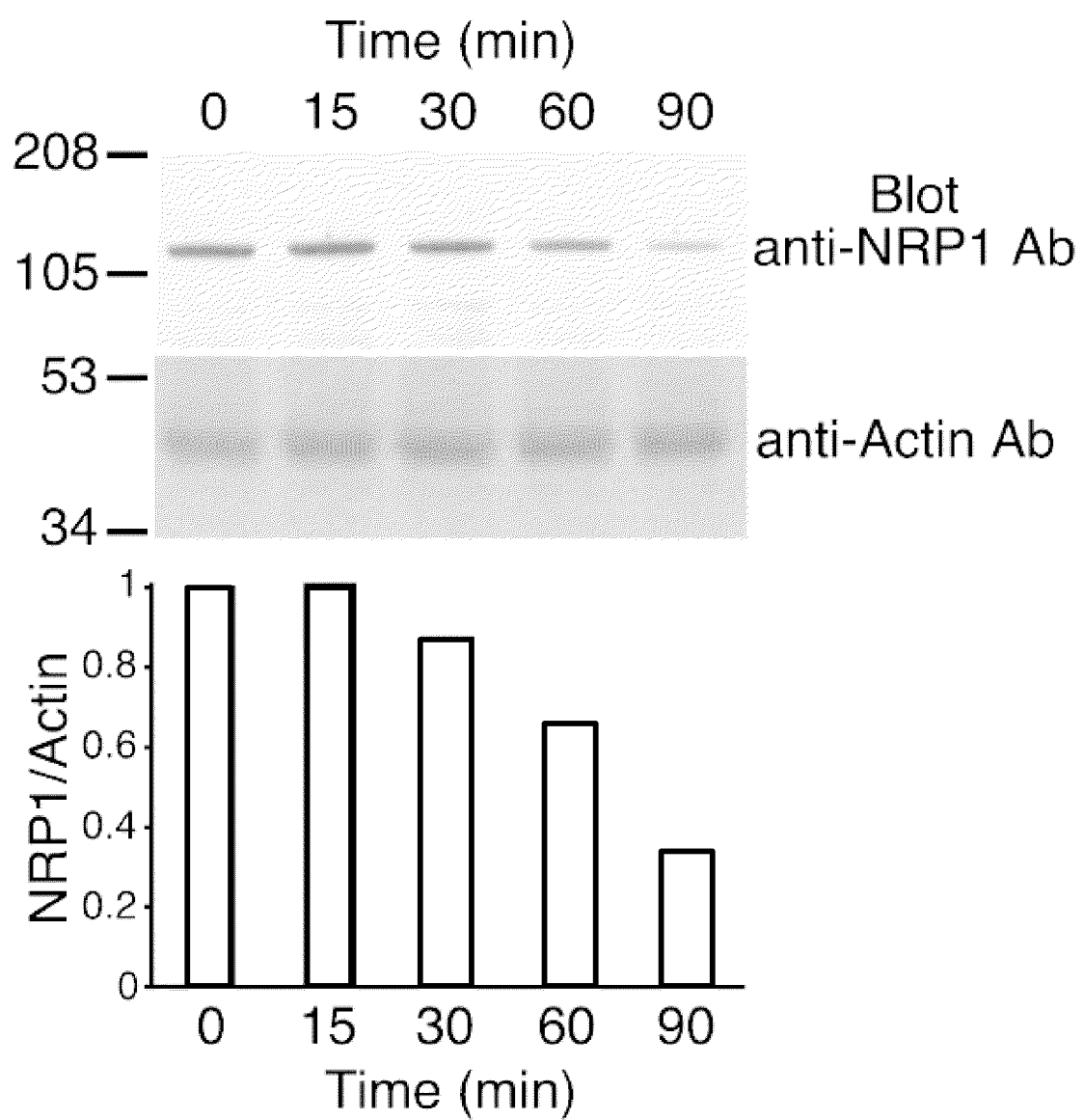

To determine whether DS500 and Fucoidan promote the internalization of NRP1, using confocal microscopy, NRP1 was traced in endothelial cells after 10-60 minutes incubation with DS500 (8 μg/ml) at 37° C. At time O, NRP1 is minimally detectable in HUVEC that have been fixed and permeabilized. After 10 minutes, NRP1 staining is visible at low levels and becomes progressively more intense. After 60 minutes, NRP1 is clearly identified by a vesicular-like staining (FIG. 2A) and co-localizes with Lamp1 (lysosome associated membrane protein-1) (FIG. 2B). Similar results were obtained with Fucoidan. These observations demonstrated that DS500 promotes NRP1 internalization and trafficking to the lysosomal compartment. Western-blot analysis of endothelial cell lysates showed that the intensity of the NRP1-related band decreases after incubation with DS500 longer than 30 minutes (FIG. 2C), indicating that NRP1 is degraded in the lysosomes. Together, these results demonstrate that DS500 promotes NRP1 internalization from the cell-surface to the cytoplasm where it reaches the lysosome and is degraded.

Example 5

DS500 and Fucoidan Promote the Internalization of Cell-Surface SREC-I

This example describes exemplary methods used to determine that DS500 and Fucoidan promote the internalization of cell-surface SREC-I.

Figure 3A:
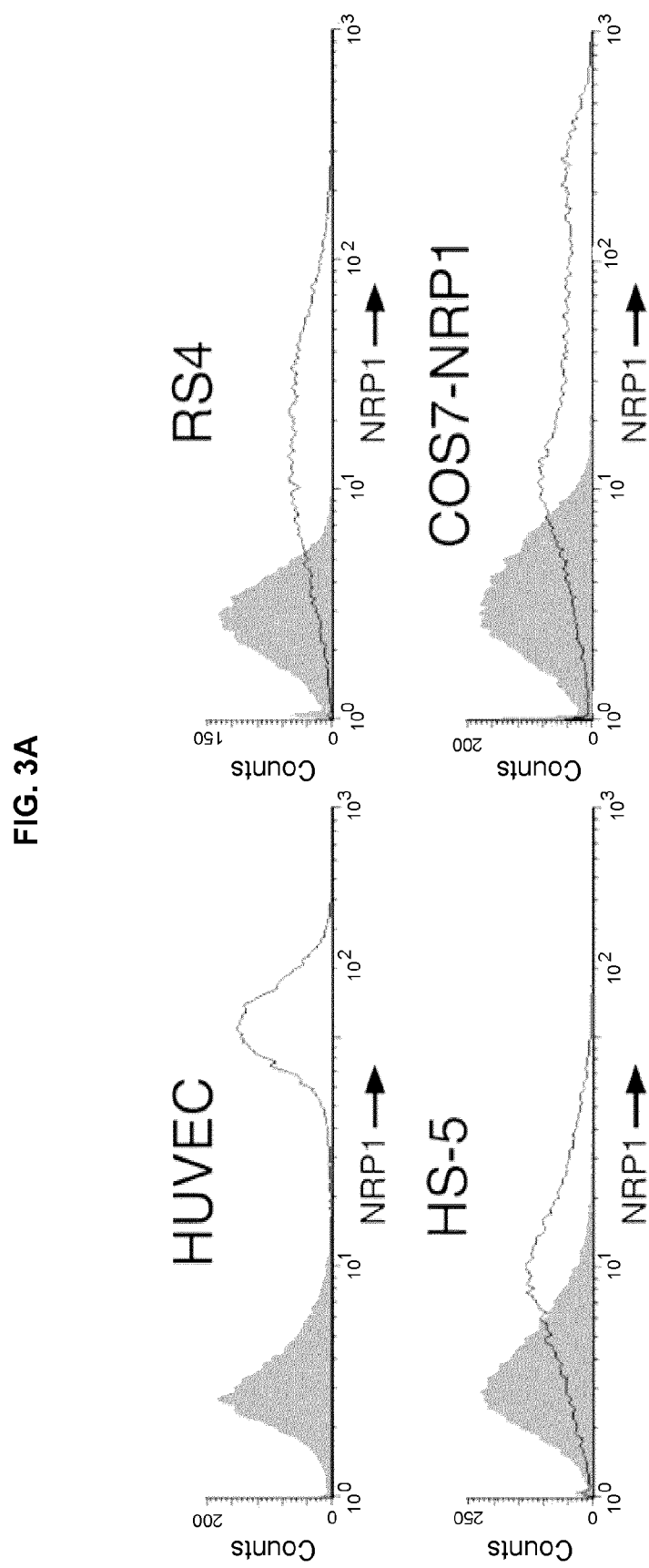
FIGS. 3A-3C is a set of histograms and graphs demonstrating that stimulation of cells co-expressing scavenger receptors and NRP1 with DS500 reduces the surface levels of NRP1.
Figure 3B:
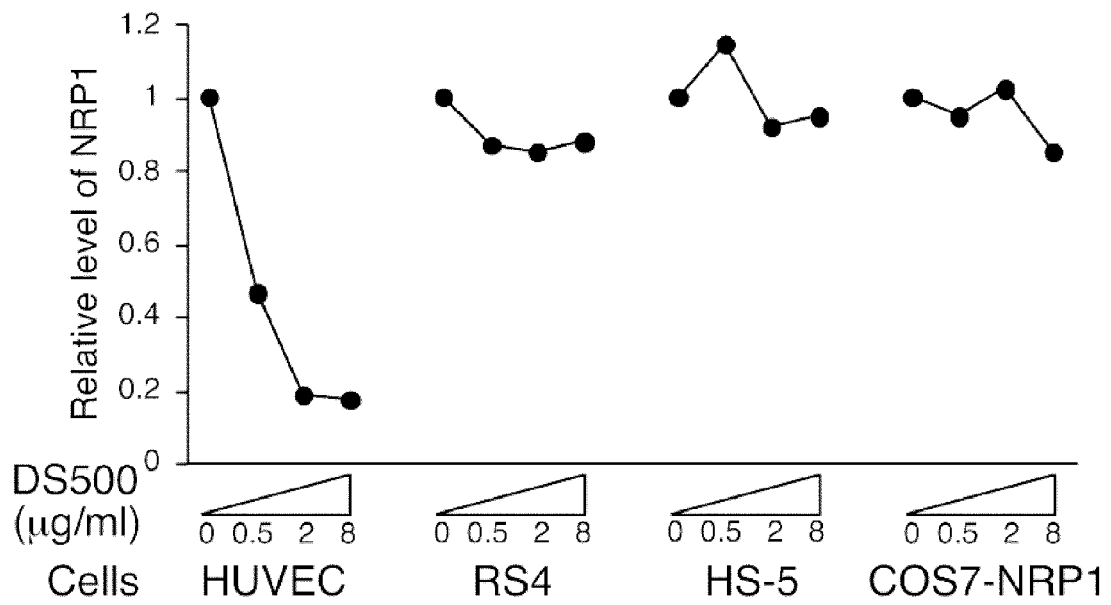
Figure 3C:
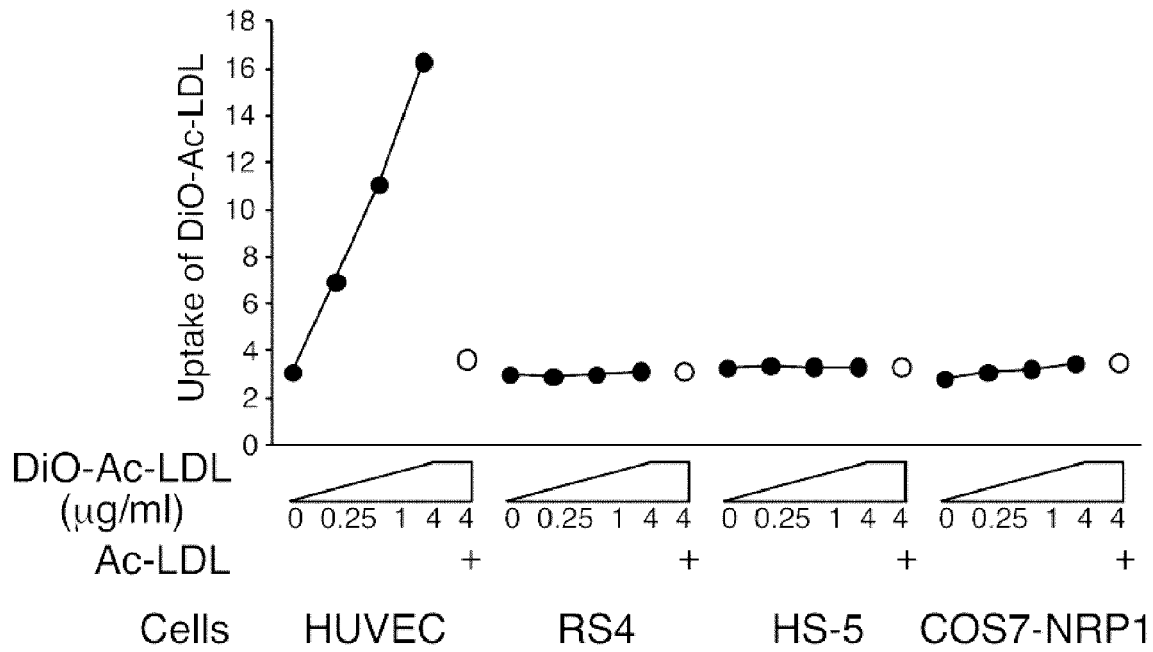

To determine the mechanisms underlying NRP1 internalization induced by DS500 it was tested whether binding of DS500 to cell-surface NRP1 is sufficient for internalization. Besides HUVEC, NRP1 is detected on the human leukemia RS4 and the human stromal HS-5 cell lines and on COS7 cells transduced with human NRP1 (COS7-NRP1) (FIG. 3A). DS500 dose-dependently reduced cell-surface NRP1 on HUVEC, but failed to do so on RS4, HS-5 or COS7-NRP1 cells (FIG. 3B), indicating that NRP1 internalization by DS500 requires additional components, which are present in HUVEC but not in the other cell types tested. One of the parameters found that distinguishes HUVEC from RS4, HS-5 and COS7-NRP1 is expression of scavenger receptors, which mediate the uptake of LDL modified by acetylation or oxidation. Some of the scavenger receptors are known to interact with sulfated polysaccharides. As shown in FIG. 3C, HUVEC displayed a dose-dependent uptake of DiO-Ac-LDL, whereas RS4, HS-5 and COS7-NRP1 displayed only minimal uptake. Unlabeled Ac-LDL blocked uptake of DiO-Ac-LDL in HUVEC, indicating the Ac-LDL specificity of DiO-Ac-LDL uptake in these cells.

Figure 4A:
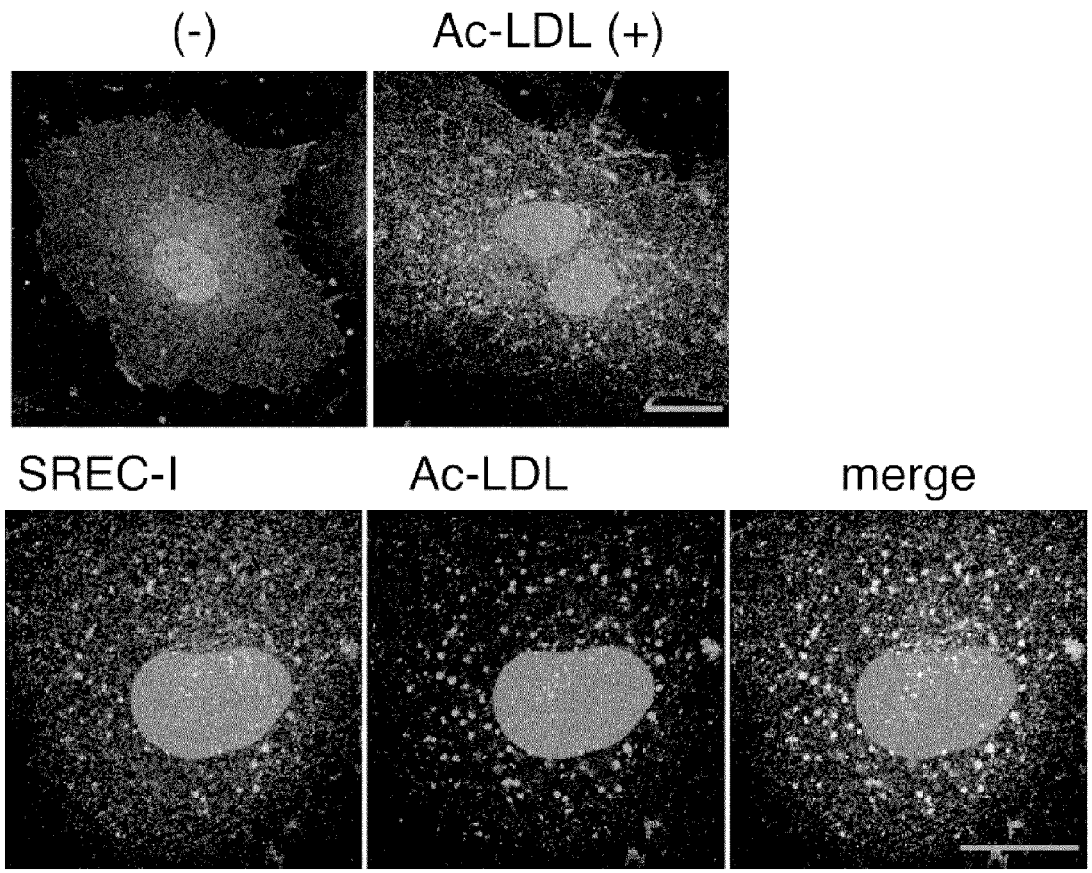
FIGS. 4A-4E is a set of digital images and graphs.

Several scavenger receptors have been identified in endothelial cells. Focusing on SREC-I (scavenger receptor expressed by endothelial cells-I), as it is highly expressed on HUVEC, it was determined that SREC-I can mediate the uptake of Ac-LDL in HUVEC. By confocal microscopy, it was found that Ac-LDL promotes the intracellular accumulation of SREC-I (FIG. 4A, upper panels) and that internalized SREC-I and Ac-LDL co-localize at least in part within HUVEC (FIG. 4A, lower panels). This result demonstrate that SREC-I can mediate the uptake of Ac-LDL in HUVEC and that SREC-I itself is internalized after binding to its ligand.

Figure 4B:
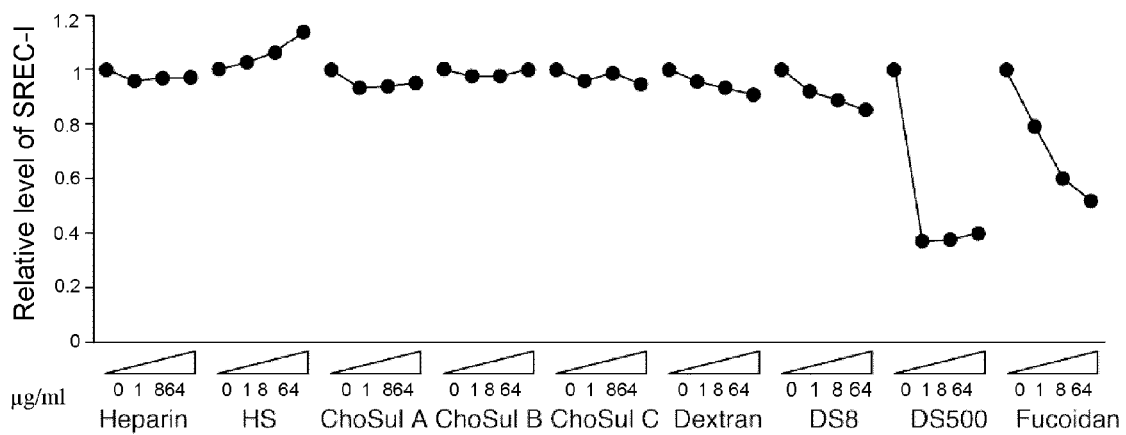
Figure 4C:
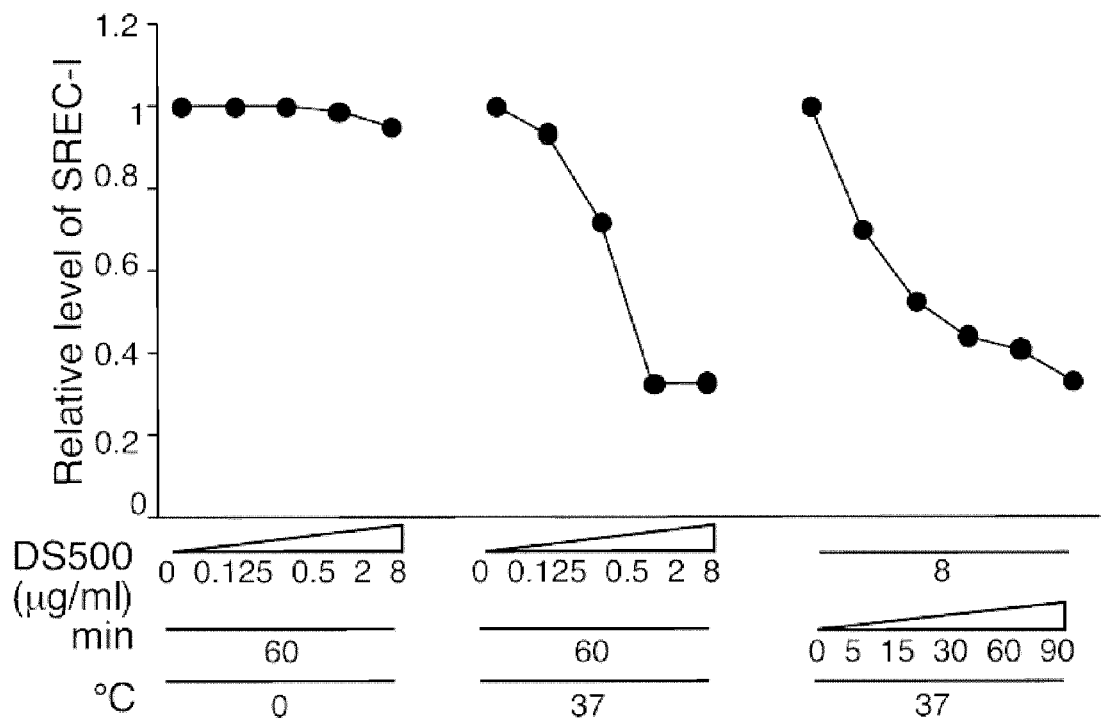
Figure 4D:
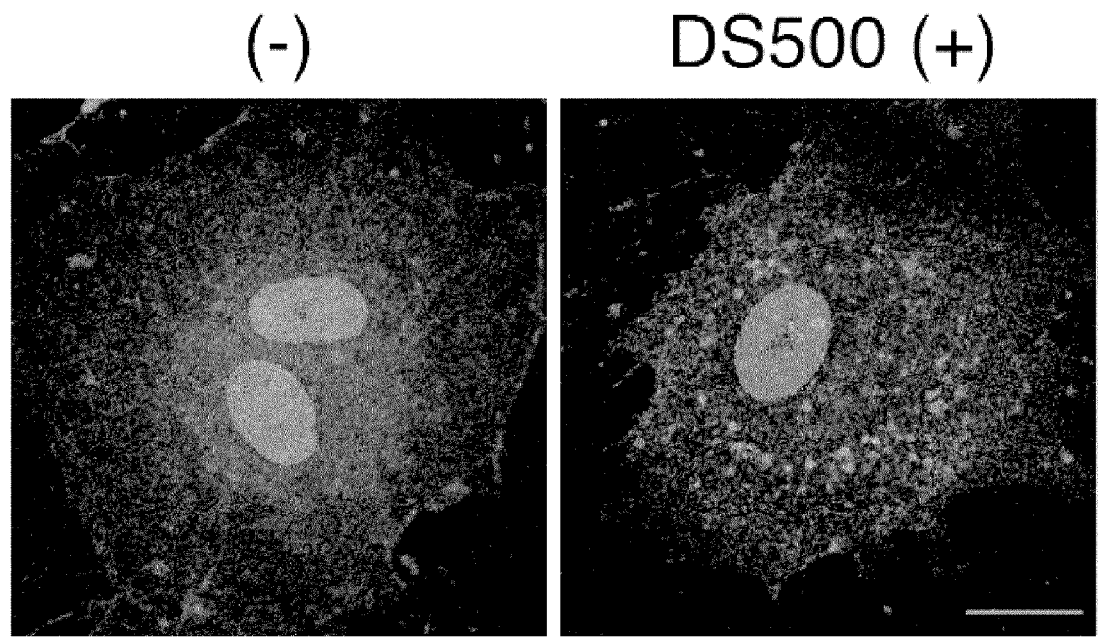
Figure 4E:
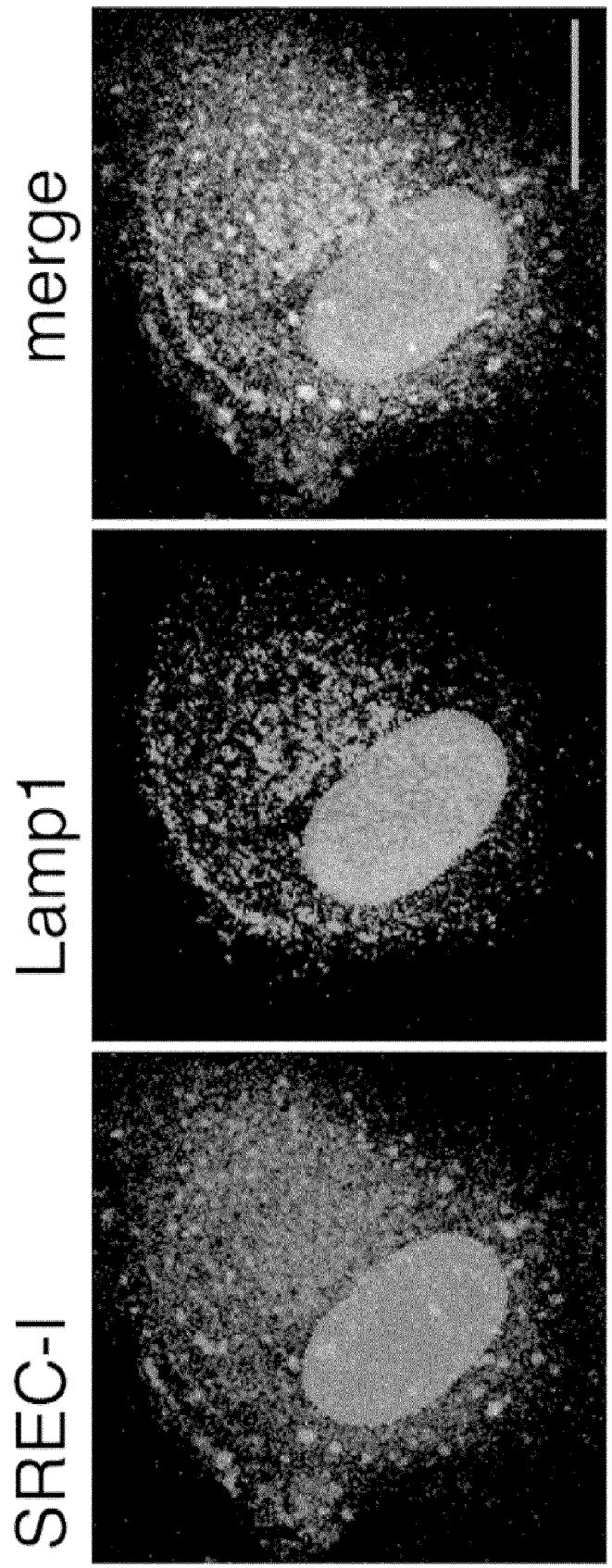

Certain sulfated polysaccharides can bind to selected scavenger receptors and block Ac-LDL uptake. Thus, it was determined whether DS500, Fucoidan and other sulfated polysaccharides could serve as ligands for SREC-I. Using FACS analysis for detection of cell surface SREC-I, it was determined that DS500 and to a lower degree Fucoidan reduced cell-surface SREC-I in HUVEC when incubated for 1 hour at 37° C., whereas heparin, HS, ChoSul A, ChoSul B, ChoSul C and non-sulfated dextran did not (FIG. 4B). VEGF165 reduced cell surface NRP1 but not SREC-I in HUVEC. This reduction of cell-surface SREC-I induced by DS500 in HUVEC was temperature, dose and time dependent (FIG. 4C). It was then determined that, like Ac-LDL, DS500 can promote the internalization of SREC-I in endothelial cells. After HUVEC were incubated with DS500 for 1 hour at 37° C., SREC-I displayed a vesicular-like cytoplasmic staining pattern, indicative of SREC-I internalization (FIG. 4D). Similar results were derived by incubation with Fucoidan. The internalized SREC-I co-localized in part with Lamp1, indicative of lysosomal localization (FIG. 4E).

Example 6

Sulfated Polysaccharides Bridge the Extracellular Domains of NRP1 and SREC-I and Induce the Coordinate Internalization of NRP1 and SREC-I This example describes exemplary procedures for determining that sulfated polysaccharides induce the internalization of NRP1 through concomitant interaction with NRP1 and SREC-I.

Figure 5C:
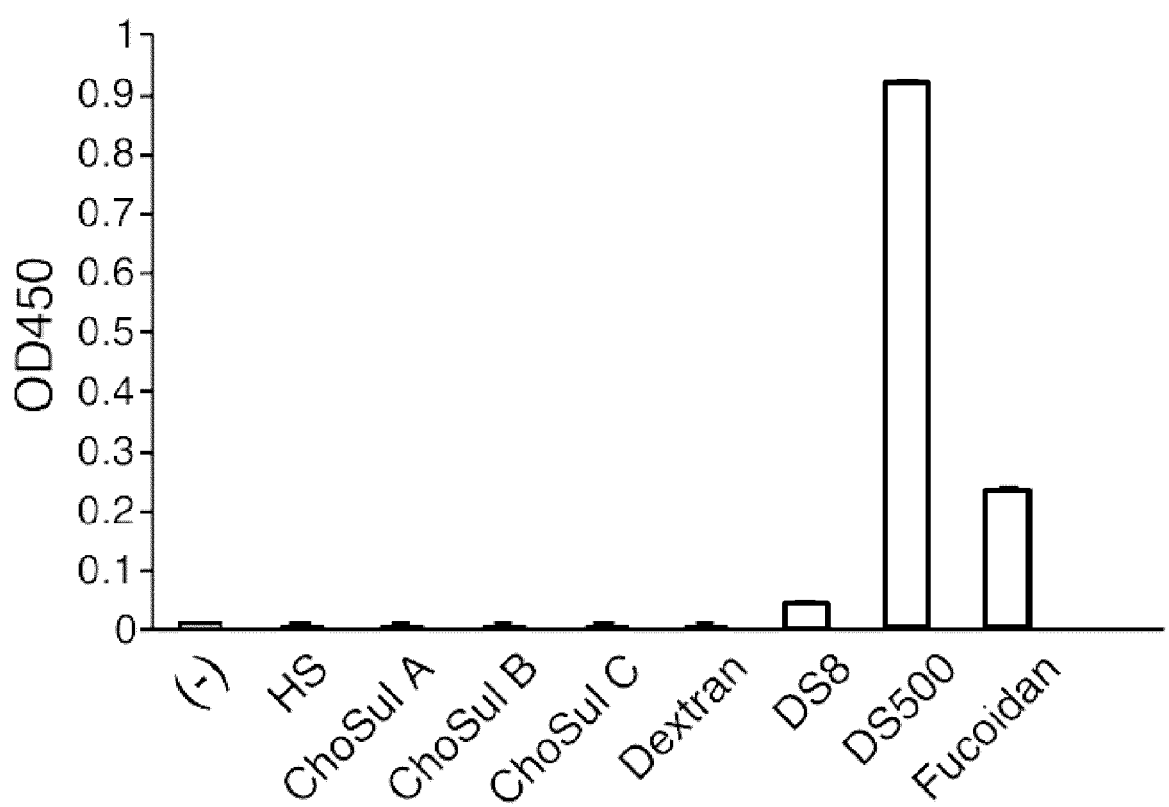
Figure 6A:
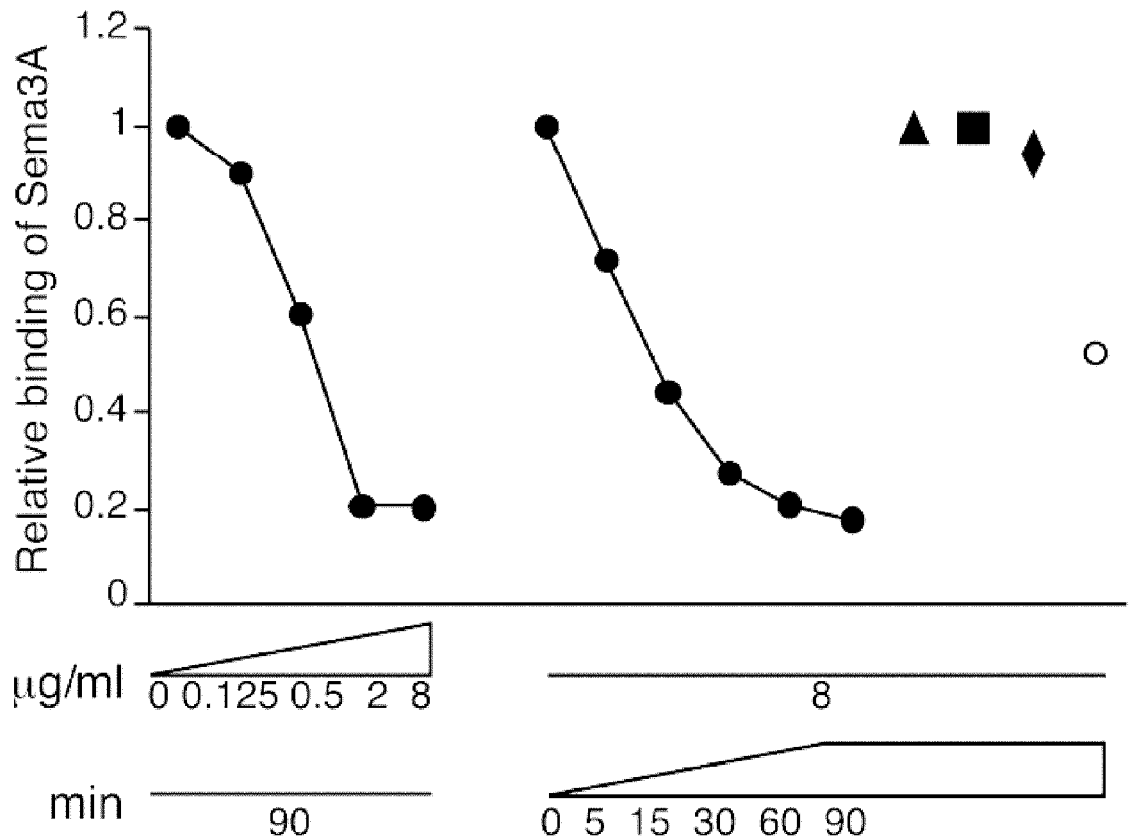
FIGS. 6A-6E is a set of digital images and graphs.
Figure 6B:
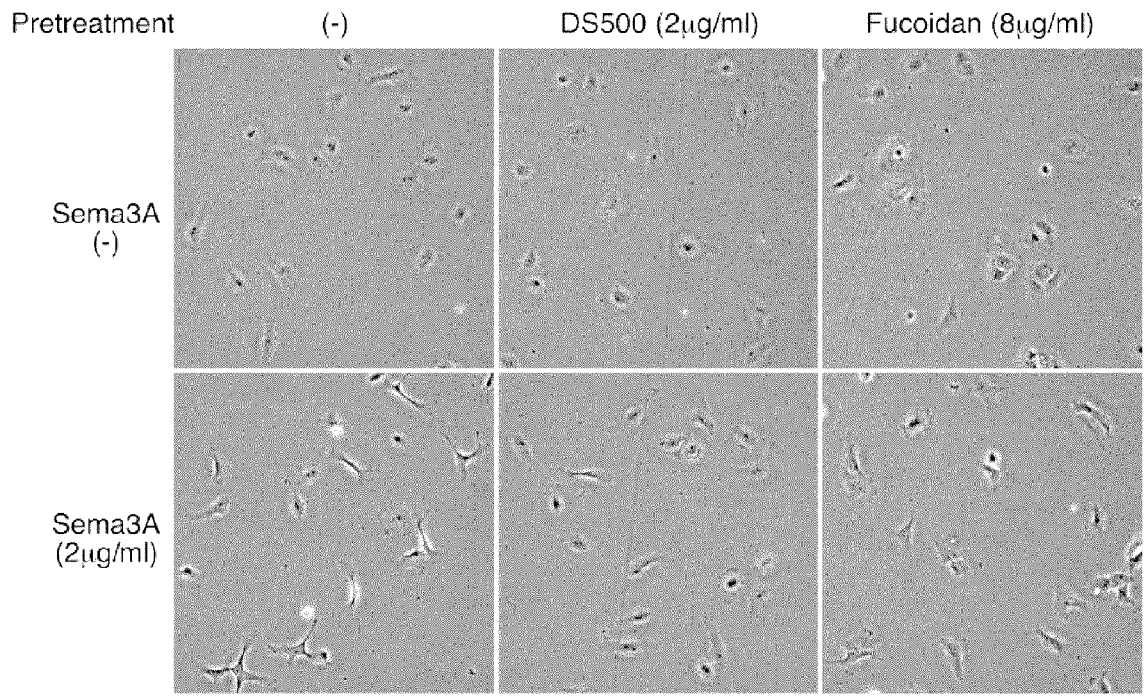

Since DS500 and Fucoidan selectively promote NRP1 and SREC-I internalization in HUVEC (FIGS. 1 and 4) under remarkably similar conditions (concentration, temperature and length of incubation), it was tested whether the two polysaccharide-induced effects were linked. After incubation with polysaccharides (37° C., 1 hour) and permeabilization, it was found that DS500 and Fucoidan, but not heparin or ChoSul A, promoted the internalization of SREC-I and NRP1; importantly, it was found that internalized NRP1 and SREC-I co-localize in structures (FIG. 5A, right panels, yellow) that were identified as lysosomes (FIGS. 2B and 4E). It was directly tested whether DS500 can bridge SREC-I and NRP1 by using an ELISA-based assay in which SREC-I/Fc or control IgG1 is immobilized onto the well and NRP1/Fc is then added with DS500 at varying concentrations. As shown in FIG. 5B, it was found that DS500 dose-dependently promotes the binding of NRP1 to SREC-I (open circles), but not to IgG1 (closed circles); maximal NRP1 binding to SREC-I occurred at the DS500 concentration of 500 ng/ml (FIG. 6B upper panel). Using DS500 at 500 ng/ml, the binding of NRP1 to immobilized SREC-I was dependent on NRP-1 concentration (FIG. 5B lower panel left); control B7-1/Fc minimally bound to SREC-I or IgG1 (FIG. 5B lower panel right). Among the polysaccharides tested, DS500 and to a lower degree Fucoidan promoted NRP1 binding to SREC-I, whereas the other polysaccharides were minimally effective (FIG. 5C). Together, these results indicate that DS500 and Fucoidan can bridge NRP1 to SREC-I and induce their coordinate internalization from the endothelial cell-surface to the cytoplasm where NRP1 and SREC-I co-localize.

Figure 5D:
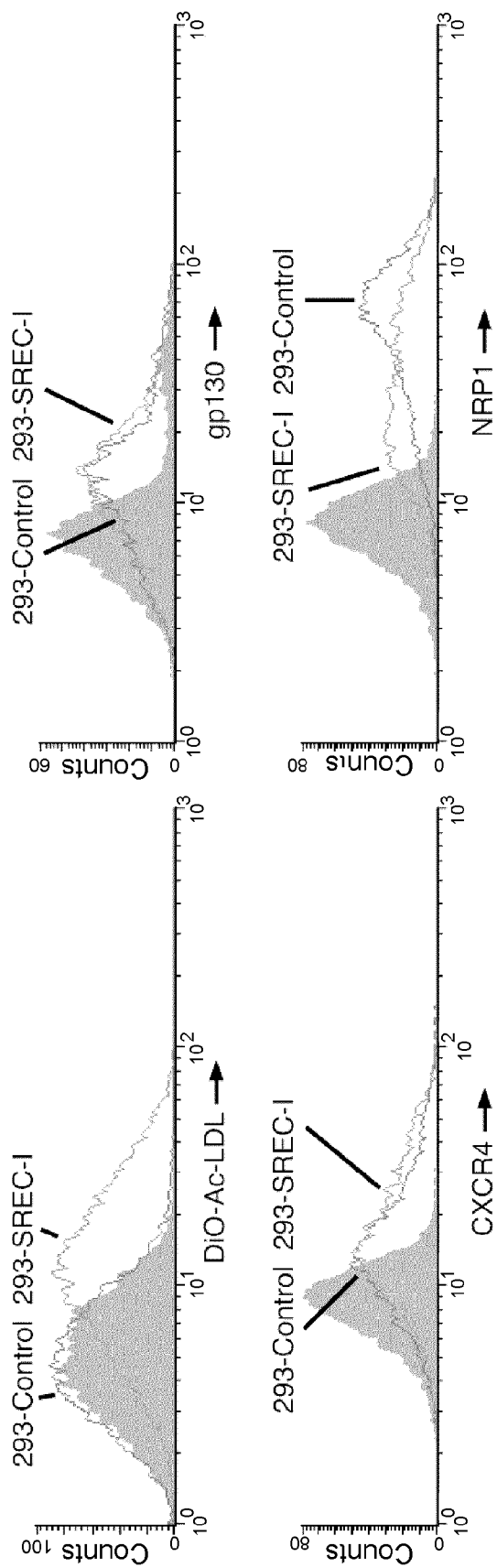

To further define the role of SREC-I in NRP1 internalization, SREC-I was expressed in human 293 cells, which do not express endogenous scavenger receptors, but express gp130, CXCR4 and NRP1. As shown in FIG. 5D, control 293 cells did not uptake DiO-Ac-LDL, but 293-SREC-I cells could uptake DiO-Ac-LDL, indicative of SREC-I function (upper left). An analysis of cell-surface gp130, CXCR4 and NRP1 showed that levels of gp130 (upper right) and CXCR4 (lower left) were similar in control and SREC-1-transfected 293 cells. By contrast, cell-surface NRP1 was significantly reduced in 293-SREC-I cells compared with control 293 cells (FIG. 5D lower right). DS500 induced only minimal further reduction of cell-surface NRP1 levels in 293-SREC-I cells, suggesting that forced expression of SREC-I alone reduces cell-surface NRP1 in this experimental system.

Example 7

Treatment of Endothelial Cells with DS500 or Fucoidan Blocks Sema3A and $VEGF_{165}$ Function This example describes exemplary procedures for determining that DS500 or Fucoidan block Sema3A and $VEGF_{165}$ from binding to their cognate receptors.

Figure 1D:
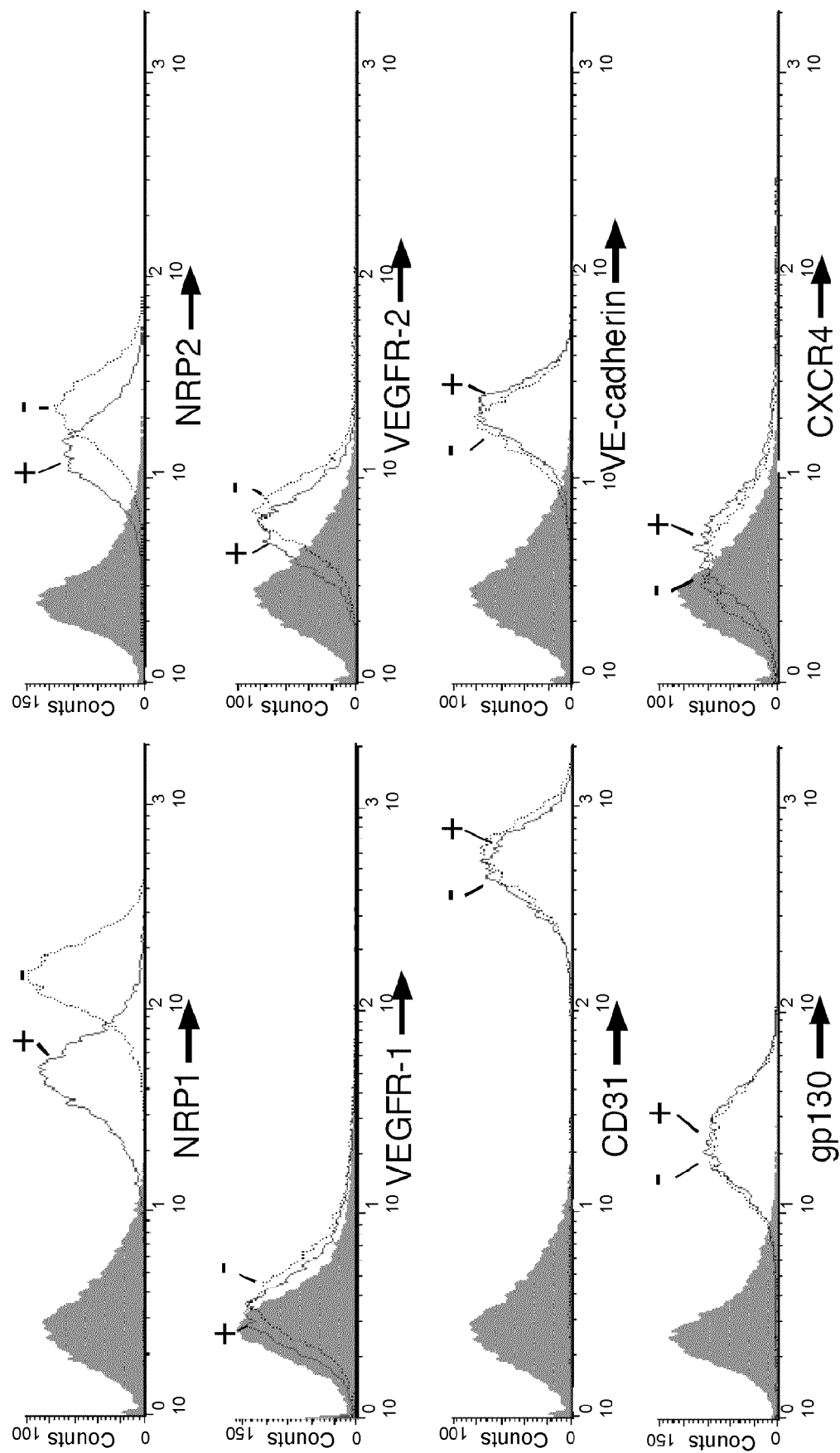
Figure 1E:
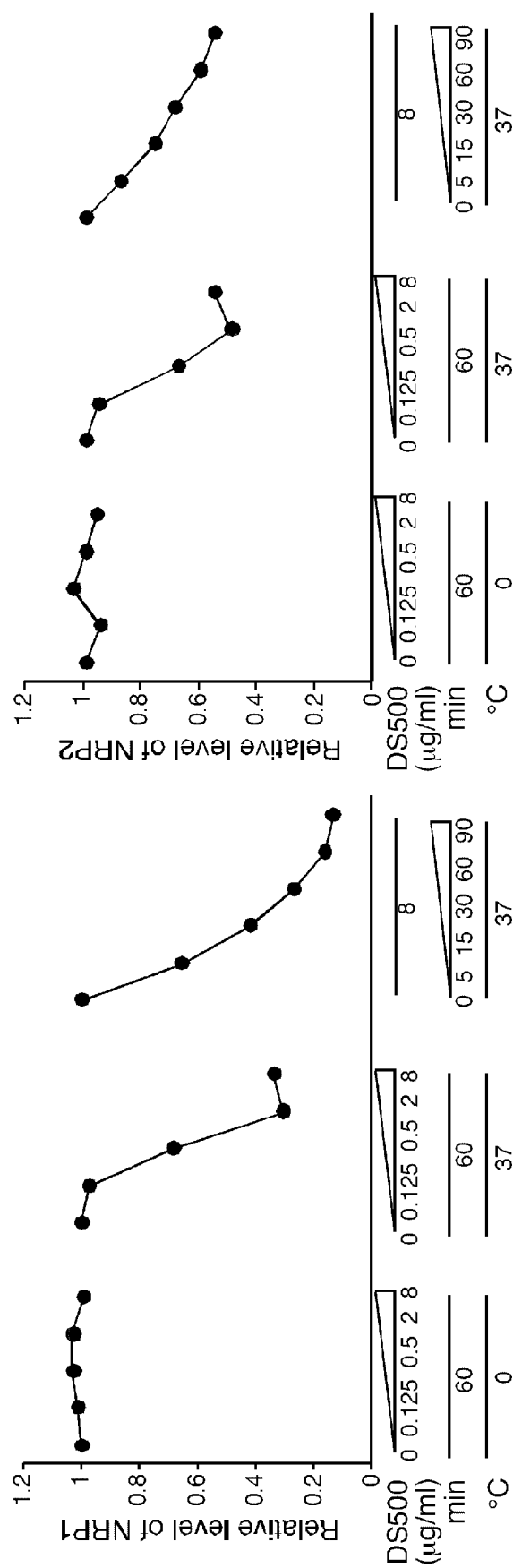

To examine the potential functional significance of the reduction of NRP1, NRP2, VEGFR-1 and VEGFR-2 induced by DS500 and Fucoidan (FIGS. 1C-E). As shown in FIG. 6A, pretreatment with DS500 followed by cell washing dose- and time-dependently inhibited the binding of Sema3A to HUVEC. Conversely, pretreatment with heparin, ChoSul A and dextran (all at 8 µg/ml for 90 minutes) did not affect binding of Sema3A to HUVEC (FIG. 6A filled triangle, square and diamond). Fucoidan also inhibited the binding of Sema3A to HUVEC (FIG. 6A open circle).

Figure 6C:
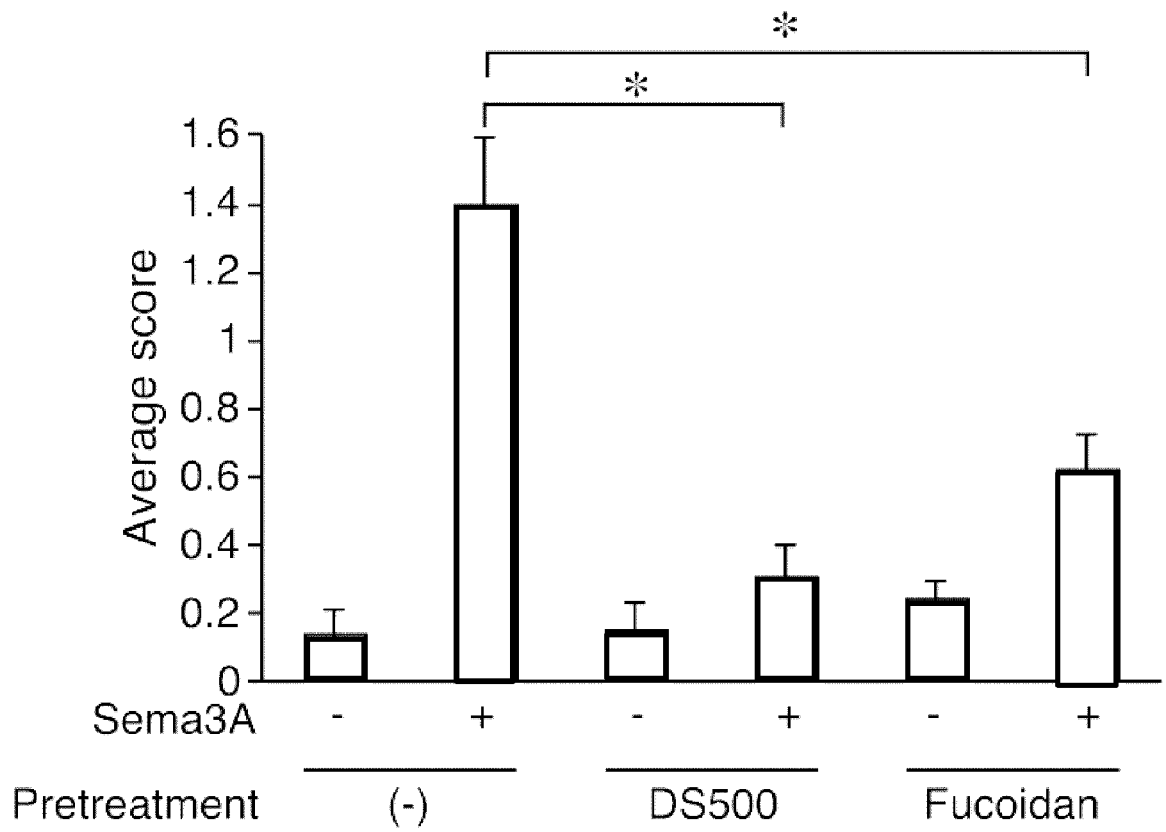
Figure 6D:
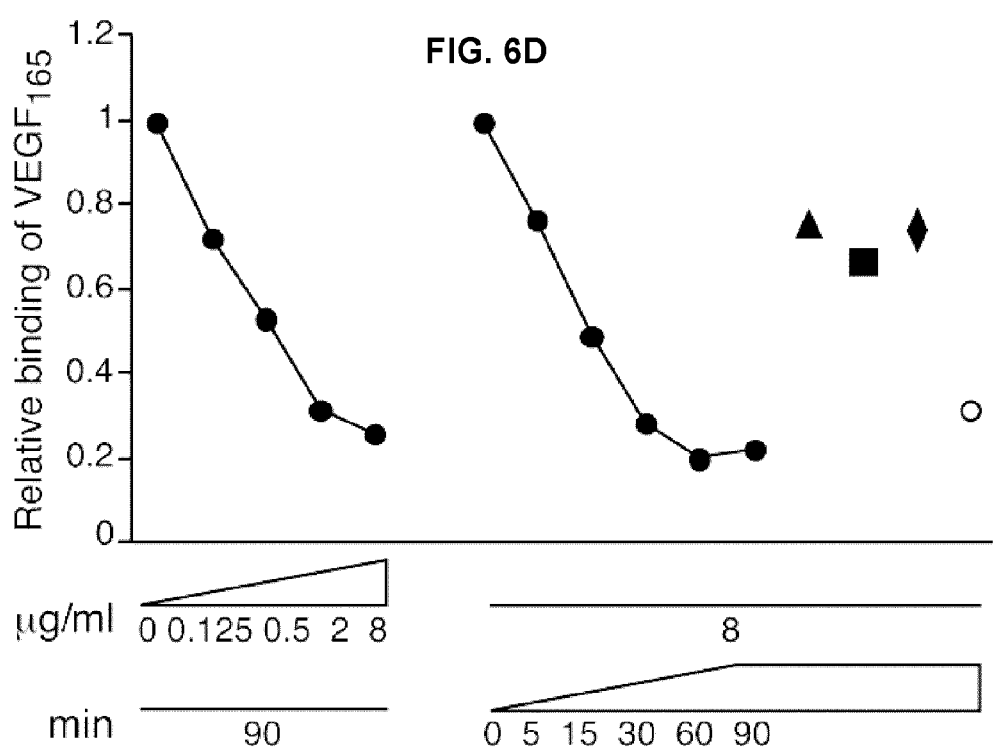
Figure 6E:
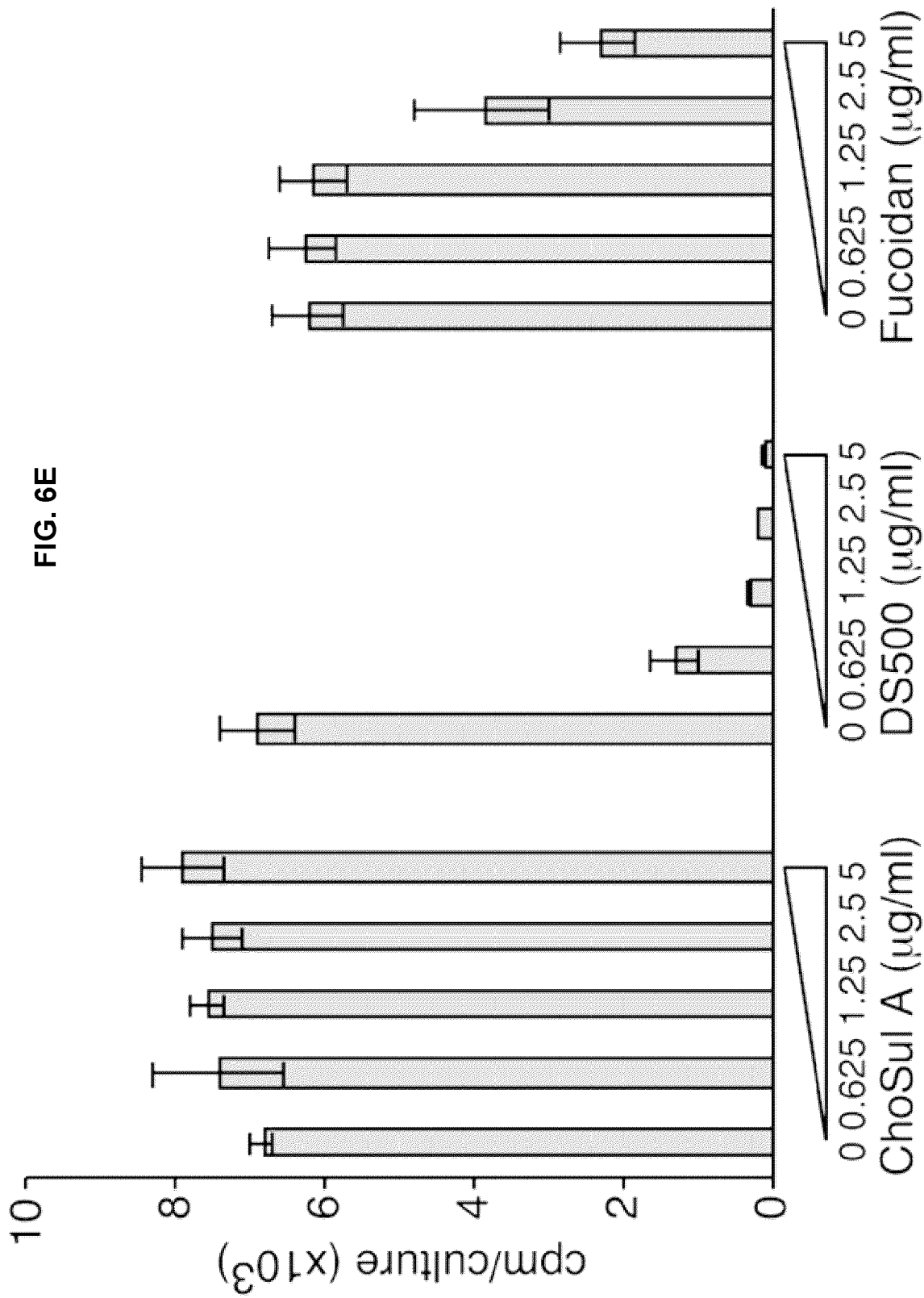

Endothelial cells spread lamellipodia when placed onto a fibronectin-coated glass surface and Sema3A is known to induce retraction of these lamellipodia. It was found that Sema3A induces minimal retraction of lamellipodia in HUVEC that were pretreated with DS500 or Fucoidan, indicative that these polysaccharides can block this function of Sema3A (FIG. 6B). The degree of retraction in 3 independent trials (performed as described in Narazaki and Tosato, *Blood* 107:3892-3901, 2006) demonstrated that DS500 and Fucoidan reduce significantly Sema3A-induced lamellipodia retraction in HUVEC (FIG. 6C). It was also found that pretreatment with DS500 dose- and time-dependently blocked the binding of $VEGF_{165}$ to HUVEC, whereas pretreatment with heparin, ChoSul A and dextran did not affect $VEGF_{165}$ binding to these cells (FIG. 6D). Fucoidan also inhibited $VEGF_{165}$ binding to HUVEC (FIG. 6D). The effect of polysaccharides on $VEGF_{165}$-induced proliferation of endothelial cells was also tested. As shown in FIG. 6E, DS500 and to a lower degree Fucoidan inhibited HUVEC proliferation in response to VEGF$_{165}$, whereas ChoSul A was minimally effective.

Example 8

Fucoidan Inhibits Angiogenesis In Vivo

This example describes methods for determining the in vivo effects of Fucoidan and DS500.

Figure 7A:
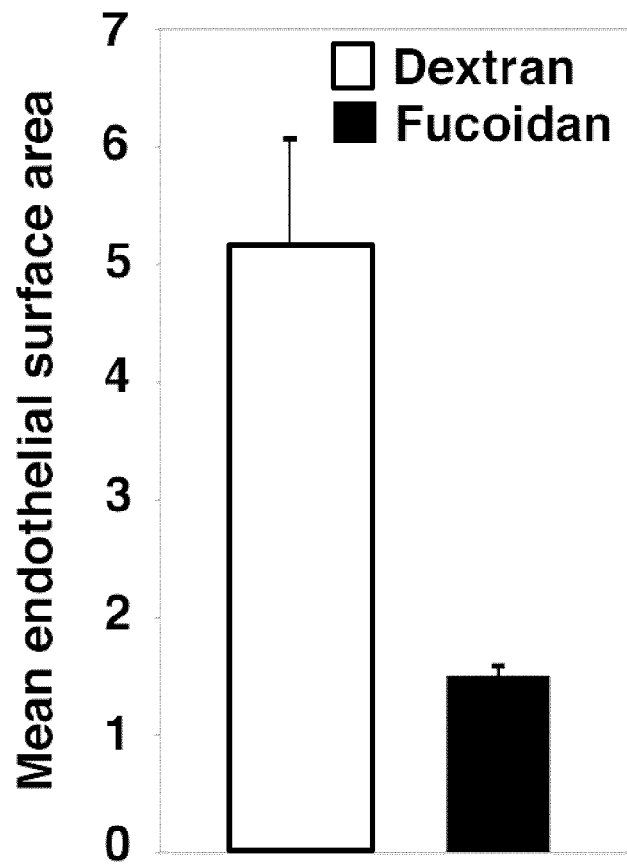
Figure 7B:
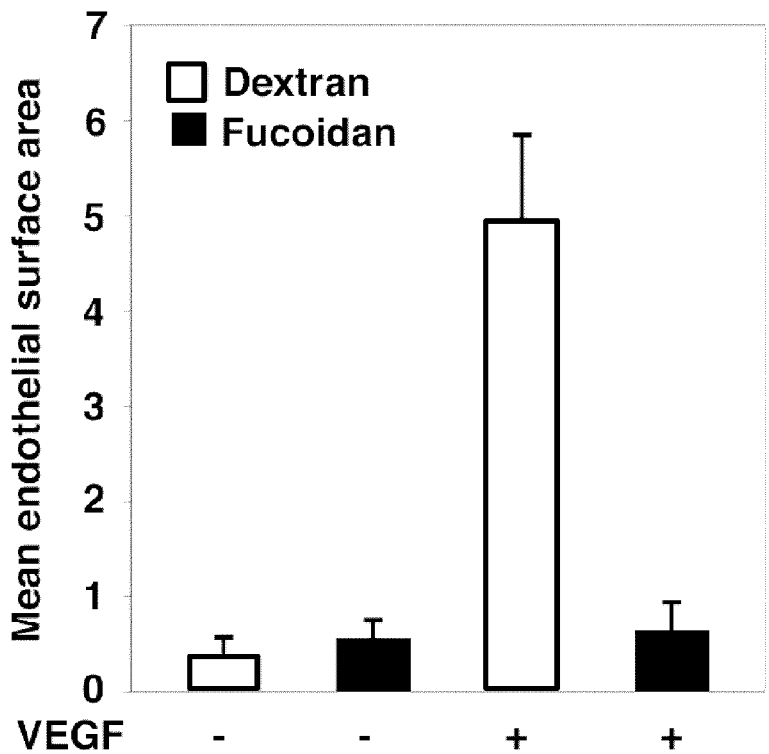

The effects of Fucoidan and DS500 on VEGF-induced angiogenesis in vivo was tested using MATRIGEL™ plugs containing VEGF (0 or 150 ng/ml) plus heparin (0 or 0.5 µg/ml) s.c. transplanted in mice (C57BL/6J). The groups of mice (5 mice/group) were treated with Fucoidan, DS500 or control non-sulfated dextran (1 mg/mouse i.p/day). DS500 treatment induced death in 8/10 animals; Fucoidan and dextran were well tolerated. The endothelial cell density (CD31/PECAM staining, measured digitally with IP-lab software) was significantly (P=0.003) reduced in VEGF-supplemented plugs from mice treated with Fucoidan compared to the controls (FIG. 7A). Plugs without VEGF supplementation displayed minimal cell infiltration with or without systemic treatment. Using BALB/cAnNCr mice (6 mice/group), it was confirmed that MATRIGEL™ plugs from the Fucoidan-treated group contained a significantly (P<0.001) reduced endothelial cell infiltration compared to the control-treated group (FIG. 7B), providing evidence that Fucoidan inhibits VEGF-induced neovascularization.

Figure 7C:
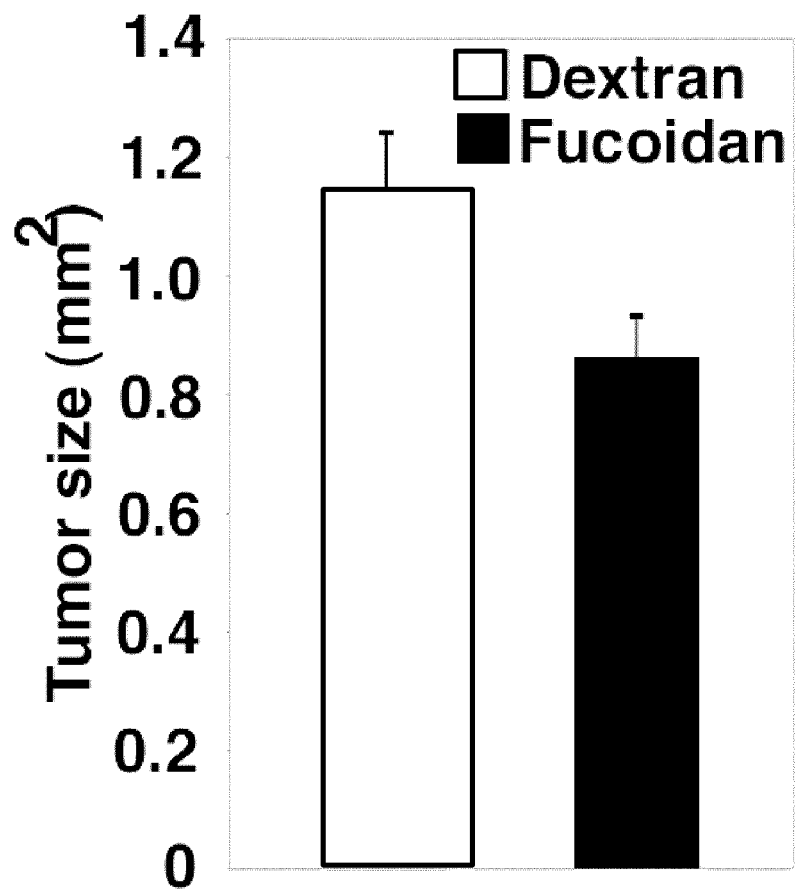
Figure 7D:
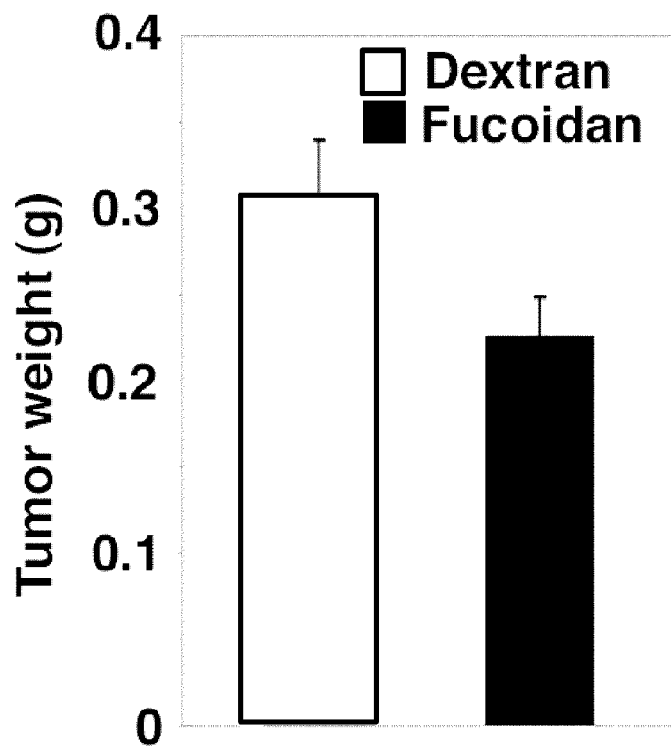

To evaluate the effects of Fucoidan on tumor angiogenesis, a model was selected in which the plasma-cell tumor line MOPC 315 (BALB/c-derived), which expresses VEGF, was inoculated s.c. (10$^7$ cells/mouse) into BALB/cAnNCr mice. Under these conditions, MOPC315 cells give rise to rapidly growing and highly vascularized tumors at the injection site. Groups of mice were treated (15 mice/group) with either Fucoidan or control non-sulfated dextran (1 mg/mouse i.p./day). The size (1.139±0.1 mm$^2$; mean±SEM) and weight (0.31±0.03 g) of tumors from the Fucoidan-treated mice were significantly (P=0.032 and P=0.047, respectively) reduced compared to the size (0.86±0.07 mm$^2$) and weight (0.23±0.02 g) of control tumors (FIGS. 7C and D). Control tumor tissues were highly vascular as assessed by CD31 staining whereas tumor tissues from Fucoidan-treated mice were remarkably low in CD31 staining, even at the growing margins (representative images in FIG. 7E). Quantitative analysis revealed that tumor tissues from control mice contained a significantly (P=0.007) greater CD31-positive area compared to Fucoidan treated mice (FIG. 7F). Thus, these results indicate that Fucoidan reduces angiogenesis in distinct in vivo model systems.

Example 9

Effects of Oligonucleotides on Cell-Surface NRP1

This example describes exemplary methods for determining that oligonucleotides bind NRP1 on a cell surface.

In addition to binding Ac-LDL, oxidized LDL and polysaccharides, scavenger receptors have previously been shown to bind DNA (see, for example Jeannin et al., *Curr Opin Immunol* 20, 530-537, 2008; Kimura et al., *J Biochem* 116, 991-994, 1994; Meylan et al., *Nature* 442, 39-44, 2006). Short poly (G) sequences have been shown to confer binding to scavenger receptors when linked to other DNA molecules (Prasad et al., *Antimicrob Agents Chemother* 43, 2689-2696, 1999). Based on the fact that poly(G) or oligo(G) have a polyanionic structure like sulfated polysaccharides and may thus serve as ligands for certain scavenger receptors, was examined whether poly(G) or oligo(G) might display the NRP1 internalization-promoting property of other polyanionic scavenger receptor ligands, such as the sulfated polysaccharide DS500 or fucoidan.

A panel of synthetic polyribonucleotides and oligonucleotides was tested for their ability to promote internalization of NRP1 and the scavenger receptor SREC-1 in endothelial cells. The oligonucleotides were custom synthesized and purified to a high degree of homogeneity by high performance liquid chromatography (HPLC) at Sigma Genosys (SIGMA ALDRICH®). The compounds tested are listed in Table 1.

TABLE 1

| Oligonucleotides Tested | |
|---|---|
| Polyribonucleotides | polyadenosine (poly(A)) |
| | polyguanosine (poly(G)) |
| | polycytidine (poly(C)) |
| Oligodeoxynucleotides | oligodeoxyadenosine 18mer (A18) |
| | oligodeoxythymidine 18mer (T18) |
| | oligodeoxyguanosine 18mer (G18) |
| | phosphorothioate oligodeoxyguanosine 18mer (sG18) |
| | oligodeoxycytidine 18mer (C18) |
| | 2'-deoxyguanosine 5'-monophosphate sodium salt hydrate (dGMT) |

Figure 8:
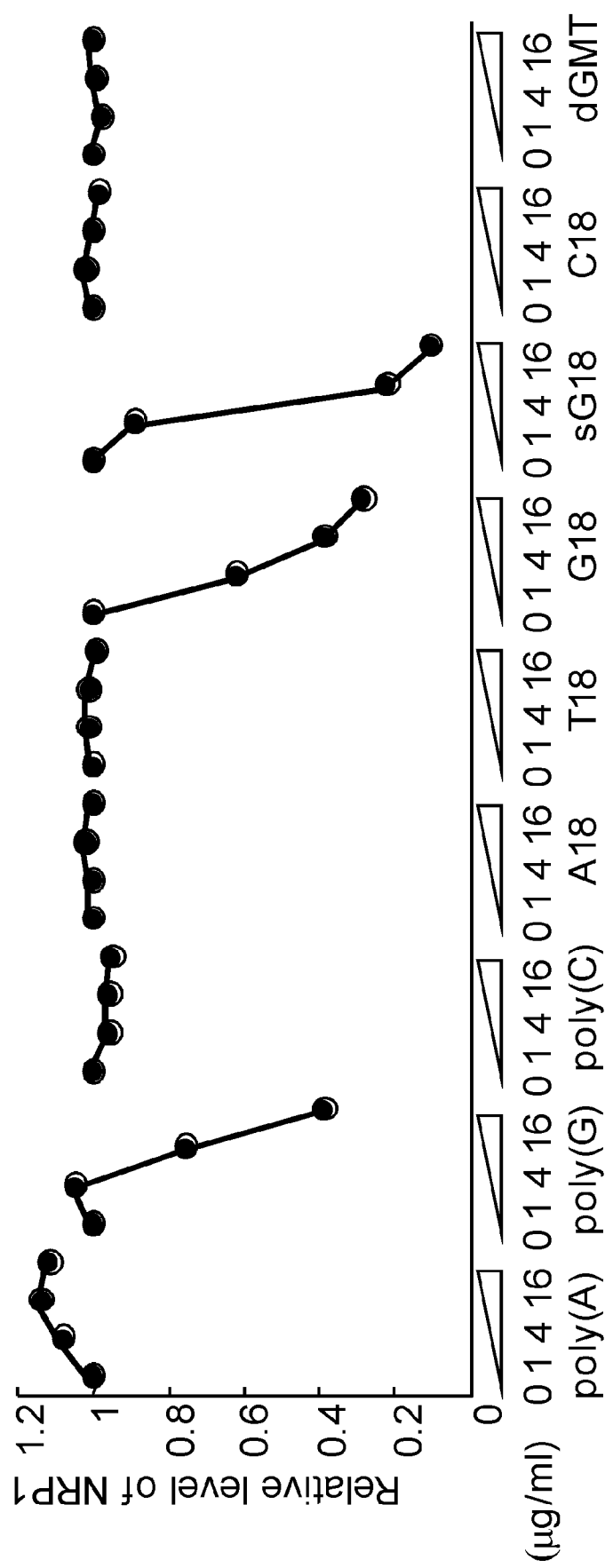
FIG. 8 is a set of line graphs showing the effects of polyribonucleotides and oligodeoxynucleotides on cell surface expression of NRP1. HUVEC were pre-incubated (37° C., 1 hour) with polyribonucleotides and oligodeoxynucleotides (1-16 μg/ml) at the indicated concentrations.

HUVEC were incubated at 37° C. for 1 hour with or without the polyribonucleotide polyadenosine (poly(A)), polyguanosine (poly(G)), polycytidine (poly(C)); or with the oligodeoxynucleotide oligodeoxyadenosine 18mer (A18), oligodeoxythymidine 18mer (T18), oligodeoxyguanosine 18mer (G18), phosphorothioate oligodeoxyguanosine 18mer (sG18), oligodeoxycytidine 18mer (C18) and 2'-deoxyguanosine 5'-monophosphate sodium salt hydrate (dGMT). After washing, the levels of cell surface NRP-1 were measured by flow cytometry. Poly (G), G18 and sG18 dose-dependently reduced cell-surface levels of NRP1 in HUVEC, whereas all other compounds did not (FIG. 8). Interestingly, comparative analysis of effects showed that poly(G), G18 and sG18 were more potent than DS500 or fucoidan at reducing cell surface levels of NRP1 on HUVEC.

Figure 9:
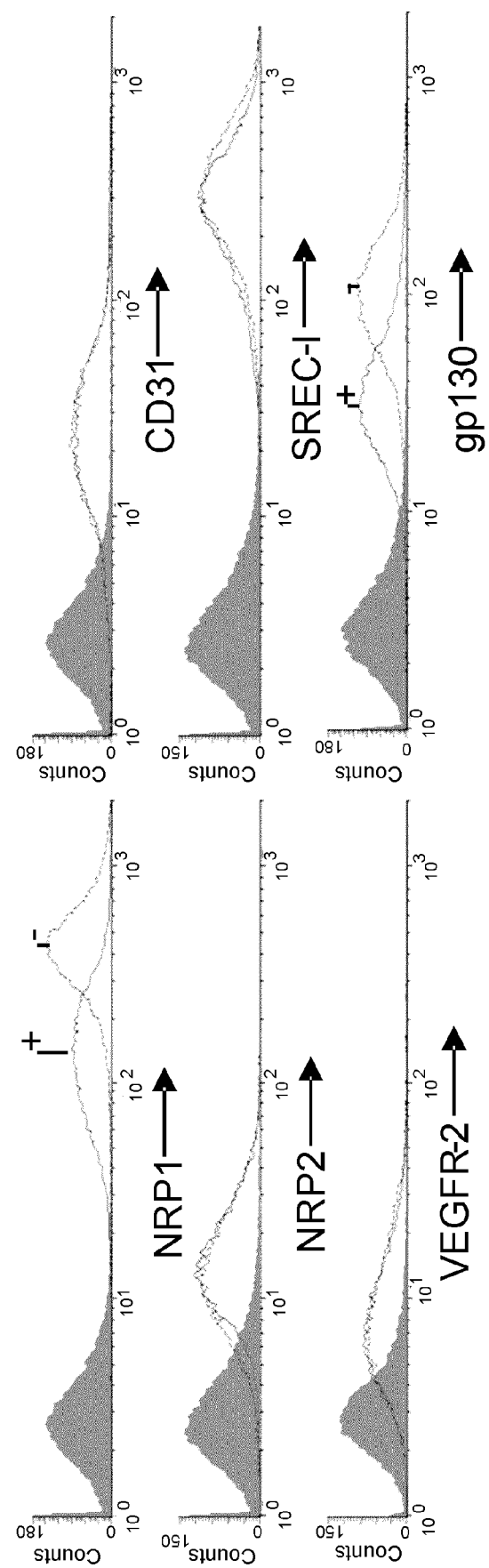
FIG. 9 is a set of histograms from a flow cytometry analysis of the effects of poly(G) on levels of cell surface molecules NRP1, NRP2, VEGFR-2, gp130, CD31 and SREC-I. HUVEC were incubated (37° C., 1 hour) with (+) or without (−) poly(G). Shaded graphs reflect control staining.

The specificity of poly(G) effects on NRP1 surface levels was tested by determining its effects on cell surface levels of other molecules expressed by HUVEC. Unlike the reduction of NRP1, which was consistently observed, cell surface levels of NRP2, VEGFR2, gp130 and CD31 were not reduced in HUVEC incubated at 37° C. for 1 hour with poly(G) (64 µg/ml) (FIG. 9). Similar to the reduction in cell surface levels of NRP1, cell surface levels of SREC-1 were markedly reduced under the same conditions that led to NRP1 reduction (FIG. 9). G18 and sG18 displayed similar effects to those of poly(G). These results indicate that poly(G), G18 and sG18 reduce cell surface levels of NRP1 and SREC-1 in HUVEC, but not the levels of other surface molecules expressed by these cells.

Figure 10:
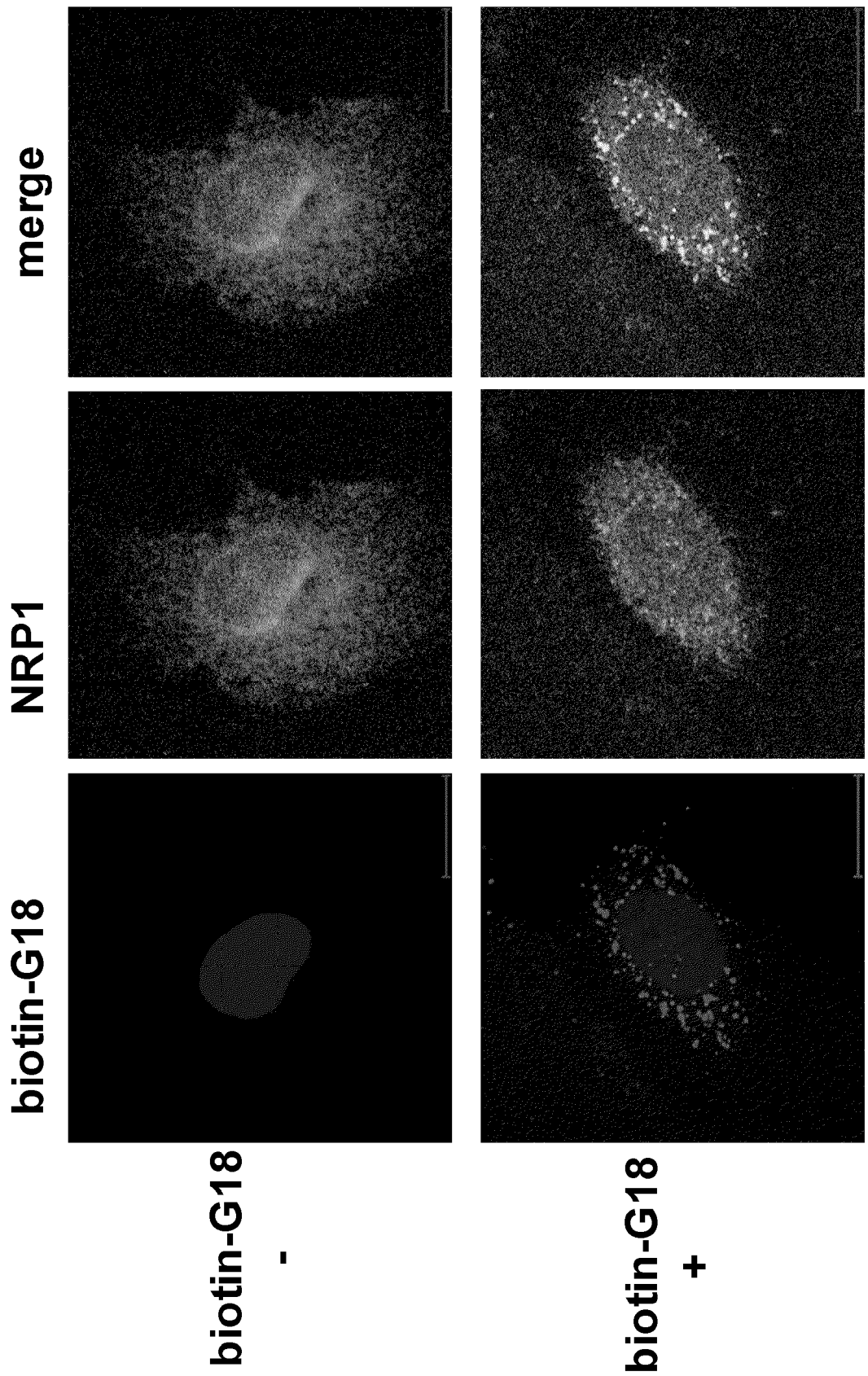
FIG. 10 is a digital image of HUVEC treated (37° C., 1 hour) with or without biotin-G18 (16 μg/ml), stained for NRP1, biotin-G18 and Hoechst 33342, fixed and observed by an LSM510 confocal microscope equipped with a PLAN-NEOFLUAR® 40×1/1/3 objective lens (Carl Zeiss). Images reflect the merging of fluorescent NRP1, biotin-G18 and Hoechst 33342 images. Scale bar 20 μm.

It was evaluated whether the reduction of cell surface NRP1 was attributable to its internalization from the cell surface to the intracellular compartment. HUVEC were incubated at 37° C. for 1 hour with 16 µg/ml biotin-labeled G18; after washing, the cells were stained for NRP1 using anti-NRP1 monoclonal antibody followed with anti-mouse Alexa-488; biotin-G18 was identified with streptavidin-Alexa-546. By confocal microscopy, NRP1 and biotin-G18 was detected inside HUVEC displaying a dot like pattern. In addition, it was found that NRP1 and biotin-G18 colocalize at least in part in these dot-like structures (FIG. 10). These results provide evidence for coordinate internalization of NRP1 and biotin-G18 in HUVEC.

Figure 11:
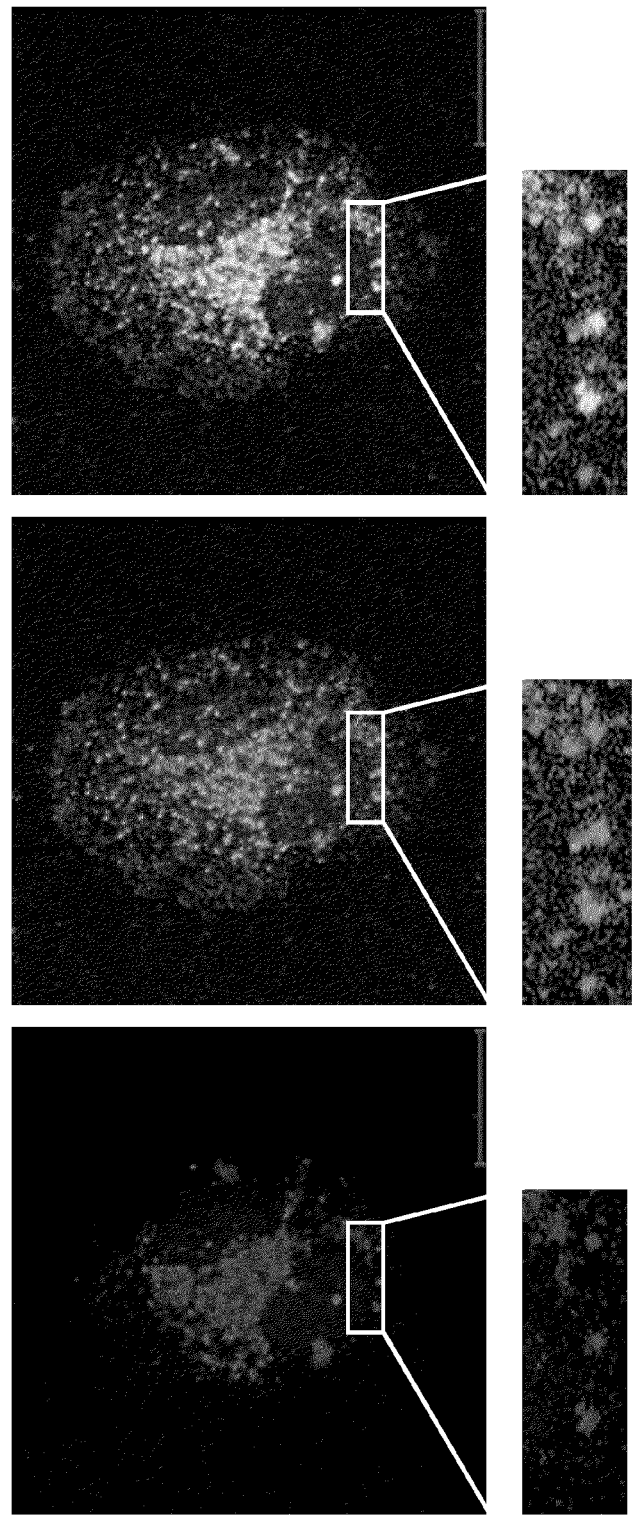
FIG. 11 is a digital image of HUVEC incubated (37° C., 1 hour) with sG18 (16 μg/ml), stained for SREC-I, NRP1 and Hoechst 33342, fixed and observed by a confocal microscope equipped with a PLAN-NEOFLUAR® 40×1/1/3 objective lens (Carl Zeiss). Images reflect the merging of fluorescent SREC-I, NRP-1 and Hoechst 33342 slice images. Scale bar 20 μm.

It was previously established that DS500 and fucoidan can promote the internalization of NRP1 by bridging NRP1 to the scavenger SREC-I receptor and others have previously demonstrated that polyribonucleotides such as poly(G) can bind to certain scavenger receptors on other cells. It was tested whether phosphorothioate G18 (sG18) can similarly bridge NRP1 to SREC-I and promote their internalization. To this end, HUVEC were incubated at 37° C. for 1 hour with sG18 (16 µg/ml) and then examined by confocal microscopy. NRP1, identified by anti-NRP1 antibody and SREC-I, identified by anti-SREC-I antibody, were visualized inside the HUVEC and were found to co-localize at least in part (FIG. 11). This result suggested that G18 can promote the coordinate internalization of NRP1 and SREC-I.

Figures 12A, 12B, 12C:
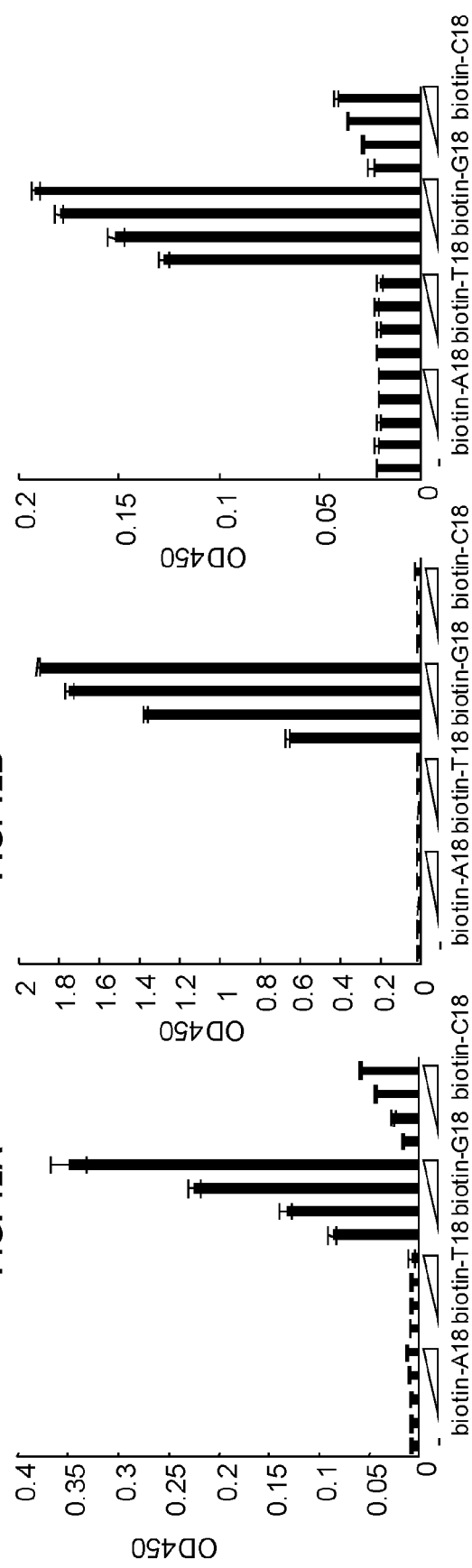
FIG. 12A-12C is a set of bar graphs showing the binding of biotin-labeled oligos to immobilized NRP1 (FIG. 12A) and immobilized SREC-I (FIG. 12B). The bridging of NRP1 to SREC-I in the presence of biotin-oligos is shown in (FIG. 12C). NRP1 was added to SREC-1/Fc-coated wells with or without biotin-oligos (0.25, 1, 4 or 16 μg/ml). Binding was detected by absorbance at OD450. The results reflect the means (±SD) of 3 trials.

To test whether this effect might be attributable to G18 bridging the two molecules, an ELISA-based binding assay was used. In this assay, recombinant SREC-I/Fc (1 µg/ml, 50 ml/well) was immobilized onto microtiter wells. After washing to remove unbound SREC-I, 2 µg/ml recombinant NRP1/Fc was added to SREC-1-coated wells in the presence of biotin-labeled A18, T18, G18 or C18 (0.25, 1, 4 or 16 µg/ml). The binding of His-tagged NRP1/Fc to the plate was measured by absorbance after addition of a mouse anti-His monoclonal antibody (INVITROGEN™ 1/5000) followed by a secondary HRP conjugated anti-mouse IgG antibody (GE Healthcare 1/5000). Since NRP1/Fc includes a His-tag whereas SREC-I/Fc does not, the anti-His monoclonal antibody selectively detected bound NRP1. As shown in FIG. 12C, dose-dependent binding of NRP1 was found only when Biotin-labeled G18 (0.25, 1, 4 or 16 µg/ml) was added to the wells. Little or no NRP1 binding to SREC-I when either no oligonucleotide was added or one of the other biotin-labeled A18, T18 or C18 were added at the same concentrations (0.25, 1, 4 or 16 µg/ml). In control binding trials, it was confirmed that biotin-labeled G18, but not A18, T18 or C18 dose-dependently bound to NRP1 immobilized onto the plate (FIG. 12A) and to SREC-I immobilized to the plate (FIG. 12B). Additionally, biotin-labeled G18 did not bind to albumin or to control human IgG1 immobilized on to the plate.

Figure 13:
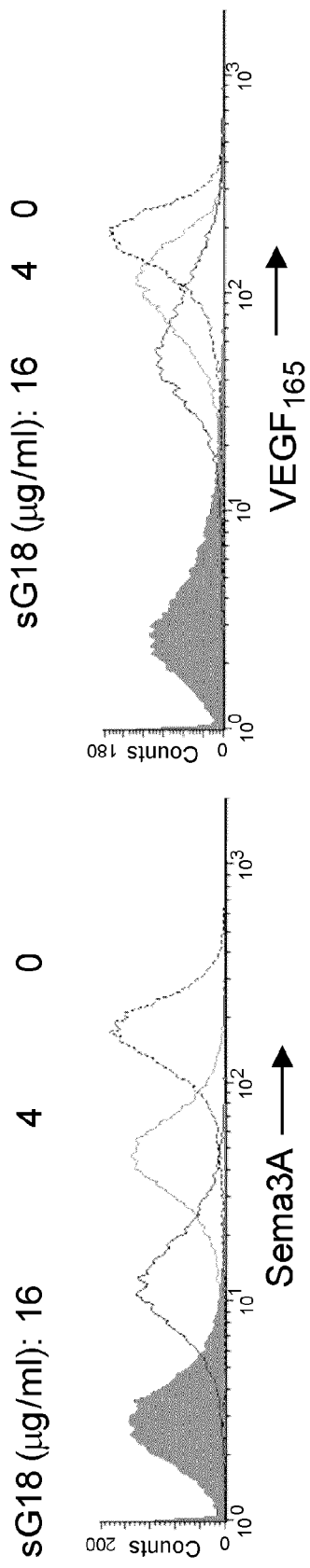
FIG. 13 is a set of histograms from a flow cytometry analysis showing the effects of oligo(G) on Sema3A and VEGF165 binding to cells. HUVEC were incubated (37° C., 1 hour) with or without phosphorothioate oligo(G) (sG18) at 4 or 16 μg/ml. After washing, bound Sema3A/Fc or biotin-VEGF165 was detected by flow cytometry.

The results shown in FIGS. 8-12 indicate that oligo(G) can promote the internalization of NRP1 by bridging NRP1 to the scavenger SREC-I receptor on endothelial cells. This should disrupt the binding of the NRP1 ligands Sema3A and VEGF165 to endothelial cells due to receptor internalization. To verify this hypothesis, HUVEC were incubated at 37° C. for 1 hour with or without phosphorothioate G18 (sG18) (4 or 16 µg/ml). Subsequently, the cells were washed and binding of Sema3A/Fc and biotin-labeled VEGF165 tested after incubation at 4° C. for 1 hour. Bound Sema3A/Fc was detected by flow cytometry after staining with FITC-conjugated goat anti-human IgG-Fc; bound VEGF165 was detected by flow cytometry after staining with avidin-FITC. As shown in FIG. 13, sG18-treated HUVEC displayed a dose-dependent reduction of Sema3A (FIG. 13 left) and VEGF165 binding (FIG. 13 right). These results demonstrate that sG18 can interfere with the binding of VEGF165 and Sema3A to endothelial cells. Since sG18 induces the internalization of NRP1 and ligand binding to cognate receptors is required for functional activity, these results predict that sG18 impairs Sema3A and VEGF165 activity in endothelial cells.

Figure 14:
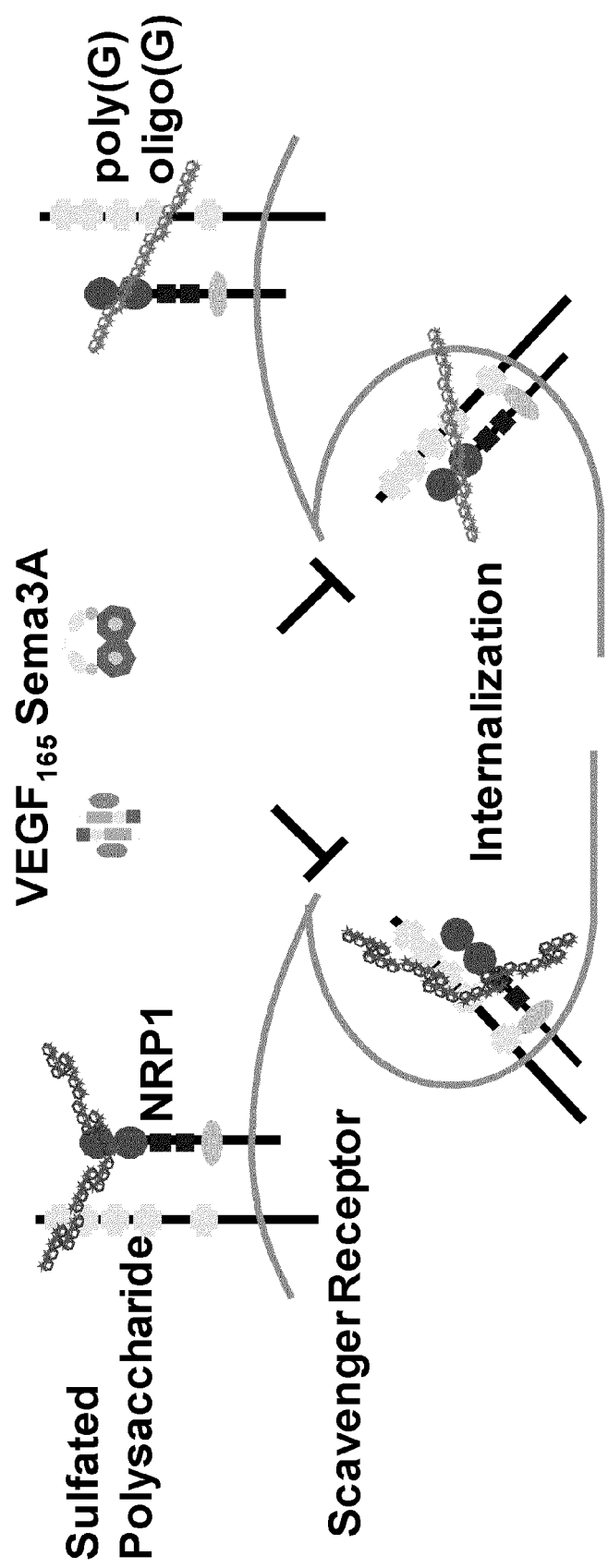
FIG. 14 is a schematic drawing showing the internalization of the receptors NRP1 and SREC-I induced by selected sulfated polysaccharides and poly(G)/oligo(G) nucleotides. Once internalized, NRP1 is no longer present on the cell surface and cannot bind/mediate signaling from the cognate ligands Sema3A or VEGF165.

All together, the results presented provide evidence for a model in which the sulfated polysaccharide fucoidan (and other sulfated polysaccharides) and poly(G)/oligo(G) can bridge the cell surface receptor molecules NRP1 and scavenger receptor SREC-I (FIG. 14). In so doing, selected sulfated polysaccharides and poly(G)/oligo(G) promote the coordinate internalization and subsequent degradation of these receptors. Once internalized, NRP1 is no longer available for binding the cognate ligands VEGF165 and Sema3A and signaling from this binding is impaired. As a consequence, Sema3A and VEGF165 are biologically inactive.

Example 10

Production of Hetero-Bifunctional Ligands for Inducing Internalization of VEGFR-2 and Co-Receptor Neuropilin-1

This example describes exemplary methods for constructing a hetero-bifunctional ligand for the target receptor VEGFR-2 and co-receptor Neuropilin-1.

VEGF-A (the ligand for the receptor VEGFR-2 and co-receptor Neuropilin-1) and Acetylated-LDL (a scavenger ligand which induces the internalization of scavenger receptors) are chemically linked with crosslinkers available commercially from Pierce (Bioconjugate Toolkit Reagents) to tag VEGF-A and Acetylated-LDL with two different hetero-bifunctional linkers (A and B). After derivation of VEGF-A-(linker A) and Acetylated-LDL-(linker B), these two molecules are linked together. As a result, the final product is a hetero-bifunctional ligand composed of (VEGF-A)-(linker A)-(linker B)-(Acetylated-LDL). The efficacy of this hetero-bifunctional ligand in inhibiting angiogenesis is tested using the procedures set forth in Examples 1-9.

Example 11

Production of Hetero-Bifunctional Ligands for Inducing Internalization of CCR5

This example describes exemplary methods for constructing a hetero-bifunctional ligand for the target receptor CCR5.

An antibody or a ligand for the cell surface receptor CCR5 is chemically linked to a internalizing receptor ligand, such as Acetylated-LDL, with crosslinkers available commercially from Pierce (Bioconjugate Toolkit Reagents). After derivation of the antibody or a ligand for the cell surface receptor CCR5 and an internalizing receptor ligand, such as Acetylated-LD are linked together. As a result, the final product is a hetero-bifunctional ligand composed of (antibody or a ligand for the cell surface receptor CCR5)-(linker)-(internalizing receptor ligand, such as Acetylated-LDL). Such a hetero-bifunctional ligand can be used to induce the internalization of CCR5 and thereby inhibit or treat an HIV infection. The efficacy of such a hetero-bifunctional ligand can be assessed using the procedures described in Examples 12 and 13.

Example 12

Method of Inhibiting HIV Attachment, Infection or Replication

This example describes exemplary methods for inhibiting HIV infection or replication using a hetero-bifunctional ligand.

Using a hetero-bifunctional ligand (for example the hetero-bifunctional ligand described in Example 11), that binds to and induces the internalization of a receptor used by HIV to gain entry into a cell, HIV infection, replication or a combination thereof can be reduced or inhibited by contacting a cell with an effective amount of the hetero-bifunctional ligand. The cell can be in vivo or in vitro.

Example 13

Treatment of HIV in a Subject

This example describes exemplary methods for treating or inhibiting an HIV infection in a subject, such as a human subject by administration of one or more hetero-bifunctional ligands that induce the internalization of a receptor used by HIV to bind a cell or gain entry into a cell. Although particular methods, dosages and modes of administrations are provided, one skilled in the art will appreciate that variations can be made without substantially affecting the treatment.

HIV, such as HIV type 1 (HIV-I) or HIV type 2 (HIV-II), can be treated by administering a therapeutically effective amount of a hetero-bifunctional (such as the hetero-bifunctional ligand described in Example 10) that induces the internalization of a receptor used by HIV to bind a cell or gain entry into a cell, for example by effectively hiding this receptor from the virus, thereby reducing or inhibiting HIV infection, replication or a combination thereof.

Briefly, the method can include screening subjects to determine if they have HIV, such as HIV-I or HIV-II. Subjects having HIV are selected. In one example, subjects having increased levels of HIV antibodies in their blood, as detected with an enzyme-linked immunosorbent assay, Western blot, immunofluorescence assay or nucleic acid testing, including viral RNA or proviral DNA amplification methods are selected. In one example, a clinical trial would include half of the subjects following the established protocol for treatment of HIV (such as a highly active antiretroviral therapy). The other half would follow the established protocol for treatment of HIV (such as treatment with highly active antiretroviral compounds) in combination with administration of the agents including a hetero-bifunctional ligand that induces the internalization of a receptor used by HIV to bind a cell or gain entry into a cell. In another example, a clinical trial would include half of the subjects following the established protocol for treatment of HIV (such as a highly active antiretroviral therapy). The other half would receive an agent including a hetero-bifunctional ligand that induces the internalization of a receptor used by HIV to bind a cell or gain entry into a cell.

Screening Subjects

In particular examples, the subject is first screened to determine if they have HIV. Examples of methods that can be used to screen for HIV include a combination of measuring a subject's CD4+ T cell count and the level of HIV in serum blood levels.

In some examples, HIV testing consists of initial screening with an enzyme-linked immunosorbent assay (ELISA) to detect antibodies to HIV, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (for example, Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive occasionally provide an indeterminate Western blot result, which may be either an incomplete antibody response to HIV in an infected person or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (for example, viral RNA or proviral DNA amplification method) can also help diagnosis in certain situations.

The detection of HIV in a subject's blood is indicative that the subject has HIV and is a candidate for receiving the therapeutic compositions disclosed herein. Moreover, detection of a CD4+ T cell count below 350 per microliter, such as 200 cells per microliter, is also indicative that the subject is likely to have HIV.

Pre-screening is not required prior to administration of the therapeutic compositions disclosed herein (such as those that include a hetero-bifunctional ligand that induces the internalization of a receptor used by HIV to bind a cell or gain entry into a cell.).

Pre-Treatment of Subjects

In particular examples, the subject is treated prior to diagnosis of HIV with the administration of a therapeutic agent that includes one or more of the disclosed a hetero-bifunctional ligands that induce the internalization of a receptor used by HIV to bind a cell or gain entry into a cell. In some examples, the subject is treated with an established protocol for treatment of HIV (such as a highly active antiretroviral therapy) prior to treatment with the administration of a therapeutic agent that includes one or more of the disclosed a hetero-bifunctional ligands that induce the internalization of a receptor used by HIV to bind a cell or gain entry into a cell. However, such pre-treatment is not always required and can be determined by a skilled clinician.

Administration of Therapeutic Compositions

Following subject selection, a therapeutic effective dose of the agent including a hetero-bifunctional ligand that induces the internalization of a receptor used by HIV to bind a cell or gain entry into a cell is administered to the subject (such as an adult human or a newborn infant either at risk for contracting HIV or known to be infected with HIV). For example, a therapeutic effective dose of an agent including one or more of the hetero-bifunctional ligands that induce the internalization of a receptor used by HIV to bind a cell or gain entry into a cell. Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal or subcutaneous.

The amount of the composition administered to prevent, reduce, inhibit, and/or treat HIV or a condition associated with it depends on the subject being treated, the severity of the disorder and the manner of administration of the therapeutic composition. Ideally, a therapeutically effective amount of an agent is the amount sufficient to prevent, reduce, and/or inhibit, and/or treat the condition (for example, HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly or monthly repeated administration protocol). In one example, therapeutic agents that include one or more hetero-bifunctional ligands that induce the internalization of a receptor used by HIV to bind a cell or gain entry into a cell are administered intravenously to a human. As such, these compositions may be formulated with an inert diluent or with a pharmaceutically acceptable carrier.

Therapeutic compositions can be taken long term (for example over a period of months or years).

Assessment

Following the administration of one or more therapies, subjects having HIV (for example, HIV-I or HIV-II) can be monitored for reductions in HIV levels, increases in a subjects CD4+ T cell count or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50% or at least 70% in HIV infection, HIV replication or combination thereof. A partial response may also be an increase in CD4+ T cell count such as at least 350 T cells per microliter.

Example 14

In Vitro Testing of Hetero-Bifunctional Ligands

This example describes methods that can be used to test agents for their ability to induce the internalization of specific target receptors. Although particular methods are provided, one skilled in the art would be able to practice other methods, such as the use of different animals, different modes of administration and so forth to test the disclosed hetero-bifunctional ligands.

The ability of a hetero-bifunctional ligand, such as those disclosed herein, to induce the internalization of a target receptor can be assessed using in vitro cellular models, for example, using a cell that expresses both a target receptor and an internalizing receptor. The cell expressing the particular combination of target receptor and internalization receptor is contacted with a hetero-bifunctional ligand that includes a binding agent specific for the particular binding agent and a binding agent specific for the internalizing receptor and the ability of the hetero-bifunctional ligand to induce internalization of one or both of the target receptor and the internalizing receptor is assessed, for example using the procedures outlined in Examples 1-8.

Example 15

Treatment of Subjects

This example describes methods that can be used to treat a subject having a particular disease or condition that can be treated by internalization of a particular target receptor, for example using a hetero-bifunctional ligand, such as the hetero-bifunctional ligands disclosed herein, by administration of one or more of the hetero-bifunctional ligands disclosed herein. For example, the disclosed methods can be used to decrease the surface expression of a particular surface receptor, for example a surface receptor involved in angiogenesis or viral entry into a cell, for example entry of HIV into a cell, for example to decrease or inhibit the deleterious effects of growth factor action, such as the effects of VEGF (by reducing the surface expression of VEGF receptor), for example to treat or reduce the symptoms of cancer. Such a therapy can be used alone or in combination with other therapies (such as administration of an anti-viral agent in the case of a viral infection or the administration of a chemotherapeutic agent in the case of cancer).

In particular examples, the method includes screening a subject having or thought to have a particular disease or condition treatable by the internalization of a particular receptor to identify those subjects that can benefit from administration of the hetero-bifunctional ligands disclosed herein. Subjects of an unknown disease status or condition can be examined to determine if they have disease or condition treatable by internalization of a particular target receptor. Subjects found to (or known to) have a disease or condition contributed to by the activity of a surface expression of a particular target receptor and thereby treatable by internalization of the target receptor are selected to receive one or more of the hetero-bifunctional ligands disclosed herein.

The subject can be administered a therapeutic amount of one or more of the hetero-bifunctional ligands disclosed herein. The hetero-bifunctional ligands can be administered at doses of 1 µg/kg body weight to about 1 mg/kg body weight per dose, such as 1 µg/kg body weight-100 µg/kg body weight per dose, 100 µg/kg body weight-500 µg/kg body weight per dose or 500 µg/kg body weight-1000 µg/kg body weight per dose. However, the particular dose can be determined by a skilled clinician. The agent can be administered in several doses, for example continuously, daily, weekly or monthly.

The mode of administration can be any used in the art. The amount of agent administered to the subject can be determined by a clinician and may depend on the particular subject treated. Specific exemplary amounts are provided herein (but the disclosure is not limited to such doses).

While this disclosure has been described with an emphasis upon particular embodiments, it will be obvious to those of ordinary skill in the art that variations of the particular embodiments may be used and it is intended that the disclosure may be practiced otherwise than as specifically described herein. Features, characteristics, compounds, chemical moieties or examples described in conjunction with a particular aspect, embodiment or example of the invention are to be understood to be applicable to any other aspect, embodiment or example of the invention. Accordingly, this disclosure includes all modifications encompassed within the spirit and scope of the disclosure as defined by the following claims.

We claim:

1. A hetero-bifunctional ligand for use in inducing internalization of a target receptor, comprising:
    a target receptor-binding agent that specifically binds the target receptor on a cell, wherein the target receptor-binding agent is polyguanosine or oligodeoxyguanosine and the target receptor is neuropilin-1;
    a heterologous internalizing receptor-binding agent that specifically binds to an internalizing receptor on the same cell, wherein the internalizing receptor-binding agent is Fucoidan or sulfated dextran and the internalizing receptor is a scavenger receptor; and
    a linker linking the target receptor-binding agent to the internalizing receptor-binding agent, wherein the linker has a length sufficient to allow the hetero-bifunctional ligand to bind to the target receptor and the internalizing receptor on the same cell, wherein binding of the hetero-bifunctional ligand to the internalizing receptor and the target receptor induces internalization of both the internalizing receptor and the target receptor on the same cell.

2. The hetero-bifunctional ligand of claim 1, wherein the linker is a heterologous linker.

3. The hetero-bifunctional ligand of claim 1, wherein the sulfated dextran has a molecular weight average of 500 kilodaltons.

4. The hetero-bifunctional ligand of claim 1, wherein the polyguanosine or oligodeoxyguanosine is between about 6 nucleotides in length and about 100 nucleotides in length.

5. The hetero-bifunctional ligand of claim 4, wherein the polyguanosine or oligodeoxyguanosine is about 18 nucleotides in length.

6. A pharmaceutical composition, comprising a therapeutically effective amount of the hetero-bifunctional ligand of claim 1 and a pharmaceutically acceptable carrier.

7. The hetero-bifunctional ligand of claim 1, wherein the scavenger receptor is SREC-1 (scavenger receptor expressed by endothelial cells I).

8. The hetero-bifunctional ligand of claim 4, wherein the polyguanosine or oligodeoxyguanosine is about 19 nucleotides in length.

9. The hetero-bifunctional ligand of claim 4, wherein the polyguanosine or oligodeoxyguanosine is about 20 nucleotides in length.

10. The hetero-bifunctional ligand of claim 4, wherein the polyguanosine or oligodeoxyguanosine is about 30 nucleotides in length.

11. The hetero-bifunctional ligand of claim 4, wherein the polyguanosine or oligodeoxyguanosine is about 40 nucleotides in length.

12. The hetero-bifunctional ligand of claim 4, wherein the polyguanosine or oligodeoxyguanosine is about 50 nucleotides in length.

13. The hetero-bifunctional ligand of claim 4, wherein the polyguanosine or oligodeoxyguanosine is about 60 nucleotides in length.

14. The hetero-bifunctional ligand of claim 4, wherein the polyguanosine or oligodeoxyguanosine is about 100 nucleotides in length.

* * * * *